US011950835B2

(12) United States Patent
O'Brien et al.

(10) Patent No.: US 11,950,835 B2
(45) Date of Patent: Apr. 9, 2024

(54) CYCLED PULSING TO MITIGATE THERMAL DAMAGE FOR MULTI-ELECTRODE IRREVERSIBLE ELECTROPORATION THERAPY

(71) Applicants: Virginia Tech Intellectual Properties, Inc., Blacksburg, VA (US); AngioDynamics, Inc., Latham, NY (US)

(72) Inventors: Timothy J. O'Brien, Blacksburg, VA (US); Robert E. Neal, II, Richmond, VA (US); Rafael V. Davalos, Blacksburg, VA (US)

(73) Assignees: Virginia Tech Intellectual Properties, Inc., Blacksburg, VA (US); AngioDynamics, Inc., Latham, NY (US)

( * ) Notice: Subject to any disclaimer, the term of this patent is extended or adjusted under 35 U.S.C. 154(b) by 582 days.

(21) Appl. No.: 16/915,760

(22) Filed: Jun. 29, 2020

(65) Prior Publication Data
US 2020/0405373 A1 Dec. 31, 2020

Related U.S. Application Data

(60) Provisional application No. 62/892,636, filed on Aug. 28, 2019, provisional application No. 62/868,235, filed on Jun. 28, 2019.

(51) Int. Cl.
*A61B 18/12* (2006.01)
*A61B 17/00* (2006.01)
(Continued)

(52) U.S. Cl.
CPC .............. *A61B 18/1233* (2013.01); *A61B 2017/00159* (2013.01); *A61B 2017/00172* (2013.01);
(Continued)

(58) Field of Classification Search
CPC ............ A61B 18/1233; A61B 18/1477; A61B 2018/0016; A61B 2018/00577;
(Continued)

(56) References Cited

U.S. PATENT DOCUMENTS 1,653,819 A 12/1927 Northcott
3,730,238 A 5/1973 Butler
(Continued)

FOREIGN PATENT DOCUMENTS

AU 7656800 A 4/2001
AU 2002315095 A1 12/2002
(Continued)

OTHER PUBLICATIONS

Hoejholt, K. L. et al. Calcium electroporation and electrochemotherapy for cancer treatment: Importance of cell membrane composition investigated by lipidomics, calorimetry and in vitro efficacy. Scientific Reports (Mar. 18, 2019) 9:4758, p. 1-12.
(Continued)

*Primary Examiner* — Michael F Peffley
(74) *Attorney, Agent, or Firm* — New River Valley IP Law, P.C.; Michele L. Mayberry; Ashley M. Gates

(57) ABSTRACT

Methods and systems for distributing electrical energy to tissue which minimize Joule heating, thermal effects, and/or thermal damage, without sacrificing efficacy of treatment, are described. The methods and systems are particularly suitable to electrical energy-based therapies employing multiple electrodes, such as arrays of electrodes.

16 Claims, 18 Drawing Sheets

(51) Int. Cl.
  *A61B 18/00* (2006.01)
  *A61B 18/14* (2006.01)
  *A61B 90/00* (2016.01)
  *A61N 1/32* (2006.01)

(52) U.S. Cl.
  CPC ............... *A61B 2017/0019* (2013.01); *A61B 2018/00577* (2013.01); *A61B 2018/00613* (2013.01); *A61B 2018/00732* (2013.01); *A61B 2018/00767* (2013.01); *A61B 2018/1253* (2013.01); *A61B 2018/126* (2013.01); *A61B 2018/1467* (2013.01); *A61B 18/1477* (2013.01); *A61B 2090/0409* (2016.02); *A61N 1/327* (2013.01)

(58) Field of Classification Search
  CPC ........... A61B 2018/00613; A61B 2018/00732; A61B 2018/00767; A61B 2018/00797; A61B 2018/00827; A61B 2018/00892; A61B 2018/124; A61B 2018/1253; A61B 2018/126; A61B 2018/143; A61B 2018/1467; A61B 2017/00172; A61B 2017/00159; A61B 2090/0409; A61N 1/327
  See application file for complete search history.

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,903,707 A | 2/1990 | Knute et al. |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Nguyen |
| 5,439,440 A | 8/1995 | Hofmann |
| 5,458,625 A | 10/1995 | Kendall |
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| D380,272 S | 6/1997 | Partika et al. |
| 5,634,899 A | 6/1997 | Shapland et al. |

(56) References Cited

U.S. PATENT DOCUMENTS

| | | |
|---|---|---|
| 5,643,197 A | 7/1997 | Brucker et al. |
| 5,645,855 A | 7/1997 | Lorenz |
| 5,672,173 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,718,246 A | 2/1998 | Vona |
| 5,720,921 A | 2/1998 | Meserol |
| 5,735,847 A | 4/1998 | Gough et al. |
| 5,752,939 A | 5/1998 | Makoto |
| 5,778,894 A | 7/1998 | Dorogi et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Pearlman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Laufer |
| 5,957,963 A | 9/1999 | Dobak, III |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,120,493 A | 9/2000 | Hofmann |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,135,999 A | 10/2000 | Fanton et al. |
| 6,139,545 A | 10/2000 | Utley et al. |
| 6,150,148 A | 11/2000 | Nanda et al. |
| 6,159,163 A | 12/2000 | Strauss et al. |
| 6,178,354 B1 | 1/2001 | Gibson |
| D437,941 S | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| D442,697 S | 5/2001 | Hajianpour |
| 6,233,490 B1 | 5/2001 | Kasevich |
| 6,235,023 B1 | 5/2001 | Lee et al. |
| D443,360 S | 6/2001 | Haberland |
| 6,241,702 B1 | 6/2001 | Lundquist et al. |
| 6,241,725 B1 | 6/2001 | Cosman |
| D445,198 S | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| D450,391 S | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,375,634 B1 | 4/2002 | Carroll |
| 6,387,671 B1 | 5/2002 | Rubinsky et al. |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |
| 6,443,952 B1 | 9/2002 | Mulier et al. |
| 6,463,331 B1 | 10/2002 | Edwards |
| 6,470,211 B1 | 10/2002 | Ideker et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |

(56) References Cited

U.S. PATENT DOCUMENTS

| | | |
|---|---|---|
| 6,533,784 B2 | 3/2003 | Truckai et al. |
| 6,537,976 B1 | 3/2003 | Gupta |
| 6,540,695 B1 | 4/2003 | Burbank et al. |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,733,516 B2 | 5/2004 | Simons et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Alferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 | 11/2011 | Davalos et al. |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |
| 8,251,986 B2 | 8/2012 | Chornenky et al. |
| 8,267,927 B2 | 9/2012 | Dalal et al. |
| 8,267,936 B2 | 9/2012 | Hushka et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,464 B2 | 6/2013 | Travis et al. |
| 8,465,484 B2 | 6/2013 | Davalos et al. |
| 8,506,564 B2 | 8/2013 | Long et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chornenky et al. |

(56) References Cited

U.S. PATENT DOCUMENTS

| | | | |
|---|---|---|---|
| 8,647,338 B2 | 2/2014 | Chornenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 | 12/2015 | Neal, II et al. |
| 9,283,051 B2 | 3/2016 | Garcia et al. |
| 9,414,881 B2 | 8/2016 | Callas et al. |
| 9,598,691 B2 | 3/2017 | Davalos |
| 9,700,368 B2 * | 7/2017 | Callas | A61B 18/14 |
| 9,764,145 B2 | 9/2017 | Callas et al. |
| 9,867,652 B2 | 1/2018 | Sano et al. |
| 9,943,599 B2 | 4/2018 | Gehl et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Davalos et al. |
| 10,448,989 B2 | 10/2019 | Arena et al. |
| 10,470,822 B2 | 11/2019 | Garcia et al. |
| 10,471,254 B2 * | 11/2019 | Sano | A61B 90/37 |
| 10,537,379 B2 | 1/2020 | Sano et al. |
| 10,694,972 B2 | 6/2020 | Davalos et al. |
| 10,702,326 B2 | 7/2020 | Neal et al. |
| 10,828,085 B2 | 11/2020 | Davalos et al. |
| 10,828,086 B2 | 11/2020 | Davalos et al. |
| 10,959,772 B2 | 3/2021 | Davalos et al. |
| 11,254,926 B2 | 2/2022 | Garcia et al. |
| 11,272,979 B2 | 3/2022 | Garcia et al. |
| 11,311,329 B2 * | 4/2022 | Davalos | A61K 31/519 |
| 11,382,681 B2 * | 7/2022 | Arena | A61B 18/14 |
| 11,406,820 B2 | 8/2022 | Sano et al. |
| 11,453,873 B2 | 9/2022 | Davalos et al. |
| 11,607,271 B2 | 3/2023 | Garcia et al. |
| 11,607,537 B2 | 3/2023 | Latouche et al. |
| 11,737,810 B2 | 8/2023 | Davalos et al. |
| 11,890,046 B2 | 2/2024 | Neal et al. |
| 11,903,690 B2 | 2/2024 | Davalos et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0104318 A1 | 8/2002 | Jaafar et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Smith |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0153960 A1 | 8/2003 | Chornenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193042 A1 | 9/2004 | Scampini et al. |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0004507 A1 | 1/2005 | Schroeppel et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | Mchale et al. |
| 2005/0048651 A1 | 3/2005 | Ryttsen et al. |
| 2005/0049541 A1 | 3/2005 | Behar et al. |
| 2005/0061322 A1 | 3/2005 | Freitag |

(56) References Cited

U.S. PATENT DOCUMENTS

| | | |
|---|---|---|
| 2005/0066974 A1 | 3/2005 | Fields et al. |
| 2005/0112141 A1 | 5/2005 | Terman |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0283149 A1 | 12/2005 | Thorne et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett et al. |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1 | 11/2006 | Rubinsky et al. |
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0278241 A1 | 12/2006 | Ruano |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129720 A1 | 6/2007 | Demarais et al. |
| 2007/0129760 A1 | 6/2007 | Demarais et al. |
| 2007/0151848 A1 | 7/2007 | Novak et al. |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0065062 A1 | 3/2008 | Leung et al. |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1 | 6/2008 | Rubinsky et al. |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326366 A1 | 12/2009 | Krieg |
| 2009/0326436 A1 | 12/2009 | Rubinsky et al. |
| 2009/0326570 A1 | 12/2009 | Brown |
| 2010/0004623 A1 | 1/2010 | Hamilton, Jr. et al. |
| 2010/0006441 A1 | 1/2010 | Renaud et al. |

(56) References Cited

U.S. PATENT DOCUMENTS

| | | |
|---|---|---|
| 2010/0023004 A1 | 1/2010 | Francischelli et al. |
| 2010/0030211 A1 | 2/2010 | Davalos et al. |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long et al. |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1 | 10/2010 | Davalos et al. |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0092973 A1 | 4/2011 | Nuccitelli et al. |
| 2011/0106221 A1 | 5/2011 | Neal et al. |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Aljuri et al. |
| 2011/0166499 A1 | 7/2011 | Demarais et al. |
| 2011/0176037 A1 | 7/2011 | Benkley |
| 2011/0202053 A1 | 8/2011 | Moss et al. |
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071870 A1 | 3/2012 | Salahieh et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0090646 A1 | 4/2012 | Tanaka et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0030239 A1 | 1/2013 | Weyh et al. |
| 2013/0090646 A1 | 4/2013 | Moss et al. |
| 2013/0108667 A1 | 5/2013 | Soikum et al. |
| 2013/0110106 A1 | 5/2013 | Richardson |
| 2013/0184702 A1 | 7/2013 | Neal, II et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1 | 8/2013 | Callas et al. |
| 2013/0253415 A1 | 9/2013 | Sano et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0017218 A1 | 1/2014 | Scott et al. |
| 2014/0039489 A1 | 2/2014 | Davalos et al. |
| 2014/0046322 A1 | 2/2014 | Callas et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0121728 A1 | 5/2014 | Dhillon et al. |
| 2014/0163551 A1 | 6/2014 | Maor et al. |
| 2014/0207133 A1 | 7/2014 | Model et al. |
| 2014/0276748 A1 | 9/2014 | Ku et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0152504 A1 | 6/2015 | Lin |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320478 A1 | 11/2015 | Cosman, Jr. et al. |
| 2015/0320488 A1 | 11/2015 | Moshe et al. |
| 2015/0320999 A1 | 11/2015 | Nuccitelli et al. |
| 2015/0327944 A1 | 11/2015 | Robert et al. |
| 2016/0022957 A1 | 1/2016 | Hobbs et al. |
| 2016/0066977 A1 | 3/2016 | Neal et al. |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338758 A9 | 11/2016 | Davalos et al. |
| 2016/0338761 A1 | 11/2016 | Chornenky et al. |
| 2016/0354142 A1 | 12/2016 | Pearson et al. |
| 2016/0367310 A1 | 12/2016 | Onik et al. |
| 2017/0035501 A1 | 2/2017 | Chornenky et al. |
| 2017/0189579 A1 | 7/2017 | Davalos |
| 2017/0209620 A1 | 7/2017 | Davalos et al. |
| 2017/0266438 A1 | 9/2017 | Sano |
| 2017/0319851 A1 | 11/2017 | Athos et al. |
| 2017/0348525 A1 | 12/2017 | Sano et al. |
| 2017/0360326 A1 | 12/2017 | Davalos |
| 2018/0071014 A1 | 3/2018 | Neal et al. |
| 2018/0125565 A1 | 5/2018 | Sano et al. |
| 2018/0161086 A1 | 6/2018 | Davalos et al. |
| 2018/0198218 A1 | 7/2018 | Regan et al. |
| 2019/0029749 A1 | 1/2019 | Garcia et al. |
| 2019/0046255 A1 | 2/2019 | Davalos et al. |
| 2019/0069945 A1 | 3/2019 | Davalos et al. |
| 2019/0076528 A1 | 3/2019 | Soden et al. |
| 2019/0083169 A1 | 3/2019 | Single et al. |
| 2019/0133671 A1 | 5/2019 | Davalos et al. |
| 2019/0175248 A1 | 6/2019 | Neal, II |
| 2019/0175260 A1 | 6/2019 | Davalos |
| 2019/0223938 A1 | 7/2019 | Virginia |
| 2019/0232048 A1 | 8/2019 | Latouche et al. |
| 2019/0233809 A1 | 8/2019 | Neal et al. |
| 2019/0256839 A1 | 8/2019 | Neal et al. |
| 2019/0282294 A1 | 9/2019 | Davalos et al. |
| 2019/0328445 A1 | 10/2019 | Sano et al. |
| 2019/0351224 A1 | 11/2019 | Sano et al. |
| 2019/0376055 A1 | 12/2019 | Davalos et al. |
| 2020/0046432 A1 | 2/2020 | Garcia et al. |
| 2020/0046967 A1 | 2/2020 | Ivey et al. |
| 2020/0093541 A9 | 3/2020 | Neal et al. |
| 2020/0197073 A1 | 6/2020 | Sano et al. |
| 2020/0260987 A1 | 8/2020 | Davalos et al. |
| 2020/0323576 A1 | 10/2020 | Neal et al. |

(56) References Cited

U.S. PATENT DOCUMENTS

| | | | |
|---|---|---|---|
| 2021/0022795 A1 | 1/2021 | Davalos et al. | |
| 2021/0023362 A1 | 1/2021 | Lorenzo et al. | |
| 2021/0052882 A1 | 2/2021 | Wasson et al. | |
| 2021/0113265 A1 | 4/2021 | D'Agostino et al. | |
| 2021/0137410 A1 | 5/2021 | O'Brien et al. | |
| 2021/0186600 A1 | 6/2021 | Davalos et al. | |
| 2021/0361341 A1 | 11/2021 | Neal et al. | |
| 2021/0393312 A1 | 12/2021 | Davalos et al. | |
| 2022/0151688 A1 | 5/2022 | Garcia et al. | |
| 2022/0161027 A1 | 5/2022 | Aycock et al. | |
| 2022/0290183 A1 | 9/2022 | Davalos et al. | |
| 2022/0362549 A1 | 11/2022 | Sano et al. | |
| 2023/0248414 A1 | 8/2023 | Sano et al. | |
| 2023/0355293 A1 | 11/2023 | Davalos et al. | |
| 2023/0355968 A1 | 11/2023 | Davalos et al. | |

FOREIGN PATENT DOCUMENTS

| | | |
|---|---|---|
| AU | 2003227960 A1 | 12/2003 |
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2009243079 A2 | 1/2011 |
| AU | 2015259303 A1 | 11/2016 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| CN | 106715682 A | 5/2017 |
| CN | 112807074 A | 5/2021 |
| DE | 863111 | 1/1953 |
| DE | 4000893 A1 | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0533511 A1 | 3/1993 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2280741 A1 | 2/2011 |
| EP | 2381829 A1 | 11/2011 |
| EP | 2413833 A1 | 2/2012 |
| EP | 2488251 A2 | 8/2012 |
| EP | 2642937 A2 | 10/2013 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| EP | 3143124 A1 | 3/2017 |
| EP | 3852868 A1 | 7/2021 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 | 7/2011 |
| JP | 2011137025 A | 7/2011 |
| JP | 2012510332 A | 5/2012 |
| JP | 2012515018 A | 7/2012 |
| JP | 2012521863 A | 9/2012 |
| JP | 2014501574 A | 1/2014 |
| JP | 2017518805 A | 7/2017 |
| JP | 6594901 B2 | 10/2019 |
| JP | 2019193668 A | 11/2019 |
| JP | 7051188 B2 | 4/2022 |
| KR | 101034682 A | 5/2011 |
| WO | 9104014 | 4/1991 |
| WO | 9634571 | 11/1996 |
| WO | 9639531 A | 12/1996 |
| WO | 9810745 | 3/1998 |
| WO | 9814238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 0148153 A | 7/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |
| WO | 02100459 A | 12/2002 |
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A | 10/2010 |
| WO | 2010132472 A1 | 11/2010 |

(56) References Cited

FOREIGN PATENT DOCUMENTS

| WO | 2010151277 A | 12/2010 |
|---|---|---|
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012071526 A2 | 5/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |
| WO | 2017117418 A1 | 7/2017 |
| WO | 2020061192 A1 | 3/2020 |
| WO | 2022066768 A1 | 3/2022 |
| WO | 2023172773 A1 | 9/2023 |

OTHER PUBLICATIONS

Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical BI, pp. 512-519, 1999.

Hu, Q., et al., "Simulations of transient membrane behavior in cells subjected to a high-intensity ultrashort electric pulse", Physical Review E, 71(3) (2005).

Huang, et al., Micro-Electroporation: Improving the Efficiency and Understanding of Electrical Permeabilization of Cells, Biomedical Microdevices, vol. 2, pp. 145-150, 1999.

Hughes, et al., An Analysis of Studies Comparing Electrical Impedance Tomography with X-Ray Videofluoroscopy in the Assessment of Swallowing, Physiol. Meas. 15, 1994, pp. A199-A209.

Ibey et al., "Selective cytotoxicity of intense nanosecond-duration electric pulses in mammalian cells." Biochimica Et Biophysica Acta-General Subjects, vol. 1800, pp. 1210-1219 (2010).

Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.

Ivanuša, et al., MRI Macromolecular Contrast Agents as Indicators of Changed Tumor Blood Flow, Radiol. Oncol. 2001; 35(2): 139-47.

Ivey, J. W., E. L. Latouche, M. B. Sano, J. H. Rossmeisl, R. V. Davalos, and S. S. Verbridge, "Targeted cellular ablation based on the morphology of malignant cells," Sci. Rep., vol. 5, pp. 1-17, 2015.

Ivorra et al., "In vivo electric impedance measurements during and after electroporation of rat live." Bioelectrochemistry, vol. 70, pp. 287-295 (2007).

Ivorra et al., "In vivo electrical conductivity measurements during and after tumor electroporation: conductivity changes reflect the treatment outcome." Physics in Medicine and Biology, vol. 54, pp. 5949-5963 (2009).

Ivorra, "Bioimpedance monitoring for physicians: an overview." Biomedical Applications Group, 35 pages (2002).

Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).

Jarm et al., "Antivascular effects of electrochemotherapy: implications in treatment of bleeding metastases." Expert Rev Anticancer Ther. vol. 10, pp. 729-746 (2010).

Jaroszeski, et al., In Vivo Gene Delivery by Electroporation, Advanced Drug Delivery Review, vol. 35, pp. 131-137, 1999.

Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).

Jordan, D.W., et al., "Effect of pulsed, high-power radiofrequency radiation on electroporation of mammalian cells". Ieee Transactions on Plasma Science, 32(4): p. 1573-1578 (2004).

Jossinet et al., Electrical Impedance Endo-Tomography: Imaging Tissue From Inside, IEEE Transactions on Medical Imaging, vol. 21, No. 6, Jun. 2002, pp. 560-565.

Katsuki, S., et al., "Biological effects of narrow band pulsed electric fields", Ieee Transactions on Dielectrics and Electrical Insulation,. 14(3): p. 663-668 (2007).

Kingham et al., "Ablation of perivascular hepatic malignant tumors with irreversible electroporation." Journal of the American College of Surgeons, 2012. 215(3), p. 379-387.

Kinosita and Tsong, "Formation and resealing of pores of controlled sizes in human erythrocyte membrane." Nature, vol. 268 (1977) pp. 438-441.

Kinosita and Tsong, "Voltage-induced pore formation and hemolysis of human erythrocytes." Biochimica et Biophysica Acta (BBA)-Biomembranes, 471 (1977) pp. 227-242.

Kinosita et al., "Electroporation of cell membrane visualized under a pulsed-laser fluorescence microscope." Biophysical Journal, vol. 53, pp. 1015-1019 (1988).

Kinosita, et al., Hemolysis of Human Erythrocytes by a Transient Electric Field, Proc. Natl. Acad. Sci. USA, vol. 74, No. 5, pp. 1923-1927, 1977.

Kirson et al., "Alternating electric fields arrest cell proliferation in animal tumor models and human brain tumors." Proceedings of the National Academy of Sciences vol. 104, pp. 10152-10157 (2007).

Kolb, J.F., et al., "Nanosecond pulsed electric field generators for the study of subcellular effects", Bioelectromagnetics, 27(3): p. 172-187 (2006).

Kotnik and Miklavcic, "Theoretical evaluation of voltage inducement on internal membranes of biological cells exposed to electric fields." Biophysical Journal, vol. 90(2), pp. 480-491 (2006).

Kotnik et al., "Sensitivity of transmembrane voltage induced by applied electric fields—A theoretical analysis", Bioelectrochemistry and Bioenergetics, vol. 43, Issue 2, 1997, pp. 285-291.

Kotnik, T. and D. Miklavcic, "Theoretical evaluation of the distributed power dissipation in biological cells exposed to electric fields", Bioelectromagnetics, 21(5): p. 385-394 (2000).

Kotnik, T., et al., "Cell membrane electropermeabilization by symmetrical bipolar rectangular pulses. Part II. Reduced electrolytic contamination", Bioelectrochemistry, 54(1): p. 91-5 (2001).

Kotnik, T., et al., "Role of pulse shape in cell membrane electropermeabilization", Biochimica Et Biophysica Acta-Biomembranes, 1614(2): p. 193-200 (2003).

Kranjc, M., S. Kranjc, F. Bajd, G. Sersa, I. Sersa, and D. Miklavcic, "Predicting irreversible electroporation-induced tissue damage by means of magnetic resonance electrical impedance tomography," Scientific reports, vol. 7, No. 1, pp. 1-10, 2017.

Labeed et al., "Differences in the biophysical properties of membrane and cytoplasm of apoptotic cells revealed using dielectrophoresis." Biochimica et Biophysica Acta (BBA)-General Subjects, vol. 1760, pp. 922-929 (2006).

Lackovic, I., et al., "Three-dimensional Finite element Analysis of Joule Heating in Electrochemotherapy and in vivo Gene Electrotransfer", Ieee Transactions on Dielectrics and Electrical Insulation, 16(5): p. 1338-1347 (2009).

Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.

Laufer et al., "Electrical impedance characterization of normal and cancerous human hepatic tissue." Physiological Measurement, vol. 31, pp. 995-1009 (2010).

Lebar et al., "Inter-pulse interval between rectangular voltage pulses affects electroporation threshold of artificial lipid pilayers." IEEE Transactions on NanoBioscience, vol. 1 (2002) pp. 116-120.

Lee, E. W et al. Advanced Hepatic Ablation Technique for Creating Complete Cell Death : Irreversible Electroporation. Radiology 255, 426-433, doi:10.1148/radiol. 10090337 (2010).

Lee, E.W., et al., "Imaging guided percutaneous irreversible electroporation: ultrasound and immunohistological correlation", Technol Cancer Res Treat 6: 287-294 (2007).

Lee, R. C., D. J. Canaday, and S. M. Hammer. Transient and stable ionic permeabilization of isolated skeletal muscle cells after electrical shock. J. Burn Care Rehabil. 14:528-540, 1993.

(56) References Cited

OTHER PUBLICATIONS

Li, W., et al., "The Effects of Irreversible Electroporation (IRE) on Nerves" PloS One, Apr. 2011, 6(4), e18831.
Liu, et al., Measurement of Pharyngeal Transit Time by Electrical Impedance Tomography, Clin. Phys. Physiol. Meas., 1992, vol. 13, Suppl. A, pp. 197-200.
Long, G., et al., "Targeted Tissue Ablation With Nanosecond Pulses". Ieee Transactions on Biomedical Engineering, 58(8) (2011).
Lundqvist, et al., Altering the Biochemical State of Individual Cultured Cells and Organelles with Ultramicroelectrodes, Proc. Natl. Acad. Sci. USA, vol. 95, pp. 10356-10360, Sep. 1998.
Lurquin, Gene Transfer by Electroporation, Molecular Biotechnology, vol. 7, 1997.
Lynn, et al., A New Method for the Generation and Use of Focused Ultrasound in Experimental Biology, The Journal of General Physiology, vol. 26, 179-193, 1942.
Maček Lebar and Miklavčič, "Cell electropermeabilization to small molecules in vitro: control by pulse parameters." Radiology and Oncology, vol. 35(3), pp. 193-202 (2001).
Mahmood, F., et al., "Diffusion-Weighted MRI for Verification of Electroporation-Based Treatments", Journal of Membrane Biology 240: 131-138 (2011).
Mahnic-Kalamiza, et al., "Educational application for visualization and analysis of electric field strength in multiple electrode electroporation," BMC Med Educ, vol. 12:102, 13 pages, 2012.
Malpica et al., "Grading ovarian serous carcinoma using a two-tier system." The American Journal of Surgical Pathology, vol. 28, pp. 496-504 (2004).
Pending Application No. CN 201580025135.6, Response to First Office Action, dated Feb. 7, 2020, (Chinese Vrsion, 13 pages, and English Version, 10 pages).
Pending Application No. CN 201580025135.6, Second Office Action, dated Apr. 29, 2020 (Chinese Version, 4 pages, and English Version, 7 pages).
Pending Application No. EP 09739678.2 Extended European Search Report dated May 11, 2012, 7 pages.
Pending Application No. EP 09739678.2, Communication pursuant to Rule 94.3, dated Apr. 16, 2014, 3 bages.
Pending Application No. EP 09739678.2, Office Action dated Apr. 16, 2014, 3 pages.
Pending Application No. EP 09739678.2, Response to Extended European Search Report and Communication pursuant to Rules 70(2) and 70a(2) EPC, dated Dec. 10, 2012.
Pending Application No. EP 10824248.8, Extended Search Report (dated Jan. 20, 2014), 6 pages.
Pending Application No. EP 10824248.8, Invitation Pursuant to rule 62a(1) EPC (dated Sep. 25, 2013), 2 pages.
Pending Application No. EP 10824248.8, Communication Pursuant to Rule 70(2) dated Feb. 6, 2014, 1 page.
Pending Application No. EP 10824248.8, Response to Invitation Pursuant to rule 62a(1) EPC (dated Sep. 25, 2013), Response filed Nov. 18, 2013.
Pending Application No. EP 11842994.3, Communication Pursuant to Rules 70(2) and 70a(2) EPC dated Apr. 28, 2014, 1 page.
Pending Application No. EP 11842994.3, Extended European Search Report dated Apr. 9, 2014, 34 pages.
Pending Application No. EP 15793361.5, Claim amendment filed Jul. 18, 2018, 13 pages.
Pending Application No. EP 15793361.5, European Search Report dated Dec. 4, 2017, 9 pages.
Pending Application No. JP 2013-541050, Voluntary Amendment filed Oct. 29, 2013, 4 pages (with English Version of the Claims, 2 pages).
Pending Application No. JP 2016-567747 Amendment filed Jul. 18, 2019, 7 pgs.
Pending Application No. JP 2016-567747 English translation of amended claims filed Jul. 18, 2019, 6 pgs.
Pending Application No. JP 2016-567747, First Office Action (Translation) dated Feb. 21, 2019, 5 pages.
Pending Application No. JP 2016-567747, First Office Action dated Feb. 21, 2019, 4 pages.
Pending Application No. JP 2016-567747, Decision to Grant with English Version of allowed claims, 9 pages.
Pending Application No. JP 2019-133057, amended claims (English language version) filed Aug. 14, 2019, 5 pages.
Pending Application No. JP 2019-133057, Office Action dated Sep. 14, 2020, 5 pages (and English translation, 6 pages).
Phillips, M., Maor, E. & Rubinsky, B. Non-Thermal Irreversible Electroporation for Tissue Decellularization. J. Biomech. Eng, doi: 10.1115/1.4001882 (2010).
Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.
Polak et al., "On the Electroporation Thresholds of Lipid Bilayers: Molecular Dynamics Simulation Investigations." The Journal of Membrane Biology, vol. 246, pp. 843-850 (2013).
Pucihar et al., "Numerical determination of transmembrane voltage induced on irregularly shaped cells." Annals of Biomedical Engineering, vol. 34, pp. 642-652 (2006).
Qiao et al. Electrical properties of breast cancer cells from impedance measurement of cell suspensions, 2010, Journal of Physics, 224, 1-4 (2010).
Rajagopal, V. and S.G. Rockson, Coronary restenosis: a review of mechanisms and management, The American Journal of Medicine, 2003, 115(7): p. 547-553.
Reberšek, M. and D. Miklavčič, "Advantages and Disadvantages of Different Concepts of Electroporation Pulse Generation," AUTOMATIKA 52(2011) 1, 12-19.
Ringel-Scaia, V. M. et al., High-frequency irreversible electroporation is an effective tumor ablation strategy that Induces immunologic cell death and promotes systemic anti-tumor immunity. EBioMedicine, 2019, 44, 112-125.
Rols, M.P., et al., Highly Efficient Transfection of Mammalian Cells by Electric Field Pulses: Application to Large vols. of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-TIRE)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rossmeisl, John H et al. Safety and feasibility of the NanoKnife system for irreversible electroporation ablative treatment of canine spontaneous intracranial gliomas. J. Neurosurgery 123.4 (2015): 1008-1025.
Rubinsky et al., "Optimal Parameters for the Destruction of Prostate Cancer Using Irreversible Electroporation." The Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: A New Ablation Modality—Clinical Implications" Technol. Cancer Res. Treatment 6(1), 37-48 (2007).
Sabuncu et al., "Dielectrophoretic separation of mouse melanoma clones." Biomicrofluidics, vol. 4, 7 pages (2010).
SAI Infusion Technologies, "Rabbit Ear Vein Catheters", https://www.sai-infusion.com/products/rabbit-ear-catheters, Aug. 10, 2017 webpage printout, 5 pages.
Salford, L.G., et al., "A new brain tumour therapy combining bleomycin with in vivo electropermeabilization", Biochem. Biophys. Res. Commun., 194(2): 938-943 (1993).
Salmanzadeh et al., "Investigating dielectric properties of different stages of syngeneic murine ovarian cancer cells" Biomicrofluidics 7, 011809 (2013), 12 pages.

(56) References Cited

OTHER PUBLICATIONS

Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.
Sanchez, B., G. Vandersteen, R. Bragos, and J. Schoukens, "Optimal multisine excitation design for broadband electrical impedance spec-troscopy," Measurement Science and Technology, vol. 22, No. 11, p. 115601, 2011.
Sano et al., "Contactless Dielectrophoretic Spectroscopy: Examination of the Dielectric Properties of Cells Found in Blood." Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).
Rubinsky, L. et al., "Electrolytic Effects During Tissue Ablation by Electroporation," Technol. Cancer Res. Treat., vol. 15, No. 5, NP95-103, 2016, 9 pages.
Sano, M. B. et al., "Burst and continuous high frequency irreversible electroporation protocols evaluated in a 3D tumor model," Phys. Med. Biol., vol. 63, No. 13, 2018, 17 pages.
Sano, M. B. et al., "Reduction of Muscle Contractions During Irreversible Electroporation Therapy Using High-Frequency Bursts of Alternating Polarity Pulses: A Laboratory Investigation in an Ex Vivo Swine Model," J. Vasc. Interv. Radiol., vol. 29, No. 6, 893-898.e4, Jun. 2018, 18 pages.
U.S. Appl. No. 16/152,743 (U.S. Pat. No. 11,272,979), file history through Jan. 2022, 89 pages.
U.S. Appl. No. 16/275,429 (U.S. Pat. No. 10,959,772), file history through Feb. 2021, 18 pages.
U.S. Appl. No. 16/280,511, file history through Aug. 2021, 31 pages.
U.S. Appl. No. 16/352,759 (U.S. Pat. No. 11,311,329), file history through Mar. 2022, 258 pages.
U.S. Appl. No. 16/372,520 (U.S. Pat. No. 11,382,681), file history through Jun. 2022, 107 pages.
U.S. Appl. No. 16/404,392 (U.S. Pat. No. 11,254,926), file history through Jan. 2022, 153 pages.
U.S. Appl. No. 16/520,901 (U.S. Pat. No. 11,406,820), file history through May 2022, 39 pages.
Valdez, C. M. et al., "The interphase interval within a bipolar nanosecond electric pulse modulates bipolar cancellation," Bioelectromagnetics, vol. 39, No. 6, 441-450, 2018, 28 pages.
Verma, A. et al., "Primer on Pulsed Electrical Field Ablation: Understanding the Benefits and Limitations," Circ. Arrhythmia Electrophysiol., No. September, pp. 1-16, 2021, 16 pages.
Viintin, A. et al., "Effect of interphase and interpulse delay in high-frequency irreversible electroporation pulses on cell survival, membrane permeabilization and electrode material release," Bioelectrochemistry, vol. 134, Aug. 2020, 14 pages.
Wandel, A. et al. "Optimizing Irreversible Electroporation Ablation with a Bipolar Electrode," Journal of Vascular and Interventional Radiology, vol. 27, Issue 9, 1441-1450.e2, 2016.
Yarmush, M. L. et al., "Electroporation-Based Technologies for Medicine: Principles, Applications, and Challenges," Annu. Rev. Biomed. Eng., vol. 16, No. 1, 295-320, 2014, 29 pages.
Zhao, J. et al. "Irreversible electroporation reverses resistance to immune checkpoint blockade in pancreatic cancer", Nature Communications (2019) 10:899, 14 pages.

(Arena, Christopher B. et al.) Co-pending U.S. Appl. No. 15/186,653, filed Jun. 20, 2016, and published as U.S. Publication No. 2016/0287314 on Oct. 6, 2016, Specification, Claims, Figures.
(Arena, Christopher B. et al.) Co-pending U.S. Appl. No. 16/372,520, filed Apr. 2, 2019, which published as 20190223938 on Jul. 25, 2019, Specification, Claims, Figures.
(Arena, Christopher B. et al.) Co-Pending Application No. PCT/US11/66239, filed Dec. 20, 2011, Specification, Claims, Figures.
(Arena, Christopher B. et al.) Co-Pending U.S. Appl. No. 13/332,133, filed Dec. 20, 2011 and published as U.S. Publication No. 2012/0109122 on May 3, 2012, Specification, Claims, Figures.
(Davalos, Rafael et al.) Co-pending U.S. Appl. No. 10/571,162, filed Oct. 18, 2006 (published as 2007/0043345 on Feb. 22, 2007), Specification, Figures, Claims.
(Davalos, Rafael et al.) Co-Pending U.S. Appl. No. 12/757,901, filed Apr. 9, 2010, Specification, Claims, Figures.
(Davalos, Rafael et al.) Co-Pending Application No. PCT/US04/43477, filed Dec. 21, 2004, Specification, Claims, Figures.
(Davalos, Rafael V. et al.) Co-Pending Application No. PCT/US10/53077, filed Oct. 18, 2010, Specification, Claims, Figures.
(Davalos, Rafael V. et al.) Co-Pending U.S. Appl. No. 12/491,151, filed Jun. 24, 2009, and published as U.S. Publication No. 2010/0030211 on Feb. 4, 2010, Specification, Claims, Figures.
(Davalos, Rafael V. et al.) Co-Pending U.S. Appl. No. 12/609,779, filed Oct. 30, 2009, and published as U.S. Publication No. 2010/0331758 on Dec. 30, 2010, Specification, Claims, Figures.
(Davalos, Rafael V. et al.) Co-Pending U.S. Appl. No. 13/919,640, filed Jun. 17, 2013, and published as U.S. Publication No. 2013/0281968 on Oct. 24, 2013, Specification, Claims, Figures.
(Davalos, Rafael V. et al.) Co-Pending U.S. Appl. No. 14/686,380, filed Apr. 14, 2015 and Published as US 2015/0289923 on Oct. 15, 2015, Specification, Claims, Figures.
(Davalos, Rafael V. et al.) Co-pending U.S. Appl. No. 15/424,335, filed Feb. 3, 2017, and published as U.S. Publication No. 2017/0189579 on Jul. 6, 2017, Specification, Claims, Figures.
(Davalos, Rafael V. et al.) Co-pending U.S. Appl. No. 15/536,333, filed Jun. 15, 2017, and published as U.S. Publication No. 2017/0360326 on Dec. 21, 2017, Specification, Claims, Figures.
(Davalos, Rafael V. et al.) Co-pending U.S. Appl. No. 15/881,414, filed Jan. 26, 2018, and published as U.S. Publication No. 2018/0161086 on Jun. 14, 2018, Specification, Claims, Figures.
(Davalos, Rafael V. et al.) Co-pending U.S. Appl. No. 16/177,745, filed Nov. 1, 2018, and published as U.S. Publication No. 2019/0069945 on Mar. 7, 2019, Specification, Claims, Figures.
(Davalos, Rafael V. et al.) Co-pending U.S. Appl. No. 16/232,962 filed Dec. 26, 2018, and published as U.S. Publication No. 2019/0133671 on May 9, 2019, Specification, Claims, Figures.
(Davalos, Rafael V. et al.) Co-pending U.S. Appl. No. 16/275,429, filed Feb. 14, 2019, which published as 2019/0175260 on Jun. 13, 2019, Specification, Claims, Figures.
(Davalos, Rafael V. et al.) Co-pending U.S. Appl. No. 16/352,759, filed Mar. 13, 2019, Specification, Claims, Figures.
(Davalos, Rafael V. et al.) Co-pending U.S. Appl. No. 16/535,451 filed Aug. 8, 2019, and Published as U.S. Publication No. 2019/0376055 on Dec. 12, 2019, Specification, Claims, Figures.
(Davalos, Rafael V. et al.) Co-pending U.S. Appl. No. 16/865,031 filed May 1, 2020, Specification, Claims, Figures.
(Davalos, Rafael V. et al.) Co-pending U.S. Appl. No. 17/069,359 filed Oct. 13, 2020, Specification, Claims, Drawings.
(Davalos, Rafael V. et al.) Co-pending U.S. Appl. No. 17/172,731 filed Feb. 10, 2021, Specification, Claims, Figures.
(Davalos, Rafael V. et al.) Co-Pending Application No. AU 2009243079, filed Apr. 29, 2009 (see PCT/US2009/042100 for documents as filed), Specification, Claims, Figures.
(Davalos, Rafael V. et al.) Co-Pending Application No. PCT/US09/62806, filed Oct. 30, 2009, Specification, Claims, Figures.
(Davalos, Rafael V. et al.) Co-Pending Application No. PCT/US10/30629, filed Apr. 9, 2010, Specification, Claims, Figures.
(Davalos, Rafael V. et al.) Co-pending application No. PCT/US19/51731 filed Sep. 18, 2019, Specification, Claims, Figures.
(Davalos, Rafael V. et al.) Co-Pending U.S. Appl. No. 14/017,210, filed Sep. 3, 2013, and published as U.S. Publication No. 2014/0039489 on Feb. 6, 2014, Specification, Claims, Figures.

(56) References Cited

OTHER PUBLICATIONS (Davalos, Rafael V. et al.) Co-Pending Application No. U.S. Appl. No. 14/627,046, filed Feb. 20, 2015, and published as U.S. Publication No. 2015/0164584 on Jun. 18, 2015, Specification, Claims, Figures.
(Davalos, Rafael V. et al.) Co-Pending International Application No. PCT/US15/65792, filed Dec. 15, 2015, Specification, Claims, Drawings.
(Davalos, Rafael V.) Co-Pending U.S. Appl. No. 12/432,295, filed Apr. 29, 2009, and published as U. S. Publication No. 2009/0269317-A1 on Oct. 29, 2009, Specification, Figures, Claims.
(Davalos, Rafael V.) Co-pending U.S. Appl. No. 15/423,986, filed Feb. 3, 2017, and published as U.S. Publication No. 2017/0209620 on Jul. 27, 2017, Specification, Claims, Figures.
(Davalos, Rafael V.) Co-Pending Application No. CA 2,722,296, filed Apr. 29, 2009, Amended Claims (7 pages), Specification, Figures (See PCT/US2009/042100 for Specification and figures as filed).
(Davalos, Rafael V.) Co-Pending Application No. EP 09739678.2 filed Apr. 29, 2009, Amended Claims (3 pages), Specification and Figures (See PCT/US2009/042100).
(Davalos, Rafael V.) Co-Pending Application No. PCT/US09/42100, filed Apr. 29, 2009, Specification, Claims, Figures.
(Garcia, Paulo A. et al.) Co-Pending U.S. Appl. No. 14/012,832, filed Aug. 28, 2013, and published as U.S. Publication No. 2013/0345697 on Dec. 26, 2013, Specification, Claims, Figures.
(Garcia, Paulo A. et al.) Co-Pending U.S. Appl. No. 14/558,631, filed Dec. 2, 2014, and published as U.S. Publication No. 2015/0088120 on Mar. 26, 2015, Specification, Claims, Figures.
(Garcia, Paulo A. et al.) Co-Pending U.S. Appl. No. 15/011,752, filed Feb. 1, 2016, and published as U.S. Publication No. 2016/0143698 on May 26, 2016, Specification, Claims, Figures.
(Garcia, Paulo A. et al.) Co-Pending U.S. Appl. No. 16/655,845, filed Oct. 17, 2019, Specification, Claims, Figures.
(Garcia, Paulo A. et al.) Co-pending U.S. Appl. No. 16/152,743, filed Oct. 5, 2018, Specification, Claims, Figures.
(Latouche, Eduardo et al.) Co-pending U.S. Appl. No. 16/210,771, filed Dec. 5, 2018, and which published as US Patent Publication No. 2019/0232048 on Aug. 1, 2019, Specification, Claims, Figures.
(Lorenzo, Melvin F. et al.) Co-pending U.S. Appl. No. 16/938,778, filed Jul. 24, 2020, Specification, Claims, Figures.
(Mahajan, Roop L. et al.) Co-Pending U.S. Appl. No. 13/958,152, filed Aug. 2, 2013, Specification, Claims, Figures.
(Neal, Robert E. et al.) Co-Pending U.S. Appl. No. 12/906,923, filed Oct. 18, 2010, Specification, Claims, Figures.
(Neal, Robert E. et al.) Co-Pending U.S. Appl. No. 14/808,679, filed Jul. 24, 2015 and Published as U.S. Publication No. 2015/0327944 on Nov. 19, 2015, Specification, Claims, Figures.
(Neal, Robert E. et al.) Co-Pending U.S. Appl. No. 16/375,878, filed Apr. 5, 2019, which published on Aug. 1, 2019 as US 2019-0233809 A1, Specification, Claims, Figures.
(Neal, Robert E. et al.) Co-pending U.S. Appl. No. 16/404,392, filed May 6, 2019, and published as U.S. Publication No. 2019/0256839 on Aug. 22, 2019, Specification, Claims, Figures.
(Neal, Robert E. et al.) Co-pending U.S. Appl. No. 16/865,772, filed May 4, 2020, Specification, Claims, Figures.
(Neal, Robert E. et al.) Co-Pending U.S. Appl. No. 13/550,307, filed Jul. 16, 2012, and published as U.S. Publication No. 2013/0184702 on Jul. 18, 2013, Specification, Claims, Figures.
Vernier, P.T., et al., "Nanoelectropulse-driven membrane perturbation and small molecule permeabilization", BMC Cell Biology, 7 (2006).
Vidamed, Inc., Transurethral Needle Ablation (TUNA): Highlights from Worldwide Clinical Studies, Vidamed's Office TUNA System, 2001.
Voyer, D., A. Silve, L. M. Mir, R. Scorretti, and C. Poignard, "Dynamical modeling of tissue electroporation," Bioelectrochemistry, vol. 119, pp. 98-110, 2018.

Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.
Weaver et al., "A brief overview of electroporation pulse strength-duration space: A region where additional Intracellular effects are expected." Bioelectrochemistry vol. 87, pp. 236-243 (2012).
Weaver, Electroporation: A General Phenomenon for Manipulating Cells and Tissues, Journal of Cellular Biochemistry, 51: 426-435, 1993.
Weaver, et al., Theory of Electroporation: A Review, Bioelectrochemistry and Bioenergetics, vol. 41, pp. 136-160, 1996.
Weaver, J. C., Electroporation of biological membranes from multicellular to nano scales, IEEE Trns. Dielectr. Electr. Insul. 10, 754-768 (2003).
Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworld.wolfram.com/ (updated May 18, 2011).
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:10.1007/s00270-014-0905-2.
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.
Zhang, Y., et al., MR imaging to assess immediate response to irreversible electroporation for targeted ablation of liver tissues: preclinical feasibility studies in a rodent model. Radiology, 2010. 256(2): p. 424-32.
Zhao, Y., S. Bhonsle, S. Dong, Y. Lv, H. Liu, A. Safaai-Jazi, R. V. Davalos, and C. Yao, "Characterization of conductivity changes during high-frequency irreversible electroporation for treatment planning," IEEE Transactions on Biomedical Engineering, vol. 65, No. 8, pp. 1810-1819, 2017.
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.
Benz, R., et al. "Reversible electrical breakdown of lipid bilayer membranes: a charge-pulse relaxation study". J Membr Biol, 48(2): p. 181-204 (1979).
Bhonsle, S. et al., "Characterization of Irreversible Electroporation Ablation with a Validated Perfused Organ Model," J. Vasc. Interv. Radiol., vol. 27, No. 12, pp. 1913-1922.e2, 2016.
Bhonsle, S., M. F. Lorenzo, A. Safaai Jazi, and R. V. Davalos, "Characterization of nonlinearity and dispersion in issue impedance during high-frequency electroporation," IEEE Transactions on Biomedical Engineering, vol. 65, No. 10, pp. 2190-2201, 2018.
Blad, et al., Impedance Spectra of Tumour Tissue in Comparison with Normal Tissue; a Possible Clinical Application for Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Bonakdar, M., E. L. Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674-2684, 2015.

(56) References Cited

OTHER PUBLICATIONS

Bondarenko, A. and G. Ragoisha, Eis spectrum analyser (the program is available online at http://www.abc.chemistry.bsu.by/vi/analyser/.
Boone, K., Barber, D. & Brown, B. Review—Imaging with electricity: report of the European Concerted Action on Impedance Tomography. J. Med. Eng. Technol. 21, 201-232 (1997).
Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.
Bower et al., "Irreversible electroporation of the pancreas: definitive local therapy without systemic effects." Journal of surgical oncology, 2011. 104(1): p. 22-28.
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Bulvik, B. E. et al. "Irreversible Electroporation versus Radiofrequency AblationD: A Comparison of Local and Systemic Effects in a Small Animal Model," Radiology, vol. 280, No. 2, 2016, 413-424.
Cannon et al., "Safety and early efficacy of irreversible electroporation for hepatic tumors in proximity to vital structures." Journal of Surgical Oncology, 6 pages (2012).
Carpenter A.E. et al., "CellProfiler: image analysis software for identifying and quantifying cell phenotypes." Genome Biol. 2006; 7(10): R100. Published online Oct. 31, 2006, 11 pages.
Castellvi, Q., B. Mercadal, and A. Ivorra, "Assessment of electroporation by electrical impedance methods," in Handbook of electroporation. Springer-Verlag, 2016, pp. 671-690.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 641-652 (1989).
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Chen, M.T., et al., "Two-dimensional nanosecond electric field mapping based on cell electropermeabilization", PMC Biophys, 2(1):9 (2009).
Clark et al., "The electrical properties of resting and secreting pancreas." The Journal of Physiology, vol. 189, pp. 247-260 (1967).
Coates, C.W., et al., "The Electrical Discharge of the Electric Eel, Electrophorous Electricus," Zoologica, 1937, 22(1), pp. 1-32.
Cook, et al., ACT3: A High-Speed, High-Precision Electrical Impedance Tomograph, IEEE Transactions on Biomedical Engineering, vol. 41, No. 8, Aug. 1994.
Corovic et al., "Analytical and numerical quantification and comparison of the local electric field in the tissue for different electrode configurations," Biomed Eng Online, 6, 14 pages, 2007.
Cowley, Good News for Boomers, Newsweek, Dec. 30, 1996/Jan. 6, 1997.
Cox, et al., Surgical Treatment of Atrial Fibrillation: A Review, Europace (2004) 5, S20-S-29.
Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.

Crowley, Electrical Breakdown of Biomolecular Lipid Membranes as an Electromechanical Instability, Biophysical Journal, vol. 13, pp. 711-724, 1973.
Dahl et al., "Nuclear shape, mechanics, and mechanotransduction." Circulation Research vol. 102, pp. 1307-1318 (2008).
Daskalov, I., et al., "Exploring new instrumentation parameters for electrochemotherapy—Attacking tumors with bursts of biphasic pulses instead of single pulses", IEEE Eng Med Biol Mag, 18(1): p. 62-66 (1999).
Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos et al., "Electrical impedance tomography for imaging tissue electroporation," IEEE Transactions on Biomedical Engineering, 51, pp. 761-767, 2004.
Davalos et al., "Theoretical analysis of the thermal effects during in vivo tissue electroporation." Bioelectrochemistry, vol. 61(1-2): pp. 99-107, 2003.
Davalos, et al., A Feasibility Study for Electrical Impedance Tomography as a Means to Monitor Tissue Electroporation for Molecular Medicine, IEEE Transactions on Biomedical Engineering, vol. 49, No. 4, Apr. 2002.
Davalos, et al., Tissue Ablation with Irreversible Electroporation, Annals of Biomedical Engineering, vol. 33, No. 2, og. 223-231, Feb. 2005.
Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).
Davalos, Real-Time Imaging for Molecular Medicine through Electrical Impedance Tomography of Electroporation, Dissertation for Ph.D. in Engineering-Mechanical Engineering, Graduate Division of University of California, Berkeley, 2002.
De Senneville, B. D. et al., "MR thermometry for monitoring tumor ablation," European radiology, vol. 17, No. 9, pp. 2401-2410, 2007.
De Vuyst, E., et al., "In situ bipolar Electroporation for localized cell loading with reporter dyes and investigating gap functional coupling", Biophysical Journal, 94(2): p. 469-479 (2008).
Dean, Nonviral Gene Transfer to Skeletal, Smooth, and Cardiac Muscle in Living Animals, Am J. Physiol Cell Physiol 289: 233-245, 2005.
Demirbas, M. F., "Thermal Energy Storage and Phase Change Materials: An Overview" Energy Sources Part B 1(1), 85-95 (2006).
Dev, et al., Medical Applications of Electroporation, IEEE Transactions of Plasma Science, vol. 28, No. 1, pp. 206-223, Feb. 2000.
Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.
Duraiswami, et al., Boundary Element Techniques for Efficient 2-D and 3-D Electrical Impedance Tomography, Chemical Engineering Science, vol. 52, No. 13, pp. 2185-2196, 1997.
Duraiswami, et al., Efficient 2D and 3D Electrical Impedance Tomography Using Dual Reciprocity Boundary Element Techniques, Engineering Analysis with Boundary Elements 22, (1998) 13-31.
Duraiswami, et al., Solution of Electrical Impedance Tomography Equations Using Boundary Element Methods, Boundary Element Technology XII, 1997, pp. 226-237.
Edd et al., "Mathematical modeling of irreversible electroporation for treatment planning." Technology in Cancer Research and Treatment, vol. 6, No. 4, pp. 275-286 (2007).
(Aycock, Kenneth N. et al.) Co-pending U.S. Appl. No. 17/535,742, filed Nov. 26, 2021, Specification, Claims, and Figures.
(Davalos, Rafael et al.) Co-pending Application No. PCT/US21/51551, filed Sep. 22, 2021, Specification, Claims, Figures.
(Davalos, Rafael V. et al.) Co-pending U.S. Appl. No. 17/277,662, filed Mar. 18, 2021, Specification, Claims, Figures.
(Davalos, Rafael V. et al.) Co-pending Application No. 19861489.3 filed Apr. 16, 2021, Specification, figures (See PCT/US19/51731), and claims (3 pages).
(Garcia, Paulo A. et al.) Co-pending U.S. Appl. No. 17/591,992, filed Feb. 3, 2022, Specification, Claims, Figures.

(56) References Cited

OTHER PUBLICATIONS (Neal, Robert et al.) Co-pending U.S. Appl. No. 17/338,960, filed Jun. 4, 2021, Specification, Claims, Figures.
(Sano, Michael B et al.) Co-pending U.S. Appl. No. 17/862,486, filed Jul. 12, 2022, Specification, Claims, Figures.
Alinezhadbalalami, N. et al., "Generation of Tumor-activated T cells Using Electroporation", Bioelectrochemistry 142 (2021) 107886, Jul. 13, 2021, 11 pages.
Arena, C. B. et al., "Theoretical Considerations of Tissue Electroporation With High-Frequency Bipolar Pulses," IEEE Trans. Biomed. Eng., vol. 58, No. 5, 1474-1482, 2011, 9 pages.
Bhonsle, S. P. et al., "Mitigation of impedance changes due to electroporation therapy using bursts of high-frequency bipolar pulses," Biomed. Eng. (NY)., vol. 14, No. Suppl 3, 14 pages, 2015.
Buist et al., "Efficacy of multi-electrode linear irreversible electroporation," Europace, vol. 23, No. 3, pp. 464-468, 2021, 5 pages.
Butikofer, R. et al., "Electrocutaneous Nerve Stimulation-I: Model and Experiment," IEEE Trans. Biomed. Eng., vol. BME-25, No. 6, 526-531, 1978,6 pages.
Butikofer, R. et al., "Electrocutaneous Nerve Stimulation—II: Stimulus Waveform Selection," IEEE Trans. Biomed. Eng., vol. BME-26, No. 2, 69-75, 1979, abstract only, 2 pages.
Cosman, E. R. et al., "Electric and Thermal Field Effects in Tissue Around Radiofrequency Electrodes," Pain Med., vol. 6, No. 6, 405-424, 2005, 20 pages.
Groen, M. H. A. et al., "In Vivo Analysis of the Origin and Characteristics of Gaseous Microemboli during Catheter-Mediated Irreversible Electroporation," Europace, 2021, 23(1), 139-146.
Guenther, E. et al., "Electrical breakdown in tissue electroporation," Biochem. Biophys. Res. Commun., vol. 467, No. 4, 736-741, Nov. 2015, 15 pages.
Macherey, O. et al., "Asymmetric pulses in cochlear implants: Effects of pulse shape, polarity, and rate," JARO—J. Assoc. Res. Otolaryngol., vol. 7, No. 3, 253-266, 2006, 14 pages.
McIntyre, C. C et al., "Modeling the excitability of mammalian nerve fibers: Influence of afterpotentials on the recovery cycle," J. Neurophysiol., vol. 87, No. 2, 995-1006, 2002, 12 pages.
McNeal, D. R., "Analysis of a Model for Excitation of Myelinated Nerve," IEEE Trans. Biomed. Eng., vol. BME-23, No. 4, 329-337, 1976, 9 pages.
Mercadal, B et al., "Avoiding nerve stimulation in irreversible electroporation: A numerical modeling study," Phys. Med. Biol., vol. 62, No. 20, 8060-8079, 2017, 28 pages.
Miklavčič, D. et al., "The effect of high frequency electric pulses on muscle contractions and antitumor efficiency in vivo for a potential use in clinical electrochemotherapy," Bioelectrochemistry, vol. 65, 121-128, 2004, 8 pages.
Partridge, B. R. et al., "High-Frequency Irreversible Electroporation for treatment of Primary Liver Cancer: A Proof-of-Principle Study in Canine Hepatocellular Carcinoma," J. Vasc. Interv. Radiol., vol. 31, No. 3, 482-491.e4, Mar. 2020, 19 pages.
Patent No. JP 7051188, Opposition dated Jul. 4, 2022 (16 pages) with English translation (13 pages).
PCT Application No. PCT/US19/51731, International Preliminary Report on Patentability dated Mar. 23, 2021, 13 pages.
Pending Application No. PCT/US21/51551, International Search Report and Written Opinion dated Dec. 29, 2021, 14 pages.
Pending U.S. Appl. No. 14/686,380, Advisory Action dated Oct. 20, 2021, 3 pages.
Pending U.S. Appl. No. 14/686,380, Appeal Brief filed Nov. 5, 2021, 21 pages.
Pending U.S. Appl. No. 14/686,380, Applicant Initiated Interview Summary dated Feb. 9, 2021, 3 pages.
Pending U.S. Appl. No. 14/686,380, Applicant Initiated Interview Summary dated Mar. 8, 2021, 2 pages.
Pending U.S. Appl. No. 14/686,380, Examiner's Answer to Appeal Brief, dated Feb. 18, 2022, 16 pages.
Pending U.S. Appl. No. 14/686,380, Reply Brief, dated Apr. 12, 2022, 4 pages.
Pending U.S. Appl. No. 14/686,380, Amendment after Notice of Appeal, dated Oct. 12, 2021, 6 pages.
Pending U.S. Appl. No. 14/686,380, Non-Final Office Action dated May 7, 2021, 17 pages.
Pending U.S. Appl. No. 14/808,679, Appeal Brief, filed Jun. 3, 2021, 25 pages.
Pending U.S. Appl. No. 14/808,679, Appeal Decision dated Jul. 19, 2022, 8 pages.
Pending U.S. Appl. No. 14/808,679, Examiner's Answer to Appeal Brief, dated Sep. 15, 2021, 6 pages.
Pending U.S. Appl. No. 14/808,679, Notice of Allowance dated Aug. 17, 2022, 8 pages.
Pending U.S. Appl. No. 14/808,679, Panel Decision from Pre-Appeal Brief Review, dated Apr. 26, 2021, 2 pages.
Pending U.S. Appl. No. 14/808,679, Pre-Appeal Brief Reasons for Request for Review, dated Mar. 29, 2021, 5 pages.
Pending U.S. Appl. No. 14/808,679, Reply Brief, dated Nov. 15, 2021, 5 pages.
Pending U.S. Appl. No. 16/152,743, Response to Notice to File Corrected Application Papers, filed Jan. 7, 2022, 8 pages.
Pending U.S. Appl. No. 16/210,771, Applicant-Initiated Interview Summary dated Aug. 13, 2021, 4 pages.
Pending U.S. Appl. No. 16/210,771, Final Office Action dated Apr. 13, 2022, 10 pages.
Pending U.S. Appl. No. 16/210,771, Final Office Action dated May 14, 2021, 13 pages.
Pending U.S. Appl. No. 16/210,771, Non-Final Office Action dated Oct. 7, 2021, 10 pages.
Pending U.S. Appl. No. 16/210,771, Notice of Allowance dated Oct. 26, 2022, 8 pages.
Pending U.S. Appl. No. 16/210,771, Response to Apr. 13, 2022 Final Office Action, dated Jul. 13, 2022, 7 pages.
Pending U.S. Appl. No. 16/210,771, Response to May 14, 2021 Final Office Action, filed Aug. 16, 2021, 6 pages.
Pending U.S. Appl. No. 16/210,771, Response to Oct. 7, 2021 Non-Final Office Action, dated Jan. 7, 2022, 7 pages.
Pending U.S. Appl. No. 16/210,771, Rule 1.132 Declaration dated Jan. 7, 2022, 3 pages.
Edd, J., et al., In-Vivo Results of a New Focal Tissue Ablation Technique: Irreversible Electroporaton, IEEE Trans. Biomed. Eng. 53 (2006) p. 1409-1415.
Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).
Eppich et al., "Pulsed electric fields for selection of hematopoietic cells and depletion of tumor cell contaminants." Nature Biotechnology 18, pp. 882-887 (2000).
Erez, et al., Controlled Destruction and Temperature Distributions in Biological Tissues Subjected to Monoactive Electrocoagulation, Transactions of the ASME: Journal of Mechanical Design, vol. 102, Feb. 1980.
Ermolina et al., "Study of normal and malignant white blood cells by time domain dielectric spectroscopy." IEEE Transactions on Dielectrics and Electrical Insulation, 8 (2001) pp. 253-261.
Esser, A.T., et al., "Towards solid tumor treatment by irreversible electroporation: intrinsic redistribution of fields and currents in tissue". Technol Cancer Res Treat, 6(4): p. 261-74 (2007).
Esser, A.T., et al., "Towards Solid Tumor Treatment by Nanosecond Pulsed Electric Fields", Technology in Cancer Research & Treatment, 8(4): p. 289-306 (2009).
Faroja, M., et al., "Irreversible Electroporation Ablation: Is the entire Damage Nonthermal?", Radiology, 266(2), 462-470 (2013).
Fischbach et al., "Engineering tumors with 3D scaffolds." Nat Meth 4, pp. 855-860 (2007).
Flanagan et al., "Unique dielectric properties distinguish stem cells and their differentiated progeny." Stem Cells, vol. 26, pp. 656-665 (2008).
Fong et al., "Modeling Ewing sarcoma tumors in vitro with 3D scaffolds." Proceedings of the National Academy of Sciences vol. 110, pp. 6500-6505 (2013).

(56) References Cited

OTHER PUBLICATIONS

Foster RS, "High-intensity focused ultrasound in the treatment of prostatic disease", European Urology, 1993, vol. 23 Suppl 1, pp. 29-33.

Foster, R.S., et al., Production of Prostatic Lesions in Canines Using Transrectally Administered High-Intensity Focused Ultrasound. Eur. Urol., 1993; 23: 330-336.

Fox, et al., Sampling Conductivity Images via MCMC, Mathematics Department, Auckland University, New Zealand, May 1997.

Frandsen, S. K., H. Gissel, P. Hojman, T. Tramm, J. Eriksen, and J. Gehl. Direct therapeutic applications of calcium electroporation to effectively induce tumor necrosis. Cancer Res. 72:1336-41, 2012.

Freeman, S.A., et al., Theory of Electroporation of Planar Bilayer Membranes—Predictions of the Aqueous Area, Change in Capacitance, and Pore-Pore Separation. Biophysical Journal, 67(1): p. 42-56 (1994).

Garcia et al., "Irreversible electroporation (IRE) to treat brain cancer." ASME Summer Bioengineering Conference, Marco Island, FL, Jun. 25-29, 2008, 2 pages.

Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.

Garcia P.A., et al., "Pilot study of irreversible electroporation for intracranial surgery", Conf Proc IEEE Eng Med Biol Soc, 2009:6513-6516, 2009.

Garcia, et al., "A Parametric Study Delineating Irreversible Electroporation from Thermal Damage Based on a Minimally Invasive Intracranial Procedure," Biomed Eng Online, vol. 10:34, 22 pages, 2011.

Garcia, P. A., et al., "Towards a predictive model of electroporation-based therapies using pre-pulse electrical measurements," Conf Proc IEEE Eng Med Biol Soc, vol. 2012, pp. 2575-2578, 2012.

Garcia, P. A., et al., "Non-thermal Irreversible Electroporation (N-TIRE) and Adjuvant Fractioned Radiotherapeutic Multimodal Therapy for Intracranial Malignant Glioma in a Canine Patient" Technol. Cancer Res. Treatment 10(1), 73-33 (2011).

Garcia, P et al. Intracranial nonthermal irreversible electroporation: in vivo analysis. J Membr Biol 236, 127-136 (2010).

Garcia, Paulo A., Robert E. Neal II and Rafael V. Davalos, Chapter 3, Non-Thermal Irreversible Electroporation for Tissue Ablation, In: Electroporation in Laboratory and Clinical Investigations ISBN 978-1-61668-327-6 Editors: Enrico P. Spugnini and Alfonso Baldi, 2010, 22 pages.

Garcia-Sánchez, T., A. Azan, I. Leray, J. Rosell-Ferrer, R. Bragos, and L. M. Mir, "Interpulse multifrequency electrical Impedance measurements during electroporation of adherent differentiated myotubes," Bioelectrochemistry, vol. 105, pp. 123-135, 2015.

Gascoyne et al., "Membrane changes accompanying the induced differentiation of Friend murine erythroleukemia cells studied by dielectrophoresis." Biochimica et Biophysica Acta (BBA)-Biomembranes, vol. 1149, pp. 119-126 (1993).

Gauger, et al., A Study of Dielectric Membrane Breakdown in the Fucus Egg, J. Membrane Biol., vol. 48, No. 3, pp. 249-264, 1979.

Gawad, S., T. Sun, N. G. Green, and H. Morgan, "Impedance spectroscopy using maximum length sequences: Application to single cell analysis," Review of Scientific Instruments, vol. 78, No. 5, p. 054301, 2007.

Gehl, et al., In Vivo Electroporation of Skeletal Muscle: Threshold, Efficacy and Relation to Electric Field Distribution, Biochimica et Biphysica Acta 1428, 1999, pp. 233-240.

Gençer, et al., Electrical Impedance Tomography: Induced-Current Imaging Achieved with a Multiple Coil System, IEEE Transactions on Biomedical Engineering, vol. 43, No. 2, Feb. 1996.

Gilbert, et al., Novel Electrode Designs for Electrochemotherapy, Biochimica et Biophysica Acta 1334, 1997, pp. 9-14.

Gilbert, et al., The Use of Ultrasound Imaging for Monitoring Cryosurgery, Proceedings 6th Annual Conference, IEEE Engineering in Medicine and Biology, 107-111, 1984.

Gilbert, T. W., et al., "Decellularization of tissues and organs", Biomaterials, Elsevier Science Publishers, Barking, GB, vol. 27, No. 19, Jul. 1, 2006, pp. 3675-3683.

Gimsa et al., "Dielectric spectroscopy of single human erythrocytes at physiological ionic strength: dispersion of the cytoplasm." Biophysical Journal, vol. 71, pp. 495-506 (1996).

Glidewell, et al., The Use of Magnetic Resonance Imaging Data and the Inclusion of Anisotropic Regions in Electrical Impedance Tomography, Biomed. Sci. Instrum. 1993; 29: 251-7.

Golberg, A. and Rubinsky, B., "A statistical model for multidimensional irreversible electroporation cell death in tissue." Biomed Eng Online, 9, 13 pages, 2010.

Gothelf, et al., Electrochemotherapy: Results of Cancer Treatment Using Enhanced Delivery of Bleomycin by Electroporation, Cancer Treatment Reviews 2003: 29: 371-387.

Gowrishankar T.R., et al., "Microdosimetry for conventional and supra-electroporation in cells with organelles". Biochem Biophys Res Commun, 341(4): p. 1266-76 (2006).

Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927, 2009.

Griffiths, et al., A Dual-Frequency Electrical Impedance Tomography System, Phys. Med. Biol., 1989, vol. 34, No. 10, pp. 1465-1476.

Griffiths, The Importance of Phase Measurement in Electrical Impedance Tomography, Phys. Med. Biol., 1987, vol. 32, No. 11, pp. 1435-1444.

Griffiths, Tissue Spectroscopy with Electrical Impedance Tomography: Computer Simulations, IEEE Transactions on Biomedical Engineering, vol. 42, No. 9, Sep. 1995.

Gumerov, et al., The Dipole Approximation Method and Its Coupling with the Regular Boundary Element Method for Efficient Electrical Impedance Tomography, Boundary Element Technology XIII, 1999.

Hapala, Breaking the Barrier: Methods for Reversible Permeabilization of Cellular Membranes, Critical Reviews in Biotechnology, 17(2): 105-122, 1997.

Helczynska et al., "Hypoxia promotes a dedifferentiated phenotype in ductal breast carcinoma in situ." Cancer Research, vol. 63, pp. 1441-1444 (2003).

Heller, et al., Clinical Applications of Electrochemotherapy, Advanced Drug Delivery Reviews, vol. 35, pp. 119-129, 1999.

Hjouj, M., et al., "Electroporation-Induced BBB Disruption and Tissue Damage Depicted by MRI", Neuro-Oncology 13: Issue suppl 3, abstract ET-32 (2011).

Jouj, M., et al., "MRI Study on Reversible and Irreversible Electroporation Induced Blood Brain Barrier Disruption", PLOS ONE, Aug. 2012, 7:8, e42817.

Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. ii114.

Ho, et al., Electroporation of Cell Membranes: A Review, Critical Reviews in Biotechnology, 16(4): 349-362, 1996.

Sano, M. B., et al., "Towards the creation of decellularized organ constructs using irreversible electroporation and active mechanical perfusion", Biomedical Engineering Online, Biomed Central Ltd, London, GB, vol. 9, No. 1, Dec. 10, 2010, p. 83.

Saur et al., "CXCR4 expression increases liver and lung metastasis in a mouse model of pancreatic cancer." Gastroenterology, vol. 129, pp. 1237-1250 (2005).

Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.

Schoenbach et al., "Intracellular effect of ultrashort electrical pulses." Bioelectromagnetics, 22 (2001) pp. 440-448.

Seibert et al., "Clonal variation of MCF-7 breast cancer cells in vitro and in athymic nude mice." Cancer Research, vol. 43, pp. 2223-2239 (1983).

(56) References Cited

OTHER PUBLICATIONS

Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).
Sel, D. et al. Sequential finite element model of tissue electropermeabilization. IEEE Transactions on Biomedical Engineering 52, 816-827, doi:10.1109/tbme.2005.845212 (2005).
Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sersa, et al., Reduced Blood Flow and Oxygenation in SA-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.
Shao, Qi et al. Engineering T cell response to cancer antigens by choice of focal therapeutic conditions, International Journal of Hyperthermia, 2019, DOI: 10.1080/02656736.2018.1539253.
Sharma, A., et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al., Percutaneous ethanol injection therapy for hepatocellular carcinoma: results in 146 patients. AJR, 1993, 160: p. 1023-8.
Szot et al., "3D in vitro bioengineered tumors based on collagen I hydrogels." Biomaterials vol. 32, pp. 7905-7912 (2011).
Talele, S. and P. GAYNOR, "Non-linear time domain model of electropermeabilization: Effect of extracellular conductivity and applied electric field parameters", Journal of Electrostatics, 66(5-6): p. 328-334 (2008).
Talele, S. and P. Gaynor, "Non-linear time domain model of electropermeabilization: Response of a single cell to an arbitrary applied electric field", Journal of Electrostatics, 65(12): p. 775-784 (2007).
Talele, S., et al., "Modelling single cell electroporation with bipolar pulse parameters and dynamic pore radii". Journal of Electrostatics, 68(3): p. 261-274 (2010).
Teissie, J. and T.Y. Tsong, "Electric-Field Induced Transient Pores in Phospholipid-Bilayer Vesicles". Biochemistry, 20(6): p. 1548-1554 (1981).
Tekle, Ephrem, R. Dean Astumian, and p. Boon Chock, Electroporation by using bipolar oscillating electric field: An Improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson et al., "Investigation of the safety of irreversible electroporation in humans," J Vasc Interv Radiol, 22, pp. 611-621, 2011.
Tibbitt et al., "Hydrogels as Extracellular Matrix Mimics for 3D Cell Culture", Jul. 2009, Biotechnol Bioeng, 103 (4),655-663.
TUNA—Suggested Local Anesthesia Guidelines, no date available.
U.S. Appl. No. 12/491,151 (U.S. Pat. No. 8,992,517), file history through Feb. 2015, 113 pages.
U.S. Appl. No. 12/609,779 (U.S. Pat. No. 8,465,484), file history through May 2013, 100 pages.
U.S. Appl. No. 12/757,901 (U.S. Pat. No. 8,926,606), file history through Jan. 2015, 165 pages.
U.S. Appl. No. 12/906,923 (U.S. Pat. No. 9,198,733), file history through Nov. 2015, 55 pages.
U.S. Appl. No. 13/332,133 (U.S. Pat. No. 10,448,989), file history through Sep. 2019, 226 pages.
U.S. Appl. No. 13/550,307 (U.S. Pat. No. 10,702,326), file history through May 2020, 224 pages.
U.S. Appl. No. 13/919,640 (U.S. Pat. No. 8,814,860), file history through Jul. 2014, 41 pages.
U.S. Appl. No. 13/958,152, file history through Dec. 2019, 391 pages.
U.S. Appl. No. 13/989,175 (U.S. Pat. No. 9,867,652), file history through Dec. 2017, 200 pages.
U.S. Appl. No. 14/012,832 (U.S. Pat. No. 9,283,051), file history through Nov. 2015, 17 pages.
U.S. Appl. No. 14/017,210 (U.S. Pat. No. 10,245,098), file history through Jan. 2019, 294 pages.
U.S. Appl. No. 14/558,631 (U.S. Pat. No. 10,117,707), file history through Jul. 2018, 58 pages.
U.S. Appl. No. 14/627,046 (U.S. Pat. No. 10,245,105), file history through Feb. 2019, 77 pages.
U.S. Appl. No. 14/940,863 (U.S. Pat. No. 10,238,447), file history through Oct. 2019, 23 pages.
U.S. Appl. No. 15/011,752 (U.S. Pat. No. 10,470,822), file history through Jul. 2019, 54 pages.
U.S. Appl. No. 15/186,653 (U.S. Pat. No. 10,292,755), file history through Mar. 2019, 21 pages.
U.S. Appl. No. 15/310,114 (U.S. Pat. No. 10,471,254), file history through Aug. 2019, 44 pages.
U.S. Appl. No. 15/423,986 (U.S. Pat. No. 10,286,108), file history through Jan. 2019, 124 pages.
U.S. Appl. No. 15/424,335 (U.S. Pat. No. 10,272,178), file history through Feb. 2019, 57 pages.
U.S. Appl. No. 15/536,333 (U.S. Pat. No. 10,694,972), file history through Apr. 2020, 78 pages.
U.S. Appl. No. 15/843,888 (U.S. Pat. No. 10,537,379), file history through Sep. 2019, 83 pages.
U.S. Appl. No. 15/881,414 (U.S. Pat. No. 10,154,874), file history through Nov. 2018, 43 pages.
U.S. Appl. No. 16/177,745 (U.S. Pat. No. 10,828,085), file history through Jun. 2020, 57 pages.
U.S. Appl. No. 16/232,962 (U.S. Pat. No. 10,828,086), file history through Jun. 2020, 44 pages.
Van Den Bos, W et al., "MRI and contrast-enhanced ultrasound imaging for evaluation of focal irreversible electroporation treatment: results from a phase i-ii study in patients undergoing ire followed by radical prostatectomy," European radiology, vol. 26, No. 7, pp. 2252-2260, 2016.
Verbridge et al., "Oxygen-Controlled Three-Dimensional Cultures to Analyze Tumor Angiogenesis." Tissue Engineering, Part A vol. 16, pp. 2133-2141 (2010).
Pending U.S. Appl. No. 16/375,878, Applicant-Initiated Interview Summary dated Aug. 23, 2022, 7 pages.
Pending U.S. Appl. No. 16/375,878, Final Office Action dated Apr. 15, 2022, 8 pages.
Pending U.S. Appl. No. 16/375,878, Non-Final Office Action dated Jun. 24, 2021, 8 pages.
Pending U.S. Appl. No. 16/375,878, Response to Apr. 15, 2022 Final Office Action, dated Aug. 15, 2022, 8 pages.
Pending U.S. Appl. No. 16/375,878, Response to Jun. 24, 2021 Non-Final Office Action, dated Dec. 22, 2021, 8 pages.
Pending U.S. Appl. No. 16/443,351, Non-Final Office Action, dated Jun. 10, 2022, 15 pages.
Pending U.S. Appl. No. 16/443,351, Response to Jun. 10, 2022 Non-Final Office Action, dated Sep. 12, 2022, 7 pages.
Pending U.S. Appl. No. 16/535,451 Applicant-Initiated Interview Summary for interview held Apr. 7, 2022, 1 page.
Pending U.S. Appl. No. 16/535,451 Final Office Action, dated Feb. 4, 2022, 7 pages.
Pending U.S. Appl. No. 16/535,451 Non-Final Office Action, dated Apr. 19, 2022, 6 pages.
Pending U.S. Appl. No. 16/535,451 Non-Final Office Action, dated Jun. 24, 2021, 12 pages.
Pending U.S. Appl. No. 16/535,451 Notice of Allowance, dated May 16, 2022, 9 pages.
Pending U.S. Appl. No. 16/535,451 Response to Apr. 19, 2022 Non-Final Office Action, dated Apr. 27, 2022, 6 pages.
Pending U.S. Appl. No. 16/535,451 Response to Jun. 24, 2021 Non-Final Office Action, dated Oct. 26, 2021, 10 pages.

(56) References Cited

OTHER PUBLICATIONS

Pending U.S. Appl. No. 16/655,845, Final Office Action, dated Jul. 26, 2022, 7 pages.
Pending U.S. Appl. No. 16/655,845, Non-Final Office Action, dated Mar. 1, 2022, 8 pages.
Pending U.S. Appl. No. 16/655,845, Notice of Allowance, dated Oct. 26, 2022, 7 pages.
Pending U.S. Appl. No. 16/655,845, Response to Jul. 26, 2022 Final Office Action, dated Oct. 6, 2022, 7 pages.
Pending U.S. Appl. No. 16/655,845, Response to Mar. 1, 2022 Non-Final Office Action, dated Jun. 1, 2022, 10 pages.
Pending U.S. Appl. No. 16/655,845, Response to Oct. 21, 2021 Restriction Requirement, dated Dec. 21, 2021, 7 pages.
Pending U.S. Appl. No. 16/655,845, Restriction Requirement, dated Oct. 21, 2021, 6 pages.
Pending U.S. Appl. No. 16/747,219, Applicant-Initiated Interview Summary dated Aug. 3, 2022, 4 pages.
Pending U.S. Appl. No. 16/747,219, Final Office Action dated Nov. 10, 2022, 12 pages.
Pending U.S. Appl. No. 16/747,219, Non-Final Office Action dated Mar. 31, 2022, 12 pages.
Pending U.S. Appl. No. 16/747,219, Response to Mar. 31, 2022 Non-Final Office Action, dated Aug. 1, 2022, 8 pages.
Pending U.S. Appl. No. 16/865,031, Second Preliminary Amendment, filed Sep. 17, 2021, 10 pages.
Pending U.S. Appl. No. 16/865,772, Final Office Action dated Aug. 22, 2022, 18 pages.
Pending U.S. Appl. No. 16/865,772, Non-Final Office Action dated Apr. 11, 2022, 16 pages.
Pending U.S. Appl. No. 16/865,772, Response to Apr. 11, 2022 Non-Final Office Action, dated Jul. 11, 2022, 8 pages.
Pending U.S. Appl. No. 16/865,772, Third Preliminary Amendment, filed Sep. 17, 2021, 6 pages.
Pending U.S. Appl. No. 17/069,359, Preliminary Amendment, filed Sep. 17, 2021, 6 pages.
Pending U.S. Appl. No. 17/172,731, Preliminary Amendment, filed Jun. 27, 2022, 9 pages.
Pending U.S. Appl. No. 17/172,731, Preliminary Amendment, filed Sep. 17, 2021, 7 pages.
Pending U.S. Appl. No. 17/277,662 Preliminary Amendment filed Mar. 18, 2021, 8 pages.
Pending U.S. Appl. No. 17/338,960, Response to Notice to File Missing Parts and Amendment, filed Aug. 16, 2021, 7 pages.
Pending Application No. 19861489.3 Extended European Search Report dated May 16, 2022 (8 pages).
Pending Application No. 19861489.3 Response to Communication pursuant to Rules 161(2) and 162 EPC, filed Nov. 16, 2021, 7 pages.
Pending Application No. AU 2015259303, Certificate of Grant dated Feb. 10, 2022, 1 page.
Pending Application No. AU 2015259303, Notice of Acceptance and Allowed Claims, dated Oct. 15, 2021, 7 pages.
Pending Application No. AU 2015259303, Response to First Examination Report dated Sep. 20, 2021, 126 pages.
Pending Application No. CN 202011281572.3, Amendment filed Sep. 8, 2021 (16 pages) with English Version of the Amended Claims (7 pages).
Pending Application No. EP 15793361.5, Communication Pursuant to Article 94(3) EPC, dated May 3, 2021, 4 pages.
Pending Application No. EP 15793361.5, Response to May 3, 2021 Communication Pursuant to Article 94(3) EPC, dated Nov. 12, 2021, 12 pages.
Pending Application No. JP 2019-133057, Office Action dated Sep. 1, 2021, 3 pages (and English translation, 4 pages).
Pending Application No. JP 2019-133057, Request for Amendment and Appeal filed Dec. 23, 2021 (8 pages) with English Translation of the Amended Claims (2 pages).
Pending Application No. JP 2019-133057, Request for Appeal and Amended Claims (8 pages) with English translation of amended claims (2 pages) dated Dec. 23, 2021.
Pending Application No. JP 2019-133057, Response to Sep. 14, 2020 Office Action filed Mar. 18, 2021 (6 pages) with English Version of claims and response (5 pages).
Polajžer, T et al., "Cancellation effect is present in high-frequency reversible and irreversible electroporation," Bioelectrochemistry, vol. 132, 2020, 11 pages.
Reilly, J. P et al., "Sensory Effects of Transient Electrical Stimulation-Evaluation with a Neuroelectric Model," IEEE Trans. Biomed. Eng., vol. BME-32, No. 12, 1001-1011, 1985, 11 pages.
Rogers, W. R et al., "Strength-duration curve an electrically excitable tissue extended down to near 1 nanosecond," EEE Trans. Plasma Sci., vol. 32, No. 4 II, 1587-1599, 2004, 13 pages.
Pending U.S. Appl. No. 16/152,743 Preliminary Amendment filed Oct. 5, 2018, 7 pages.
Pending U.S. Appl. No. 16/152,743, Non-Final Office Action dated Sep. 25, 2020, 10 pages.
Pending U.S. Appl. No. 16/152,743, Petition for Delayed Claim for Priority dated Dec. 28, 2020, 2 pages.
Pending U.S. Appl. No. 16/152,743, Response to Sep. 25, 2020 Non-Final Office Action dated Dec. 28, 2020, 9 pages.
Pending U.S. Appl. No. 16/152,743, Second Preliminary Amendment filed May 2, 2019, 6 pages.
Pending U.S. Appl. No. 16/210,771, Non-Final Office Action dated Sep. 3, 2020, 9 pages.
Pending U.S. Appl. No. 16/210,771, Preliminary Amendment filed Dec. 5, 2018, 8 pages.
Pending U.S. Appl. No. 16/210,771, Response to Restriction Requirement, filed Jul. 8, 2020, 7 pages.
Pending U.S. Appl. No. 16/210,771, Response to Sept. 3, 2020 Non-Final Office Action filed Jan. 4, 2021, 11 pages.
Pending U.S. Appl. No. 16/210,771, Restriction Requirement, dated Jun. 9, 2020, 7 pages.
Pending U.S. Appl. No. 16/210,771, Second Preliminary Amendment filed Oct. 14, 2019, 7 pages.
Pending U.S. Appl. No. 16/275,429 Notice of Allowance dated Nov. 10, 2020, 9 pages.
Pending U.S. Appl. No. 16/275,429 Preliminary Amendment Filed Mar. 28, 2019, 6 pages.
Pending U.S. Appl. No. 16/280,511, Non-final Office Action dated Dec. 4, 2020, 10 pgs.
Pending U.S. Appl. No. 16/280,511, Preliminary Amendment filed Nov. 2, 2020, 6 pages.
Pending U.S. Appl. No. 16/372,520 Preliminary Amendment filed Apr. 9, 2019, 7 pages.
Pending U.S. Appl. No. 16/375,878, Preliminary Amendment, filed Apr. 9, 2019, 9 pages.
Pending U.S. Appl. No. 16/375,878, Second Preliminary Amendment, filed Feb. 5, 2020, 3 pages.
Pending U.S. Appl. No. 16/404,392, Final Office Action dated Mar. 20, 2020, 8pgs.
Pending U.S. Appl. No. 16/404,392, Interview Summary dated Sep. 6, 2019, 8pgs.
Pending U.S. Appl. No. 16/404,392, Non-Final Office Action dated Nov. 13, 2020, 8pgs.
Pending U.S. Appl. No. 16/404,392, Non-Final Office Action dated Sep. 6, 2019, 8pgs.
Pending U.S. Appl. No. 16/404,392, Petition for Priority, filed Jun. 4, 2019, 2 pages.
Pending U.S. Appl. No. 16/404,392, Preliminary Amendment, filed Jun. 4, 2019, 9 pages.
Pending U.S. Appl. No. 16/404,392, Preliminary Amendment, filed Jun. 6, 2019, 5 pages.
Pending U.S. Appl. No. 16/404,392, Response to Final Office action dated Mar. 20, 2020, filed Sep. 18, 2020, 7 pages.
Pending U.S. Appl. No. 16/404,392, Response to Non-Final Office action dated Sep. 6, 2019, filed Dec. 6, 2019, 8 pages.
Pending U.S. Appl. No. 16/404,392, Response to the Nov. 13, 2020 Non-Final Office action, filed Feb. 16, 2021, 8 pages.
Pending U.S. Appl. No. 16/443,351, Preliminary amendment filed Feb. 3, 2020.
Pending U.S. Appl. No. 16/520,901, Preliminary Amendment filed Aug. 14, 2019.

(56) References Cited

OTHER PUBLICATIONS

Pending U.S. Appl. No. 16/520,901, Second Preliminary Amendment filed Feb. 4, 2020.
Pending U.S. Appl. No. 16/535,451 Preliminary Amendment filed Aug. 8, 2019, 3 pages.
Pending U.S. Appl. No. 16/535,451 Second Preliminary Amendment filed Oct. 9, 2019, 15 pages.
Pending U.S. Appl. No. 16/535,451 Third Preliminary Amendment filed Nov. 5, 2019, 4 pages.
Pending U.S. Appl. No. 16/655,845, Preliminary Amendment filed Oct. 16, 2020, 6 pages.
Pending U.S. Appl. No. 16/747,219, Preliminary Amendment filed Jan. 20, 2020, 5 pages.
Pending U.S. Appl. No. 16/747,219, Preliminary Amendment filed Jan. 4, 2021, 5 pages.
Pending U.S. Appl. No. 16/865,031, Preliminary Amendment filed May 1, 2020, 7 pages.
Pending U.S. Appl. No. 16/865,772, Preliminary Amendment filed May 4, 2020, 6 pages.
Pending U.S. Appl. No. 16/865,772, Second Preliminary Amendment filed Jun. 30, 2020, 4 pages.
Pending Application No. AU 2009243079, First Examination Report, Jan. 24, 2014, 4 pages.
Pending Application No. AU 2009243079, Voluntary Amendment filed Dec. 6, 2010, 35 pages.
Pending Application No. AU 2015259303, First Examination Report dated Oct. 26, 2020, 6 pages.
Pending Application No. CA 2,722,296 Examination Report dated Apr. 2, 2015, 6 pages.
Pending Application No. CN 201580025135.6 English translation of Apr. 29, 2020 Office action, 7 pages.
Pending Application No. CN 201580025135.6 English translation of Sep. 25, 2019 Office action.
Pending Application No. CN 201580025135.6 Preliminary Amendment filed with application Nov. 14, 2016.
Pending Application No. CN 201580025135.6 Response to Sep. 25, 2019 Office action, filed Feb. 10, 2020, English language version and original document.
Pending Application No. CN 201580025135.6, First Office Action, dated Sep. 25, 2019 (Chinese and English Versions, each 6 pages).
(Neal, Robert E et al.) Co-Pending U.S. Appl. No. 14/940,863, filed Nov. 13, 2015 and Published as US 2016/0066977 on Mar. 10, 2016, Specification, Claims, Figures.
(Neal, Robert et al.) Co-pending U.S. Appl. No. 16/280,511, filed Feb. 20, 2019, and published as U. S. Publication No. 2019/0175248 on Jun. 13, 2019, Specification, Claims, Figures.
(Neal, Robert et al.) Co-Pending Application No. EP 10824248.8, filed May 9, 2012, Amended Claims (3 pages), Specification and Figures (See PCT/US10/53077).
(O'Brien, Timothy J. et al.) Co-Pending U.S. Appl. No. 17/152,379, filed Jan. 19, 2021, Specification, Claims, Figures.
(Pearson, Robert M. et al.) Co-pending Application No. PCT/US2010/029243, filed Mar. 30, 2010, published as WO 2010/117806 on Oct. 14, 2010, Specification, Claims, Figures.
(Pearson, Robert M. et al.) Co-pending U.S. Appl. No. 12/751,826, filed Mar. 31, 2010 (published as 2010/0250209 on Sep. 30, 2010), Specification, Claims, Figures.
(Pearson, Robert M. et al.) Co-pending U.S. Appl. No. 12/751,854, filed Mar. 31, 2010 (published as 2010/0249771 on Sep. 30, 2010), Specification, Claims, Figures.
(Sano, Michael B. et al.) Co-Pending Application No. PCT/US2015/030429, Filed May 12, 2015, Published on Nov. 19, 2015 as WO 2015/175570, Specification, Claims, Figures.
(Sano, Michael B. et al.) Co-Pending U.S. Appl. No. 13/989,175, filed May 23, 2013, and published as U.S. Publication No. 2013/0253415 on Sep. 26, 2013, Specification, Claims, Figures.
(Sano, Michael B. et al.) Co-Pending U.S. Appl. No. 15/310,114, filed Nov. 10, 2016, and published as U.S. Publication No. 2017/0266438 on Sep. 21, 2017, Specification, Claims, Figures.
(Sano, Michael B. et al.) Co-pending U.S. Appl. No. 15/843,888, filed Dec. 15, 2017, and published as U.S. Publication No. 2018/0125565 on May 10, 2018, Specification, Claims, Figures.
(Sano, Michael B. et al.) Co-pending U.S. Appl. No. 16/443,351, filed Jun. 17, 2019 (published as 20190328445 on Oct. 31, 2019), Specification, Claims, Figures.
(Sano, Michael B. et al.) Co-pending U.S. Appl. No. 16/520,901, filed Jul. 24, 2019, and published as U.S. Publication No. 2019/0351224 on Nov. 21, 2019, Specification, Claims, Figures.
(Sano, Michael B. et al.) Co-Pending U.S. Appl. No. 16/747,219, filed Jan. 20, 2020, Specification, Claims, Figures.
(Sano, Michael B. et al.) Co-Pending Application No. AU 2015259303, filed Oct. 24, 2016, Specification, Figures, Claims.
(Sano, Michael B. et al.) Co-Pending Application No. CN 201580025135.6, filed Nov. 14, 2016, Specification, Claims, Figures (Chinese language and english language versions).
(Sano, Michael B. et al.) Co-Pending Application No. CN 202011281572.3, filed Nov. 16, 2020, Specification, Claims, Figures (Chinese version, 129 pages (see also WO 2015/175570), English Version of claims, 2 pages).
(Sano, Michael B. et al.) Co-Pending Application No. EP 11842994.3, filed Jun. 24, 2013, Amended Claims (18 pages), Specification and Figures (See PCT/US11/62067).
(Sano, Michael B. et al.) Co-Pending Application No. EP 15793361.5, filed Dec. 12, 2016, Specification, Claims, Figures.
(Sano, Michael B. et al.) Co-pending application No. HK 17112121.8, filed Nov. 20, 2017 and published as Publication No. HK1238288 on Apr. 27, 2018, Specification, Claims, Figures (See PCT/US15/30429 for English Version of documents as filed).
(Sano, Michael B. et al.) Co-Pending Application No. JP 2013-541050, filed May 22, 2013, Claims, Specification, and Figures (See PCT/US11/62067 for English Version).
(Sano, Michael B. et al.) Co-Pending Application No. JP 2016-567747, filed Nov. 10, 2016, Specification, Claims, Figures (see PCT/US15/30429 for English Version of documents as filed).
(Sano, Michael B. et al.) Co-pending Application No. JP 2019-133057 filed Jul. 18, 2019, 155 pgs, Specification, Claims, Figures (See PCT/US15/30429 for English Version of documents as filed).
(Sano, Michael et al.) Co-Pending Application No. PCT/US11/62067, filed Nov. 23, 2011, Specification, Claims, Figures.
(Wasson, Elisa M. et al.) Co-pending U.S. Appl. No. 17/000,049, filed Aug. 21, 2020, Specification, Claims, Figures.
Abiror, I.G., et al., "Electric Breakdown of Bilayer Lipid-Membranes .1. Main Experimental Facts and Their Qualitative Discussion", Bioelectrochemistry and Bioenergetics, 6(1): p. 37-52 (1979).
Agerholm-Larsen, B., et al., "Preclinical Validation of Electrochemotherapy as an Effective Treatment for Brain Tumors", Cancer Research 71: 3753-3762 (2011).
Alberts et al., "Molecular Biology of the Cell," 3rd edition, Garland Science, New York, 1994, 1 page.
Al-Sakere et al., "Tumor ablation with irreversible electroporation," PLoS ONE, 2, e1135, 2007, 8 pages.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss. Cult. Meth., 15:56-62, 1993.
Appelbaum, L., et al., "US Findings after Irreversible Electroporation Ablation: Radiologic-Pathologic Correlation" Radiology 262(1), 117-125 (2012).
Arena et al. "High-Frequency Irreversible Electroporation (H-FIRE) for Non-thermal Ablation without Muscle Contraction." Biomed. Eng. Online, vol. 10, 20 pages (2011).
Arena, C.B., et al., "A three-dimensional in vitro tumor platform for modeling therapeutic irreversible electroporation." Biophysical Journal, 2012.103(9): p. 2033-2042.
Arena, Christopher B., et al., "Towards the development of latent heat storage electrodes for electroporation-based therapies", Applied Physics Letters, 101, 083902 (2012).
Arena, Christopher B., et al., "Phase Change Electrodes for Reducing Joule Heating During Irreversible Electroporation". Proceedings

(56) References Cited

OTHER PUBLICATIONS of the ASME 2012 Summer Bioengineering Conference, SBC2012, Jun. 20-23, 2012, Fajardo, Puerto Rico.
Asami et al., "Dielectric properties of mouse lymphocytes and erythrocytes." Biochimica et Biophysica Acta (BBA)-Molecular Cell Research, 1010 (1989) pp. 49-55.
Bagla, S. and Papadouris, D., "Percutaneous Irreversible Electroporation of Surgically Unresectable Pancreatic Cancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Ball, C., K.R. Thomson, and H. Kavnoudias, "Irreversible electroporation: a new challenge in "out of-operating theater" anesthesia." Anesth Analg, 2010. 110(5): p. 1305-9.
Bancroft, et al., Design of a Flow Perfusion Bioreactor System for Bone Tissue-Engineering Applications, Tissue Engineering, vol. 9, No. 3, 2003, p. 549-554.
Baptista et al., "The Use of Whole Organ Decellularization for the Generation of a Vascularized Liver Organoid," Heptatology, vol. 53, No. 2, pp. 604-617 (2011).
Barber, Electrical Impedance Tomography Applied Potential Tomography, Advances in Biomedical Engineering, Beneken and Thevenin, eds., IOS Press, pp. 165-173, 1993.
Beebe, S.J., et al., "Diverse effects of nanosecond pulsed electric fields on cells and tissues", DNA and Cell Biology, 22(12): 785-796 (2003).
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No. 01CH37251). IEEE, Part vol. 1, 2001, pp. 211-215, vol. I, Piscataway, NJ, USA.
Beebe, S.J., et al.,, "Nanosecond, high-intensity pulsed electric fields induce apoptosis in human cells", FASEB J, 17(9): p. 1493-5 (2003).
Beitel-White, N., S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173.
Belehradek, J., et al., "Electropermeabilization of Cells in Tissues Assessed by the Qualitative and Quantitative Electroloading of Bleomycin", Biochimica Et Biophysica Acta-Biomembranes, 1190(1): p. 155-163 (1994).
Ben-David, E. et al., "Irreversible Electroporation: Treatment Effect Is Susceptible to Local Environment and Tissue Properties," Radiology, vol. 269, No. 3, 2013, 738-747.
Ben-David, E., et al., "Characterization of Irreversible Electroporation Ablation in In Vivo Procine Liver" Am. J. Roentgenol. 198(1), W62-W68 (2012).
Maor et al., The Effect of Irreversible Electroporation on Blood Vessels, Tech. in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.
Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.
Marszalek et al., "Schwan equation and transmembrane potential induced by alternating electric field." Biophysical Journal, vol. 58, pp. 1053-1058 (1990).
Martin, n.R.C.G., et al., "Irreversible electroporation therapy in the management of locally advanced pancreatic adenocarcinoma." Journal of the American College of Surgeons, 2012. 215(3): p. 361-369.
Martinsen, O. G. and Grimnes, S., Bioimpedance and bioelectricity basics. Academic press, 2011.

Marty, M., et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, 3-13, 2006.
Miklavčič, et al., A Validated Model of an in Vivo Electric Field Distribution in Tissues for Electrochemotherapy and for DNA Electrotransfer for Gene Therapy, Biochimica et Biophysica Acta 1523 (2000), pp. 73-83.
Miklavčič, et al., The Importance of Electric Field Distribution for Effective in Vivo Electroporation of Tissues, Biophysical Journal, vol. 74, May 1998, pp. 2152-2158.
Miller, L., et al., Cancer cells ablation with irreversible electroporation, Technology in Cancer Research and Treatment 4 (2005) 699-706.
Min, M., A. Giannitsis, R. Land, B. Cahill, U. Pliquett, T. Nacke, D. Frense, G. Gastrock, and D. Beckmann, "Comparison of rectangular wave excitations in broad band impedance spectroscopy for microfluidic applications," in World Congress on Medical Physics and Biomedical Engineering, Sep. 7-12, 2009, Munich, Germany. Springer, 2009, pp. 85-88.
Min, M., U. Pliquett, T. Nacke, A. Barthel, P. Annus, and R. Land, "Broadband excitation for short-time impedance spectroscopy," Physiological measurement, vol. 29, No. 6, p. S185, 2008.
Mir et al., "Mechanisms of Electrochemotherapy" Advanced Drug Delivery Reviews 35:107-118 (1999).
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.
Mir, et al., Electrochemotherapy, a Novel Antitumor Treatment: First Clinical Trial, C.R. Acad. Sci. Paris, Ser. III, vol. 313, pp. 613-618, 1991.
Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.
Mir, L.M., et al., Electric Pulse-Mediated Gene Delivery to Various Animal Tissues, in Advances in Genetics, Academic Press, 2005, p. 83-114.
Mir, Therapeutic Perspectives of In Vivo Cell Electropermeabilization, Bioelectrochemistry, vol. 53, pp. 1-10, 2000.
Mulhall et al., "Cancer, pre-cancer and normal oral cells distinguished by dielectrophoresis." Analytical and Bioanalytical Chemistry, vol. 401, pp. 2455-2463 (2011).
Narayan, et al., Establishment and Characterization of a Human Primary Prostatic Adenocarcinoma Cell Line (ND-1), The Journal of Urology, vol. 148, 1600-1604, Nov. 1992.
Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.
Naslund, Michael J., Transurethral Needle Ablation of the Prostate, Urology, vol. 50, No. 2, Aug. 1997.
Neal II et al., "A Case Report on the Successful Treatment of a Large Soft-Tissue Sarcoma with Irreversible Electroporation," Journal of Clinical Oncology, 29, pp. 1-6, 2011.
Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.
Neal II, R. E et al. In Vitro and Numerical Support for Combinatorial Irreversible Electroporation and Electrochemotherapy Glioma Treatment. Annals of Biomedical Engineering, Oct. 29, 2013, 13 pages.
Neal II, R. E., et al., "Successful Treatment of a Large Soft Tissue Sarcoma with Irreversible Electroporation", Journal of Clinical Oncology, 29:13, e372-e377 (2011).

(56) References Cited

OTHER PUBLICATIONS

Neal II, R.E., et al., "Treatment of breast cancer through the application of irreversible electroporation using a novel minimally invasive single needle electrode." Breast Cancer Research and Treatment, 2010. 123(1): p. 295-301.
Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.
Neal RE II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.
Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).
Neumann, et al., Gene Transfer into Mouse Lyoma Cells by Electroporation in High Electric Fields, J. Embo., vol. 1, No. 7, pp. 841-845, 1982.
Neumann, et al., Permeability Changes Induced by Electric Impulses in Vesicular Membranes, J. Membrane Biol., vol. 10, pp. 279-290, 1972.
Nikolova, B., et al., "Treatment of Melanoma by Electroporation of Bacillus Calmette-Guerin". Biotechnology & Biotechnological Equipment, 25(3): p. 2522-2524 (2011).
Nuccitelli, R., et al., "A new pulsed electric field therapy for melanoma disrupts the tumor's blood supply and causes complete remission without recurrence", Int J Cancer, 125(2): p. 438-45 (2009).
O'Brien et al., "Investigation of the Alamar Blue (resazurin) fluorescent dye for the assessment of mammalian cell cytotoxicity." European Journal of Biochemistry, vol. 267, pp. 5421-5426 (2000).
O'brien, T. J. et al., "Effects of internal electrode cooling on irreversible electroporation using a perfused organ model," Int. J. Hyperth., vol. 35, No. 1, pp. 44-55, 2018.
Okino, et al., Effects of High-Voltage Electrical Impulse and an Anticancer Drug on In Vivo Growing Tumors, Japanese Journal of Cancer Research, vol. 78, pp. 1319-1321, 1987.
Onik, et al., Sonographic Monitoring of Hepatic Cryosurgery in an Experimental Animal Model, AJR American J. of Roentgenology, vol. 144, pp. 1043-1047, May 1985.
Onik, et al., Ultrasonic Characteristics of Frozen Liver, Cryobiology, vol. 21, pp. 321-328, 1984.
Onik, G. and B. Rubinsky, eds. "Irreversible Electroporation: First Patient Experience Focal Therapy of Prostate Cancer. Irreversible Electroporation", ed. B. Rubinsky 2010, Springer Berlin Heidelberg, pp. 235-247.
Onik, G., P. Mikus, and B. Rubinsky, "Irreversible electroporation: implications for prostate ablation." Technol Cancer Res Treat, 2007. 6(4): p. 295-300.
Organ, L.W., Electrophysiological principles of radiofrequency lesion making, Apply. Neurophysiol., 1976. 39: p. 69-76.
Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.
Pakhomova, O. N., Gregory, B., Semenov I., and Pakhomov, A. G., BBA—Biomembr., 2014, 1838, 2547-2554.
Paszek et al., "Tensional homeostasis and the malignant phenotype." Cancer Cell, vol. 8, pp. 241-254 (2005).
Pavselj, N. et al. The course of tissue permeabilization studied on a mathematical model of a subcutaneous tumor in small animals. IEEE Trans Biomed Eng 52, 1373-1381 (2005).
Pavselj, N., et al., "A numerical model of skin electroporation as a method to enhance gene transfection in skin. 11th Mediterranean Conference on Medical and Biological Engineering and Computing", vols. 1 and 2, 16(1-2): p. 597-601 (2007).
PCT Application No. PCT/2011/062067, International Preliminary Report on Patentability dated May 28, 2013.
PCT Application No. PCT/2011/066239, International Preliminary Report on Patentability dated Jun. 25, 2013.
PCT Application No. PCT/US09/62806, International Search Report (dated Jan. 19, 2010), Written Opinion (dated Jan. 19, 2010), and International Preliminary Report on Patentability (dated Jan. 4, 2010), 15 pgs.
PCT Application No. PCT/US10/53077, International Search Report (dated Aug. 2, 2011), Written Opinion (dated Aug. 2, 2011), and International Preliminary Report on Patentability (dated Apr. 17, 2012).
PCT Application No. PCT/US15/30429, International Search Report and Written Opinion dated Oct. 16, 2015, 19 pages.
PCT Application No. PCT/US15/30429, International Report on Patentability dated Nov. 15, 2016.
PCT Application No. PCT/US15/65792, International Search Report (dated Feb. 9, 2016), Written Opinion (dated Feb. 9, 2016), and International Preliminary Report on Patentability (dated Jun. 20, 2017), 15 pages.
PCT Application No. PCT/US19/51731, International Search Report and Written Opinion dated Feb. 20, 2020, 19 pgs.
PCT Application No. PCT/US19/51731, Invitation to Pay Additional Search Fees dated Oct. 28, 2019, 2 pgs.
PCT Application No. PCT/US2004/043477, International Search Report (dated Aug. 26, 2005), Written Opinion (dated Aug. 26, 2005), and International Preliminary Report on Patentability (dated Jun. 26, 2006).
PCT Application No. PCT/US2009/042100, International Search Report (dated Jul. 9, 2009), Written Opinion (dated Jul. 9, 2009), and International Preliminary Report on Patentability (dated Nov. 2, 2010).
PCT Application No. PCT/US2010/029243, International Search Report, 4 pgs, (Jul. 30, 2010), Written Opinion, 7 pgs, (dated Jul. 30, 2010), and International Preliminary Report on Patentability, 8 pgs, (dated Oct. 4, 2011).
PCT Application No. PCT/US2010/030629, International Search Report (dated Jul. 15, 2010), Written Opinion (dated Jul. 15, 2010), and International Preliminary Report on Patentability (dated Oct. 11, 2011).
PCT Application No. PCT/US2011/062067, International Search Report and Written Opinion dated Jul. 25, 2012.
PCT Application No. PCT/US2011/066239, International Search Report (dated Aug. 22, 2012), and Written Opinion (dated Aug. 22, 2012).
Pending U.S. Appl. No. 14/686,380, Final Office Action dated May 9, 2018, 14 pages.
Pending U.S. Appl. No. 14/686,380, Final Office Action dated Oct. 6, 2020, 14 pages.
Pending U.S. Appl. No. 14/686,380, Final Office Action dated Sep. 3, 2019, 28 pages.
Pending U.S. Appl. No. 14/686,380, Non-Final Office Action dated Feb. 13, 2020, 11 pages.
Pending U.S. Appl. No. 14/686,380, Non-Final Office Action dated May 1, 2019, 18 pages.
Pending U.S. Appl. No. 14/686,380, Non-Final Office Action dated Nov. 22, 2017, 11 pages.
Pending U.S. Appl. No. 14/686,380, Response to Feb. 13, 2020 Non-Final Office Action, filed Jul. 1, 2020, 8 pages.
Pending U.S. Appl. No. 14/686,380, Response to Jul. 19, 2017 Restriction Requirement, dated Sep. 15, 2017, 2 pages.
Pending U.S. Appl. No. 14/686,380, Response to May 9, 2018 Final Office Action with RCE, dated Aug. 30, 2018, 14 pages.
Pending U.S. Appl. No. 14/686,380, Response to Non-Final Office Action Filed Aug. 1, 2019, 11 pages.
Pending U.S. Appl. No. 14/686,380, Response to Nov. 22, 2017 Non-Final Office Action dated Mar. 28, 2018, 11 pages.
Pending U.S. Appl. No. 14/686,380, Response to Oct. 6, 2020 Final Office Action with RCE, dated Jan. 6, 2020, 11 pages.
Pending U.S. Appl. No. 14/686,380, Response to Sep. 3, 2019 Final Office Action, filed Jan. 3, 2020, 10 pages.
Pending U.S. Appl. No. 14/686,380, Restriction Requirement dated Jul. 19, 2017, 7 pages.
Pending U.S. Appl. No. 14/808,679, Interview Summary, dated Apr. 26, 2019, 3 pages.

(56) References Cited

OTHER PUBLICATIONS

Pending U.S. Appl. No. 14/808,679, Preliminary Amendment dated Jul. 24, 2015, 6 pages.
Pending U.S. Appl. No. 14/808,679, Restriction Requirement dated Mar. 19, 2018, 7 pages.
Pending U.S. Appl. No. 14/808,679, 3rd Renewed Petition, Dec. 9, 2019 and Petition Decision Dec. 18. 2019, 11 pages.
Pending U.S. Appl. No. 14/808,679, Final Office Action dated Dec. 28, 2020, 11 pages.
Pending U.S. Appl. No. 14/808,679, Final Office Action dated Jan. 11, 2019, 12 pages.
Pending U.S. Appl. No. 14/808,679, Non-Final Office Action dated Jun. 12, 2020, 10 pages.
Pending U.S. Appl. No. 14/808,679, Non-Final Office Action dated Sep. 10, 2018, 12 pages.
Pending U.S. Appl. No. 14/808,679, Petition Decision, dated Oct. 1, 2019, 5 pages.
Pending U.S. Appl. No. 14/808,679, Petition Decision, dated Oct. 23, 2019, 6 pages.
Pending U.S. Appl. No. 14/808,679, Petition Decision, Dec. 3, 2019, 5 pages.
Pending U.S. Appl. No. 14/808,679, Petition for Priority and Supplemental Response, filed May 8, 2019, 25 pages.
Pending U.S. Appl. No. 14/808,679, Petition Supplement, Sep. 25, 2019, 10 pages.
Pending U.S. Appl. No. 14/808,679, Petition, May 8, 2019, 2 pages.
Pending U.S. Appl. No. 14/808,679, Preliminary Amendment, filed Jul. 27, 2015, 9 pages.
Pending U.S. Appl. No. 14/808,679, RCE filed Apr. 11, 2019, 8 pages.
Pending U.S. Appl. No. 14/808,679, Renewed Petition, filed Oct. 9, 2019, 1 pages.
Pending U.S. Appl. No. 14/808,679, Response to Mar. 19, 2018 Restriction Requirement dated May 21, 2018, 2 pages.
Pending U.S. Appl. No. 14/808,679, Response to Non-Final Office Action dated Jun. 12, 2020, filed Sep. 14, 2020, 9 pages.
Pending U.S. Appl. No. 14/808,679, Response to Sep. 10, 2018 Non-Final Office Action dated Dec. 10, 2018, 9 pages.
Pending U.S. Appl. No. 14/808,679, Second Renewed Petition, filed Oct. 31, 2019, 3 pages.
Pending U.S. Appl. No. 14/808,679, Supplemental Response, dated May 8, 2019, 16 pages.
(Davalos, Rafael et al.) Co-Pending Application No. PCT/US23/15118, filed Mar. 13, 2023, Specification, Claims, Figures.
(Davalos, Rafael V. et al.) Co-Pending U.S. Appl. No. 18/027,824, filed Mar. 22, 2023, Specification, Claims, and Figures.
(Davalos, Rafael V. et al.) Co-Pending U.S. Appl. No. 18/130,330, filed Apr. 3, 2023, Specification, Claims, Figures.
(Garcia, Paulo A. et al.) Co-Pending U.S. Appl. No. 18/100,835, filed Jan. 24, 2023, Specification, Claims, Figures.
(Neal, Robert E. et al.) Co-pending U.S. Appl. No. 18/120,158, filed Mar. 10, 2023, Specification, Claims, Figures.
(Sano, Michael B. et al.) Co-pending U.S. Appl. No. 18/123,719, filed Mar. 20, 2023, Specification, Claims, Figures.
Patent No. JP 7051188, Notice of Reasons for Revocation dated Jan. 30, 2023 (3 pages) with English translation (5 pages).
Pending U.S. Appl. No. 14/686,380, Amendment After Board Decision dated Apr. 3, 2023, 8 pages.
Pending U.S. Appl. No. 14/686,380, Appeal Decision dated Jan. 30, 2023, 15 pages.
Pending U.S. Appl. No. 16/375,878, Non-Final Office Action dated Jan. 23, 2023, 8 pages.
Pending U.S. Appl. No. 16/443,351, Notice of Allowance, dated Dec. 7, 2022, 8 pages.
Pending U.S. Appl. No. 16/747,219, Response to Nov. 10, 2022 Final Office Action, dated Feb. 10, 2023, 6 pages.
Pending U.S. Appl. No. 16/865,031, Non-Final Office Action dated Nov. 28, 2022, 16 pages.
Pending U.S. Appl. No. 16/865,031, Response to Nov. 28, 2022 Non-Final Office Action, dated Feb. 27, 2023, 10 pages.
Pending U.S. Appl. No. 16/865,772, Non-Final Office Action dated Jan. 20, 2023, 17 pages.
Pending U.S. Appl. No. 16/865,772, Response to Aug. 22, 2022 Final Office Action, dated Dec. 22, 2022, 8 pages.
Pending U.S. Appl. No. 17/069,359, Non-Final Office Action dated Nov. 25, 2022, 7 pages.
Pending U.S. Appl. No. 17/069,359, Notice of Allowance dated Apr. 7, 2023, 7 pages.
Pending U.S. Appl. No. 17/069,359, Response to Nov. 25, 2022 Non-Final Office Action, dated Feb. 27, 2023, 7 pages.
Pending U.S. Appl. No. 17/172,731, Non-Final Office Action dated Feb. 15, 2023, 7 pages.
Pending U.S. Appl. No. 18/027,824, Preliminary Amendment dated Mar. 22, 2023, 8 pages.
Pending U.S. Appl. No. 18/100,835, Preliminary Amendment filed Jan. 26, 2023, 8 pages.
Pending U.S. Appl. No. 18/100,835, Second Preliminary Amendment filed Feb. 6, 2023, 6 pages.
Pending U.S. Appl. No. 18/120,158, Preliminary Amendment dated Mar. 13, 2023, 195 pages.
Pending Application No. 19861489.3 Response to May 16, 2022 Extended European Search Report, dated Dec. 13, 2022, 136 pages.
Pending Application No. EP 15793361.5, Communication Pursuant to Article 94(3) EPC, dated Apr. 4, 2023, 4 pages.
U.S. Appl. No. 16/210,771 (U.S. Pat. No. 11,607,537), file history through Dec. 2022, 139 pages.
U.S. Appl. No. 16/535,451 (U.S. Pat. No. 11,453,873), file history through Aug. 2022, 85 pages.
U.S. Appl. No. 16/655,845 (U.S. Pat. No. 11,607,271), file history through Jan. 2023, 68 pages.
(Neal, Robert E et al.) Co-pending U.S. Appl. No. 18/502,967, filed Nov. 6, 2023, Specification, Claims, Figures.
Pending U.S. Appl. No. 17/172,731, Non-Final Office Action dated Oct. 31, 2023, 13 pages.
Pending U.S. Appl. No. 18/348,605, Preliminary Amendment dated Oct. 31, 2023, 7 pages.
Pending U.S. Appl. No. 18/502,967, Preliminary Amendment filed Nov. 6, 2023, 6 pages.
Patent No. JP 7051188, Response to Opposition dated Aug. 22, 2023 (21 pages) with English translation (25 pages).
Pending U.S. Appl. No. 16/375,878, Final Office Action dated Aug. 18, 2023, 11 pages.
Pending U.S. Appl. No. 16/375,878, Response to Aug. 18, 2023 Final Office Action, dated Oct. 18, 2023, 9 pages.
Pending U.S. Appl. No. 16/747,219, Response to May 25, 2023 Non-Final Office Action, dated Aug. 25, 2023, 9 pages.
Pending U.S. Appl. No. 16/865,031, Notice of Allowance dated Oct. 4, 2023, 10 pages.
Pending U.S. Appl. No. 16/865,772, Final Office Action dated Aug. 4, 2023, 19 pages.
Pending U.S. Appl. No. 17/000,049, Restriction Requirement dated Jul. 31, 2023, 6 pages.
Pending U.S. Appl. No. 17/172,731, Response to Jul. 12, 2023 Final Office Action, dated Oct. 12, 2023, 10 pages.
Pending U.S. Appl. No. 17/277,662 Notice of Allowance dated Oct. 2, 2023, 7 pages.
Pending U.S. Appl. No. 17/277,662 Response to May 5, 2023 Non-Final Office Action, dated Aug. 7, 2023, 8 pages.
Pending U.S. Appl. No. 17/338,960, Response to May 24, 2023 Ex Parte Quayle Action, dated Aug. 8, 2023, 6 pages.
Pending U.S. Appl. No. 17/591,992, Preliminary Amendment dated Sep. 20, 2023, 9 pages.
Pending Application No. EP 15793361.5, Response to Apr. 4, 2023 Communication Pursuant to Article 94(3) EPC, dated Oct. 16, 2023, 13 pages.
Pending Application No. PCT/US23/15118, International Search Report and Written Opinion dated Jul. 31, 2023, 18 pages.
Pending U.S. Appl. No. 16/938,778, Restriction Requirement dated Oct. 24, 2023, 6 pages.
(Davalos, Rafael et al.) Co-Pending Application No. PCT/US23/76626, filed Oct. 11, 2023, Specification, Claims, Figures.
(Neal, Robert et al.) Co-pending U.S. Appl. No. 18/528,051, filed Dec. 4, 2023, Specification, Claims, Figures.

(56) References Cited

OTHER PUBLICATIONS

Pending U.S. Appl. No. 16/375,878, Notice of Allowance dated Nov. 15, 2023, 6 pages.
Pending U.S. Appl. No. 16/938,778, Response to Oct. 24, 2023 Restriction Requirement, dated Dec. 13, 2023, 3 pages.
Pending U.S. Appl. No. 17/000,049, Non-Final Office Action dated Dec. 11, 2023, 13 pages.
Pending U.S. Appl. No. 17/000,049, Response to Jul. 31, 2023 Restriction Requirement dated Nov. 9, 2023, 8 pages.
(Davalos, Rafael V. et al.) Co-pending U.S. Appl. No. 18/404,473, filed Jan. 4, 2024, Specification, Claims, Figures.
Pending U.S. Appl. No. 16/938,778, Non-Final Office Action dated Jan. 2, 2024, 12 pages.
Pending U.S. Appl. No. 17/172,731, Response to Oct. 31, 2023 Non-Final Office Action, dated Jan. 31, 2024, 7 pages.
Pending U.S. Appl. No. 17/591,992, Non-Final Office Action dated Feb. 23, 2024, 9 pages.
Pending U.S. Appl. No. 17/591,992, Non-Final Office Action dated Jan. 24, 2024, 7 pages.
Pending Application No. PCT/US23/76626, Invitation to Pay Additional Fees dated Feb. 21, 2024, 2 pages.

\* cited by examiner

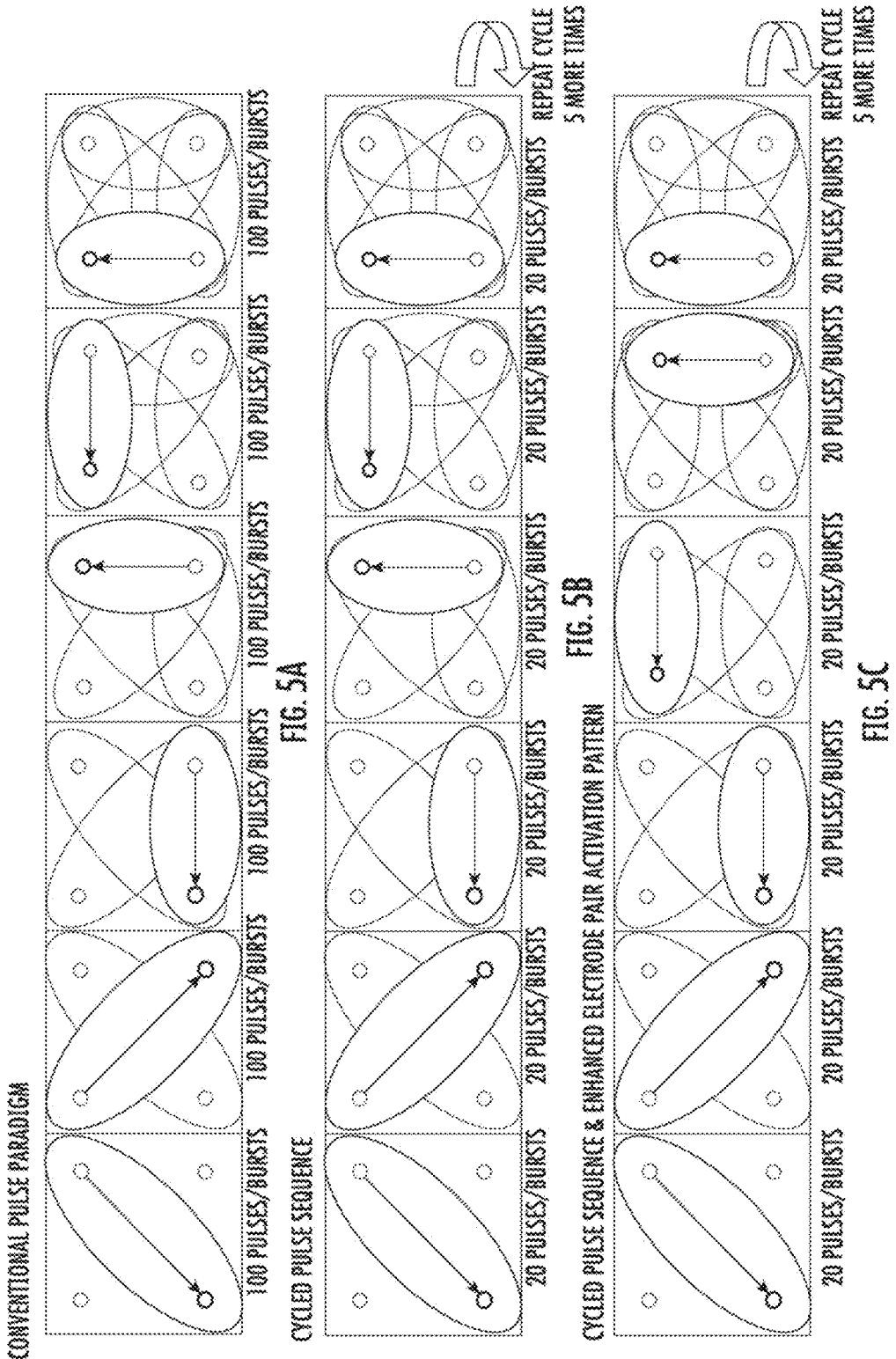

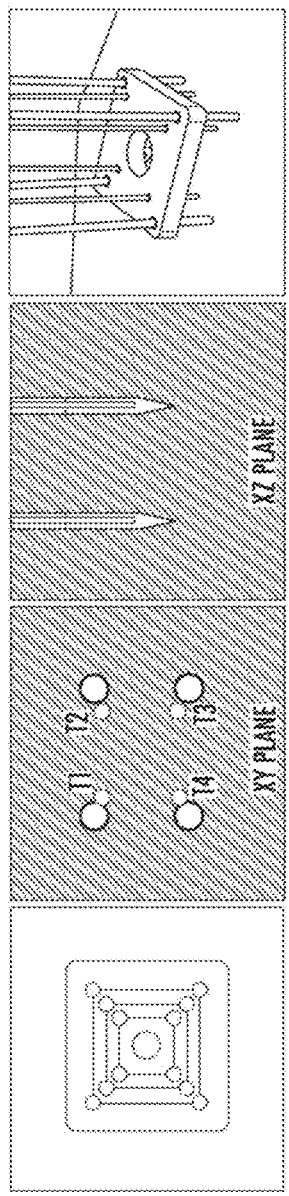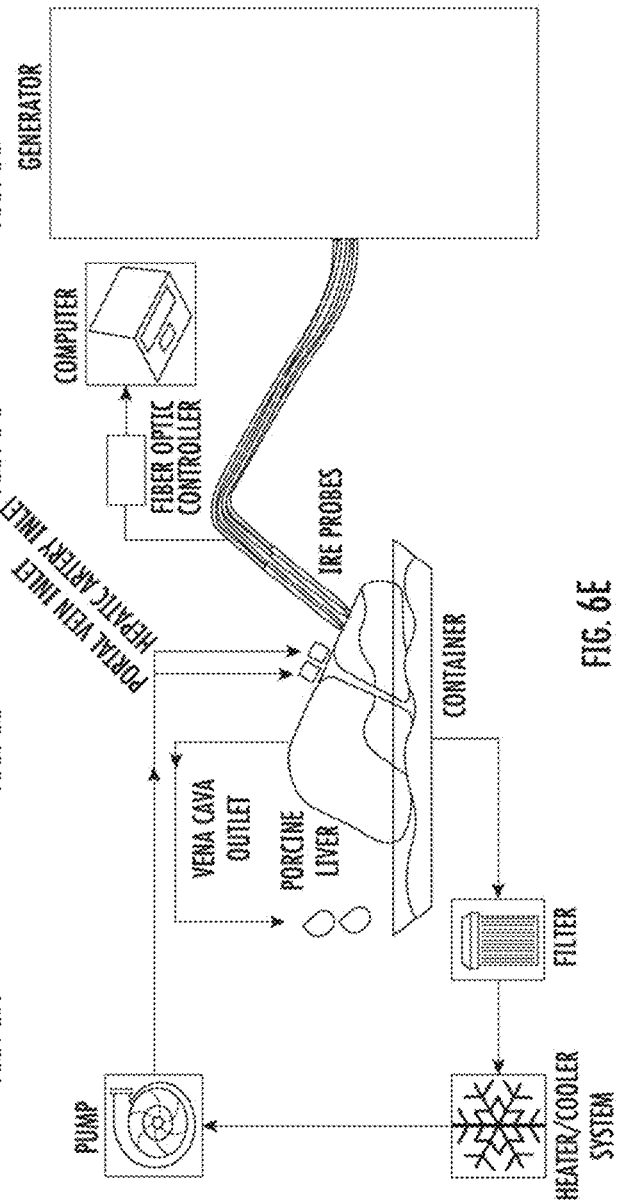
FIG. 6A  FIG. 6B  FIG. 6C  FIG. 6D  FIG. 6E

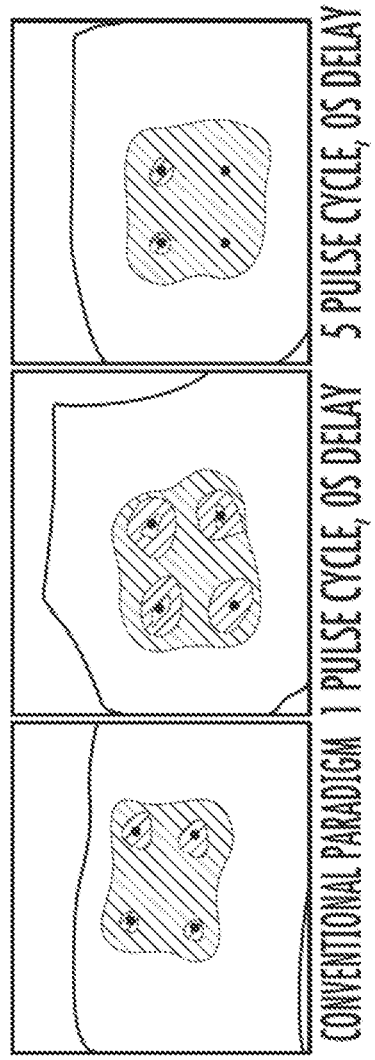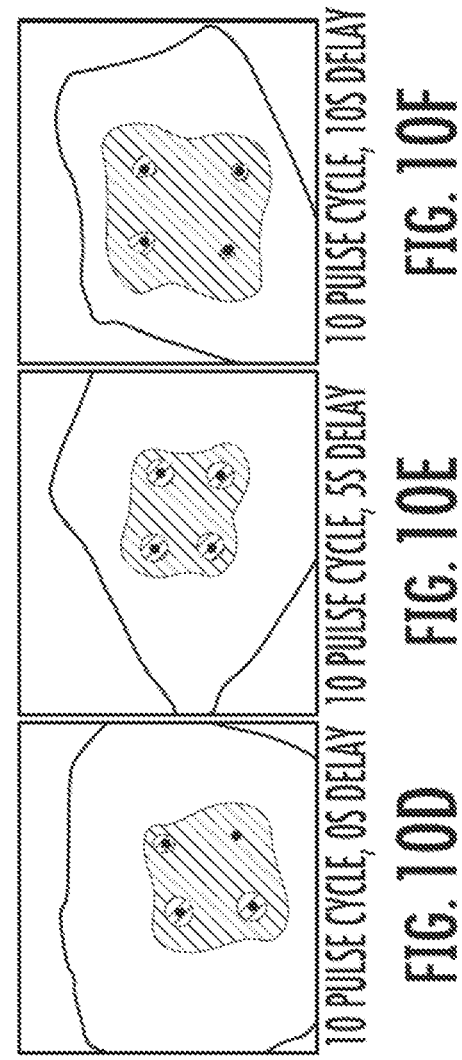
FIG. 10A CONVENTIONAL PARADIGM, 1 PULSE CYCLE, 0S DELAY
FIG. 10B 1 PULSE CYCLE, 0S DELAY
FIG. 10C 5 PULSE CYCLE, 0S DELAY
FIG. 10D 10 PULSE CYCLE, 0S DELAY
FIG. 10E 10 PULSE CYCLE, 5S DELAY
FIG. 10F 10 PULSE CYCLE, 10S DELAY

CYCLED PULSING TO MITIGATE THERMAL DAMAGE FOR MULTI-ELECTRODE IRREVERSIBLE ELECTROPORATION THERAPY

CROSS-REFERENCE TO RELATED APPLICATIONS

The present application relies on the disclosure of and claims priority to and the benefit of the filing date of U.S. Provisional Patent Application No. 62/868,235, filed Jun. 28, 2019 and U.S. Provisional Patent Application No. 62/892,636, filed Aug. 28, 2019, both of which are hereby incorporated by reference in their entireties.

BACKGROUND OF THE INVENTION

Field of the Invention

The present invention is directed to the field of treatment of tissue with electrical energy, such as electroporation, or more particularly, such as irreversible electroporation. Embodiments of the invention provide methods and systems for distributing electrical energy to tissue which minimize Joule heating, thermal effects, and/or thermal damage, without sacrificing efficacy of treatment. Embodiments are particularly suitable to electrical energy-based therapies employing multiple electrodes, such as arrays of electrodes.

Description of Related Art

A variety of electrical energy-based therapies have been developed, including reversible electroporation, electrochemotherapy, electrogenetherapy, supraporation, radiofrequency ablation, irreversible electroporation (IRE) and high frequency irreversible electroporation (HFIRE). It is often desirable to limit tissue hyperthermia during these treatments. While a number of solutions have been proposed, there remains a need for improvements.

SUMMARY OF THE INVENTION

The present inventors have developed systems and methods which distribute an amount of electrical energy to tissue in a manner which minimizes Joule heating to tissue. While various embodiments will be discussed in the foregoing Detailed Description, it should be understood that these are merely provided to illustrate various implementations, of which variations which are encompassed within the principles of the invention may occur to the skilled artisan reading the benefit of this disclosure.

Embodiments of the invention include Aspect 1, which is a method of treating tissue comprising: disposing a number of electrodes in tissue to outline a target region to be treated; optionally selecting a total number of electrical pulses to be delivered to the target region; and delivering a total number of electrical pulses to the target region by: activating a number of pairs of the electrodes in a number of cycles; wherein the activating is performed a number of times that equals the total number of electrical pulses, divided by the number of pairs of electrodes, divided by the number of cycles; whereby electrical energy is strategically distributed to sub-regions within the outline of the target region to treat tissue while mitigating one or more of thermal effects or damage, potential for Joule heating, or delivery of electric current to tissue of the target region.

Aspect 2, is the method of Aspect 1, wherein each pair of electrodes delivers a pulse train with no delay between pulses in the pulse train.

Aspect 3 is the method of Aspect 1 or 2, further comprising adding one or more delay between electrical pulses and/or bursts in a manner to further mitigate one or more of the thermal effects, thermal damage, potential for Joule heating, or delivery of electric current to tissue of the target region.

Aspect 4 is the method of any of Aspects 1-3, wherein the thermal effects or thermal damage are evidenced by an amount of white tissue coagulation.

Aspect 5 is the method of any of Aspects 1-4, wherein a ratio of thermally damaged tissue area to ablation area is less than 5%.

Aspect 6 is the method of any of Aspects 1-5, wherein the number of electrodes is less than the number of pairs of electrodes.

Aspect 7 is the method of any of Aspects 1-6, wherein the activating is performed such that no single electrode is activated more than two consecutive times within a cycle.

Aspect 8 is the method of any of Aspects 1-7, wherein the same and/or different sub-regions of the target region are treated consecutively.

Aspect 9 is the method of any of Aspects 1-8, wherein the activating comprises applying a first pulse train to a first pair of electrodes, applying a second pulse train to a second pair of electrodes, optionally applying additional pulse trains to one or more additional pairs of electrodes, then again applying a pulse train to the first pair of electrodes to start a new cycle, and repeating such activating over the number of cycles until the total number of determined electrical pulses is reached.

Aspect 10 is the method of any of Aspects 1-8, wherein the delivering of the electrical pulses causes electroporation based therapy, electroporation, irreversible electroporation, reversible electroporation, electrochemotherapy, electrogenetherapy, supraporation, and/or high frequency irreversible electroporation, or combinations thereof.

Aspect 11 is the method of any of Aspects 1-10, wherein the delivering causes IRE and/or HFIRE.

Aspect 12 is the method of any of Aspects 1-11, wherein one or more of the following parameters are employed for the delivering of the electrical pulses: a) the number of cycles is from one to ten; b) one or more delays of 0 to 10 seconds each (within a pulse train and/or between activation of pairs and/or between cycles); c) a number of pulses per cycle and/or pulses per pair of 10 to 200; d) a total number of pulses of 100 to 5000; and/or e) a total number of pairs of electrodes of from 3 to 28.

Aspect 13 is the method of any of Aspects 1-12, wherein the delivering is performed: using a voltage ranging from 0 V to 10,000 V; and/or with pulse lengths in the ns to second range; and/or with a frequency in the range of 0 Hz to 100 MHz; and/or with a waveform that is square, triangular, trapezoidal, exponential decay, sawtooth, sinusoidal, and/or alternating polarity; and/or with a total number of pulses ranging from 1-5,000 pulses; and/or with a total number of pulses per pulse train ranging from 1-5,000 pulses.

Aspect 14 is a method of treating a tissue with electrical energy while mitigating thermal damage to the tissue comprising: distributing a total number of electrical pulses to the tissue by way of a plurality of electrode pairs over a plurality of cycles, such that each electrode pair is activated to receive one or more pulse train during each cycle of the plurality of cycles.

Aspect 15 is the method of Aspect 14, wherein each pair of electrodes delivers a pulse train with no delay between pulses in the pulse train.

Aspect 16 is the method of Aspect 14 or 15, further comprising introducing a delay between one or more of the electrical pulses and/or one or more pulse train.

Aspect 17 is an electrical energy based system comprising: an array of three or more electrodes; an electrical pulse generator in operable communication with the electrodes; wherein the electrical pulse generator comprises programming capable of activating a plurality of pairs of electrodes in a manner which distributes an electric field at different spatial coordinates at different times in a manner to mitigate one or more of thermal effects, thermal damage, potential for Joule heating, or delivery of electric current to tissue of the target region.

Aspect 18 is the system of Aspect 17, wherein:
the programming is capable of distributing a total number of pulses over multiple pairs of electrodes,
wherein pairs of electrodes are individually and sequentially activated over multiple cycles such that:
$P_T = (\varepsilon_p)(\bar{P}_\#)(C_\#)$, wherein:
$P_T$=the total number of pulses delivered to tissue;
$\varepsilon_p$=the total number of electrode pair combinations;
$\bar{P}_\#$=the average number of pulses delivered in a pulse train per activated electrode pair per cycle, and
$C_\#$=the total number of cycles.

Aspect 19 is the system of Aspect 17 or 18, wherein the programming is capable of introducing one or more delays between one or more of the electrical pulses.

Aspect 20 is the system of any of Aspects 17-19, wherein the one or more delays are introduced within one or more pulse train applied to each pair, and/or between activation of one or more electrode pair, and/or between one or more of the cycles.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

FIGS. 5A-C are illustrations of pulse delivery methods, where FIG. 5A is an illustration of an exemplary conventional pulse delivery scheme (i.e., non-cycled pulsing) using a conventional EPAP scheme, where 100 pulses were delivered per electrode pair for a total number of 600 pulses to the target tissue. FIG. 5B is an illustration of an embodiment of a cycled pulse paradigm but using the conventional EPAP scheme of FIG. 5A (5 pulse cycle, 0 s delay scheme), where 20 pulses were delivered per electrode pair, yielding 120 total pulses per cycle and, again, a total of 600 pulses to the target region. FIG. 5C is an illustration of an embodiment of the same cycled pulse paradigm shown in FIG. 5B, except that FIG. 5C shows an enhanced electrode pair activation pattern (EPAP), such that no single electrode was activated more than two consecutive times, whereas in FIG. 5B, at least one of the electrodes is activated three times consecutively. Alternatively, instead of pulses, bursts of pulses can be applied, such as instead of 100 pulses, 100 bursts of pulses can be applied, or instead of 20 pulses, 20 bursts of pulses can be applied.

FIG. 6A is a Computer-Aided Design (CAD) rendering of a 4-electrode support device to ensure equidistant spacing throughout each treatment. In embodiments, the electrode spacing of the support device (and thus the spacing of the holes through which the electrodes would pass) can be disposed as shown in FIG. 6A such that the four innermost holes are spaced about 1 cm apart, the four outermost holes are spaced about 2 cm apart, and the four intermediate holes (disposed substantially concentrically between the innermost and outermost holes) are spaced about 1.5 cm apart, with a hole diameter of a size sufficient to accommodate an electrode, such as about 0.24 cm.

FIGS. 6B and 6C are schematic diagrams showing fiber optic thermal sensor placement in the "xy" and "xz" plane, respectively. Each temperature sensor was labeled T1-T4 to understand temperature trends at each electrode.

FIG. 6D is an image showing the implementation of the support devices on the perfused organ model for the 4-monopolar electrode configuration.

FIG. 6E is a schematic diagram of the perfusion, fiber optic thermal measurement, and pulse delivery systems.

FIGS. 10A-F are images showing representative cross-sectional tissue sample images for the conventional paradigm (FIG. 10A), 1 pulse cycle, 0 s delay (FIG. 10B), 5 pulse cycles, 0 s delay (FIG. 10C), 10 pulse cycles, 0 s delay (FIG. 10D), 10 pulse cycles, 5 s delay (FIG. 10E), 10 pulse cycles, 10 s delay (FIG. 10F).

As shown in FIG. 11B, the protocols with a zero second delay displayed shorter treatment times on average than other pulse schemes, the conventional paradigm and "10 pulse cycle, 5 s delay" group were statistically similar, and the treatment time for the "10 pulse cycle, 10 s delay" group was the longest on average.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Definitions:

The term "consecutive" activation of a single electrode refers to activation of a specific electrode during pulse delivery through a first electrode pair, followed by activation of the next electrode pair that includes that same specific electrode. Consecutive activation may also be referred to as sequential activation, and consecutive/sequential activation of a single electrode occurs regardless of direction of energy flow between the electrodes within the electrode pair. Said another way, an electrode is consecutively/sequentially activated if it is an electrode of one activated pair and an electrode of a second activated pair that is activated consecutively/sequentially after the first pair, and whether energy is moving from or to the electrode in either pair.

The term "conventional protocol" refers to a pulse scheme in which all pulses are delivered within a single cycle. All pulses for a specific electrode pair are delivered before the next electrode pair is activated. Typically, to determine the total number of pulses to be delivered for a particular treatment, the desired number of pulses per electrode pair can be determined and multiplied by the total number of electrode pairs. Alternatively or in addition, the number of pulses delivered per electrode pair can be calculated by dividing the total number of desired pulses by the number of electrode pairs to be activated. The term may be used interchangeably with "conventional treatment," "conventional pulsing scheme," "conventional paradigm," "conventional pulse scheme," "conventional pulse paradigm," "conventional pulse protocol," "conventional pulsing sequence," "conventional pulsing paradigm," "conventional sequence," or a pulse scheme may just be labeled as "conventional." For example, a conventional pulse scheme is shown in FIG. 5A.

The term "cycled pulsing scheme" refers to a pulse scheme in which the total number of pulses are delivered over more than one cycle. The total number of pulses per cycle is calculated by dividing the total number of desired pulses by the number of cycles. The term may be used interchangeably with "cycled pulsing protocol," "cycled pulsing sequence," "cycled pulsing," "cycled pulsing paradigm," "cycled pulsing embodiment," "cycled pulse sequencing," "cycled pulse paradigm," or "cycled pulsing pattern." For example, a cycled pulsing scheme is shown in FIGS. 5B and 5C.

Figure 12A:
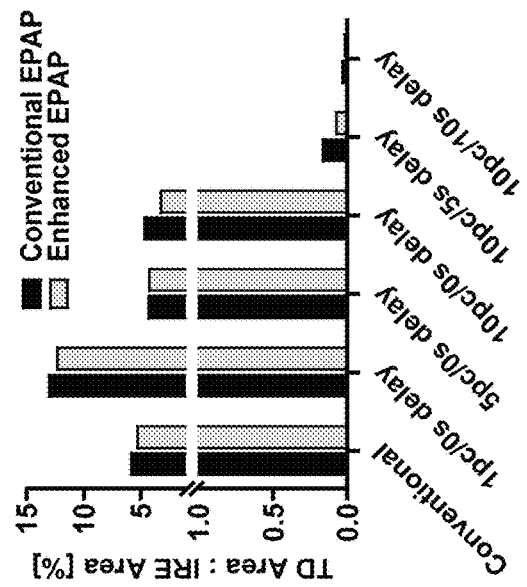
FIGS. 12A-12C are graphs showing numerical modeling data of the area of tissue that experiences an electric field greater than 601 V/cm for the conventional and enhanced electrode pair activation patterns (EPAPs) (FIG. 12A) for the various conventional and cycled pulsing protocols indicated along the X axis, the area of tissue that experiences thermal damage ($\Omega$=2.3) for both EPAPs (FIG. 12B) for these protocols, and the percentage ratio of thermal damage area to IRE treatment zone area (FIG. 12C) for these protocols. The initial temperature within the numerical model was set to $T_o$=30° C. to match the experimental settings.
Figure 12B:
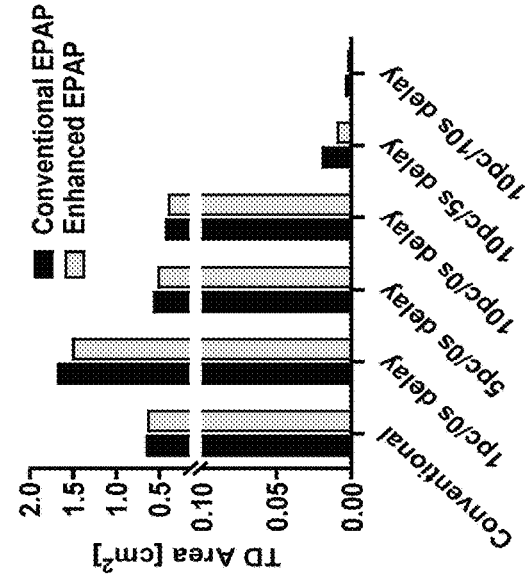
Figure 12C:
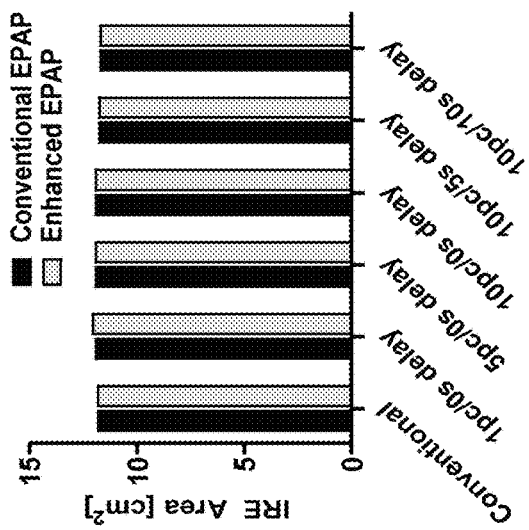

The term "electrode pair activation pattern (EPAP)" refers to the sequence in which electrode pairs are activated within a cycle or across multiple cycles. Each of FIGS. 5A-C shows an EPAP, with FIGS. 5A-B showing conventional EPAP and FIG. 5C showing enhanced EPAP. Further, for example, FIGS. 12A-C show conventional and enhanced EPAP can be used with either or both conventional protocols and cycled pulsing protocols.

The term "conventional EPAP" refers to an electrode pair activation pattern (EPAP) in which pulses are delivered without regard to sequential or consecutive activation of any electrode from one activated electrode pair to the next. With conventional EPAP, an electrode can be activated in a first pair, then the same electrode can be activated again in the next activated pair, and activated again in the next activated pair, such as is shown in FIG. 5A.

The term "enhanced" electrode pair activation pattern (EPAP) refers to an improved electrode pair activation pattern (EPAP) in which sequential or consecutive activation of a single electrode is minimized, as shown in FIG. 5C and FIGS. 12A-C. For example, an electrode is activated in a first pair, then activated in the next activated pair, but is not activated in the next activated pair.

Embodiments of the invention include a method which distributes electrical energy to tissue over geometric space and/or time in a manner which reduces heating, such as Joule heating, of the tissue.

Embodiments also include a method which applies an electric field in a manner that increases the amount of time a quantity of electrical energy is applied to an area or volume of tissue, thereby reducing the concentration of electrical energy applied to the area or volume of tissue per unit time and/or reducing the electric field applied to the area or volume of tissue per unit time.

Advantages resulting from the methods include reduced Joule heating and/or reduced thermal damage to tissue. For example, while the mechanisms for IRE cell death are non-thermal, temperature and electric current variations occur due to high electric field gradients immediately adjacent to the needle electrodes. In one application, the methods are useful for reducing Joule heating and/or thermal damage resulting from irreversible electroporation (IRE).

One embodiment includes a method of treating tissue. The method includes subdividing a total number of multiple electrical pulses to be delivered to tissue, delivering the electrical pulses to the tissue according to the subdividing, and optionally including one or more delay during treatment between one or more of the multiple electrical pulses in a manner to reduce thermal effects or thermal damage, such as white tissue coagulation, and/or to reduce electric current, while maintaining ablation size.

According to embodiments, the total number of electrical pulses is subdivided between a number of electrode pairs and/or subdivided over a number of cycles. Embodiments can also include delays which are added throughout the treatment. The electrical pulses can be of sufficient energy to produce ablation between all electrodes.

Another embodiment includes a method of treating a target region with electrical energy. The method includes disposing one or more electrodes in or near a target region to be treated, and using the electrode(s) to deliver multiple electrical pulses to the target region in a manner such that only some of the electrodes are actively in use at a time. The delivering is performed in a manner to reduce thermal damage and/or to reduce thermal effects and/or to minimize potential for Joule heating and/or to reduce delivery of electric current.

Another embodiment includes a method of treating a target region with electrical energy, where the method includes disposing one or more electrodes in or near a target region to be treated, and delivering multiple electrical pulses to the target region by way of the electrodes in a manner such that the same and/or different areas of the target region are treated consecutively. The delivering is performed in a manner to reduce thermal damage and/or to reduce thermal effects and/or to minimize potential for Joule heating and/or to reduce delivery of electric current.

Another embodiment includes a method of treating a target tissue, the method comprising distributing an amount of electrical energy over a plurality of pairs of electrodes representing different regions of the target tissue over a plurality of cycles in a manner which reduces thermal damage and/or reduces thermal effects and/or minimizes potential for Joule heating and/or reduces an amount of electric current delivered to a region of the target tissue per unit time.

Another embodiment includes a method of treating a tissue with electrical energy while mitigating thermal damage to the tissue. The method includes distributing electrical energy to the tissue over geometric space and time in a manner which reduces an amount of electrical energy a volume of tissue receives per unit time. Distributing electrical energy to the tissue can include activating a plurality of pairs of electrodes implanted within the tissue in a manner which produces a unique electric field distribution in the tissue at different times. Activating a plurality of pairs of electrodes can include applying a first pulse train to a first pair of electrodes, then applying a second pulse train to a second pair of electrodes, and then applying additional pulse trains to one or more additional pairs of electrodes and then again to the first pair of electrodes to start a new cycle, and repeating such activation over cycles until a targeted number of pulses for each pair of electrodes is reached.

Another embodiment includes a method of treating a tissue with electrical energy while mitigating thermal damage to the tissue, where the method includes distributing a total number of pulses to the tissue by way of a plurality of electrode pairs implanted in tissue over a plurality of cycles such that each electrode pair is activated to receive a pulse train over each cycle of the plurality of cycles.

According to embodiments, the total number of pulses is distributed as per Equation 1:

$$P_T = (\varepsilon_p)(\overline{P}_\#)(C_\#) \quad [1]$$

wherein:
$P_T$=the total number of pulses delivered to tissue
$\varepsilon_p$=the total number of electrode pair combinations
$\overline{P}_\#$=the average number of pulses delivered in a pulse train per activated electrode pair per cycle
$C_\#$=the total number of cycles.

The total number of pulses or bursts of pulses applied to tissue can be chosen to deliver a targeted quantity of electrical energy to the tissue. In the Example to follow, a protocol of 600 pulses was chosen. However, it can be appreciated that 600 bursts of pulses could be applied instead, and/or that the number of pulses can be chosen to fit a particular application and/or clinical situation for treating tissue with electrical energy. In embodiments, the total number of pulses or bursts of pulses can range in the hundreds or more, such as one hundred to several hundred (over one thousand), depending on the amount of energy the application or clinical situation requires. For example, for ablation applications, naturally larger tumor masses may require more pulses/bursts than smaller tumor masses. The conductivity of different tissue types, or tumor types, may also dictate the amount of energy and/or number of pulses/bursts delivered. The plurality of electrical pulses can have a total number of pulses, a total number of bursts of pulses, and/or a total number of pulses per burst, ranging from 1-5,000 pulses/bursts, such as from at least 1 up to 3,000 pulses/bursts, or at least 2 up to 2,000 pulses/bursts, or at least 5 up to 1,000 pulses/bursts, or at least 10 up to 500 pulses/bursts, or from 10 to 100 pulses/bursts, such as from 20 to 75 pulses/bursts, or from 30 to 50 pulses/bursts, such as 1, 5, 10, 15, 20, 25, 30, 35, 40, 45, 50, 60, 70, or 90 pulses/bursts, or any range in between any of these ranges or endpoints, including as endpoints any number encompassed thereby. In any embodiment of the cycled pulsing protocols, it would be understood that the number of pulses is at least 2 or more. The electrical pulses and/or bursts and/or electrical energy and/or electric current can be of an intensity or quantity sufficient for ablating tissue, such as ablation by electroporation, such as IRE or HFIRE.

The total number of electrode pair combinations will depend on the number of electrodes chosen to deliver the pulses to the tissue. In the Example to follow, the four electrode array chosen has a total possible number of electrode pair combinations of six. However, it will be appreciated that other variations are possible. For example, a six electrode array will have a total possible number of electrode pair combinations of fifteen. Table 1 below is illustrative.

TABLE 1

| number of electrodes | possible number of pairs |
|---|---|
| 3 | 3 |
| 4 | 6 |
| 5 | 10 |
| 6 | 15 |
| 7 | 21 |
| 8 | 28 |

The number of pairs of electrodes chosen for delivery of the pulses can be less than the possible number of pairs. For example, the geometry of the electrode array chosen by the skilled artisan may cause some electrode pairs to be positioned to close or too far away from each other for practical delivery of electrical energy to tissue. Also, some pairs may be redundant in that they cover substantially the same area or volume of tissue. The geometry of the array and number of electrodes can be chosen based on, for example, the geometry of the targeted tissue area that one of skill in the art wishes to ablate (e.g. the contours of a tumor mass obtained during imaging, the presence of critical structures near the tumor mass, such as blood vessels or nerves). Again, it can be appreciated that larger tumor masses can require larger arrays than smaller masses. The delivering of the electrical pulses is performed such that pairs of electrodes deliver the electrical pulses and/or bursts of pulses in a manner such that an area of the target region bounded by all of the electrodes is subjected to an electrical field. It is important to note that the electrodes can be monopolar or bipolar electrodes. For example, the electrode pair activation patterns as shown in FIGS. 5A-C could be applied using bipolar electrodes and as such FIGS. 5A-C as shown would represent a side view of two probes inserted into tissue, with each probe comprising two bipolar electrodes. In some cases, electrodes on each probe could be activated to treat the area between the probes and/or electrodes on one probe or the other probe could be activated to treat the area along a probe.

Pulse trains can be delivered or distributed amongst the electrode pairs over several cycles. The particular number of pulses for each pair can be chosen according to the skilled artisan's discretion. While in the Example to follow, 20 pulses or bursts per pair was chosen for the cycled pulsing sequence for each pair, the practitioner need not be limited to using the same number of pulses per pair and/or per cycle. For example, he or she may want to deliver more or less energy to different areas of targeted tissue, and/or at different times, and chose the number of pulses accordingly, again based on such potential factors as features of the tumor, the presence or absence of critical structures, tissue conductivities, and so on. The number of pulses or bursts per pair and number of cycles can be chosen to distribute the total amount of energy chosen (e.g. as total number of pulses) over the geometric area chosen (e.g. size of the electrode array) in a time frame adequate to the application or clinical situation. For example, the number of pulses or bursts for each pair can be in the range of 1 to 100, and the number of cycles can be 1, 2, 3, 4, 5, 6, 7, 8, 9, 10, 11, 12, 13, 14, 15, 16, 17, 18, 19, 20 or more.

The number of pulses and cycles can be chosen to minimize thermal damage delivered during the delivery of electrical energy to tissue. Another advantage of the inventive protocols, and in particular balancing the distribution of pulses/bursts over the treatment area and over the time of the treatment, is a favorable immune response as a result of the ablation (such as IRE) in contrast with treatments using thermal ablation techniques. It has been found that the non-thermal nature of IRE encourages a unique immune response compared to other ablative technologies. For example, it has been shown that IRE could trigger as much as 2-3 times the amount of T cell proliferation in comparison to thermal therapies. SHAO, Qi et al., Engineering T cell response to cancer antigens by choice of focal therapeutic conditions, International Journal of Hyperthermia, 2019, DOI:10.1080/02656736.2018.1539253. Benefits further include the ability for the practitioner to dispose electrodes/probes closer to critical structures without damaging those structures or causing very little damage to such structures. In treating tumors that are disposed close to critical structures, any distance closer to the structure helps and can lead to better treatment results for the patient, in being able to treat tumors in their entirety instead of only partially, which would be a common result of treating in a manner to avoid damaging nearby critical structures. Another benefit of the inventive pulse/burst protocols is in being able to minimize treatment times. The treatment duration can be less than 1 hour, such as less than any of 45 min., 30 min., 15 min., 10 min., or 5 min., such as less than about 7-17 min., wherein the treatment duration is calculated including or not including any delay.

According to embodiments, the order that pairs of electrodes are activated can be the same over each of the cycles, or can be altered from cycle to cycle or for two or more cycles. Further, the order in which electrode pairs are activated can be adjusted to minimize consecutive electrode activation. For example, the order of electrode pair activation can be adjusted such that no single electrode is activated more than two consecutive times. Such order can be implemented with other features of the pulsing protocol to minimize Joule heating.

According to any embodiment, each pair of electrodes can be activated by a pulse train with no delay between pulses in the pulse train. In other embodiments, one or more delays can be introduced, such as a delay between one or more pulses in the pulse train, and/or a delay between the activation of one or more pair of electrodes, and/or a delay between one or more of the cycles. The delay can be on the order of microseconds or seconds, such as one to one thousand microseconds, such as 1, 2, 3, 4, 5, 6, 7, 8, 9, 10, 15, 20, 25, 30, 35, 40, 45, 50, 75, 100, 150, 200, 250, 300, 350, 400, 450, 500, 600, 700, 800, 900, or 1000 microseconds or one to several seconds such as 1, 1.5, 2, 2.5, 3. 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 24, 26, 28, 30 seconds or more. Cumulatively, the one or more delays may be on the order of seconds or minutes.

According to embodiments, the methods treat a target region or tissue with electrical energy in order to ablate cells in the target region or tissue. The target region or tissue can include cancer or non-cancer cells or both. As used herein "cancer" can refer to one or more types of cancer including, but not limited to, acute lymphoblastic leukemia, acute myeloid leukemia, adrenocortical carcinoma, Kaposi Sarcoma, AIDS-related lymphoma, primary central nervous system (CNS) lymphoma, anal cancer, appendix cancer, astrocytomas, atypical teratoid/Rhabdoid tumors, basal cell carcinoma of the skin, bile duct cancer, bladder cancer, bone cancer (including but not limited to Ewing Sarcoma, osteosarcomas, and malignant fibrous histiocytoma), brain tumors, breast cancer, bronchial tumors, Burkitt lymphoma, carcinoid tumor, cardiac tumors, germ cell tumors, embryonal tumors, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-Cell lymphoma, ductal carcinoma in situ, endometrial cancer, ependymoma, esophageal cancer, esthesioneuroblastoma, extracranial germ cell tumor, extragonadal germ cell tumor, eye cancer (including, but not limited to, intraocular melanoma and retinoblastoma), fallopian tube cancer, gallbladder cancer, gastric cancer, gastrointestinal carcinoid tumor, gastrointestinal stromal tumors, central nervous system germ cell tumors, extracranial germ cell tumors, extragonadal germ cell tumors, ovarian germ cell tumors, testicular cancer, gestational trophoblastic disease, hairy cell leukemia, head and neck cancers, hepatocellular (liver) cancer, Langerhans cell histiocytosis, Hodgkin lymphoma, hypopharyngeal cancer, islet cell tumors, pancreatic neuroendocrine tumors, kidney (renal cell) cancer, laryngeal cancer, leukemia, lip cancer, oral cancer, lung cancer (non-small cell and small cell), lymphoma, melanoma, Merkel cell carcinoma, mesothelioma, metastatic squamous cell neck cancer, midline tract carcinoma with and without NUT gene changes, multiple endocrine neoplasia syndromes, multiple myeloma, plasma cell neoplasms, mycosis fungoides, myelodysplastic syndromes, myelodysplastic/myeloproliferative neoplasms, chronic myelogenous leukemia, nasal cancer, sinus cancer, non-Hodgkin lymphoma, pancreatic cancer, paraganglioma, paranasal sinus cancer, parathyroid cancer, penile cancer, pharyngeal cancer, pheochromocytoma, pituitary cancer, peritoneal cancer, prostate cancer, rectal cancer, Rhabdomyosarcoma, salivary gland cancer, uterine sarcoma, Sézary syndrome, skin cancer, small intestine cancer, large intestine cancer (colon cancer), soft tissue sarcoma, T-cell lymphoma, throat cancer, oropharyngeal cancer, nasopharyngeal cancer, hypopharyngeal cancer, thymoma, thymic carcinoma, thyroid cancer, transitional cell cancer of the renal pelvis and ureter, urethral cancer, uterine cancer, vaginal cancer, cervical cancer, vascular tumors and cancer, vulvar cancer, and Wilms Tumor. Benign or non-cancerous tumors or growths for example can include fibroids or fibromas such as uterine fibroids, adenomas such as polyps, lipomas, myomas, nevi or moles, or growth due to benign prostate hyperplasia (BPH), myxoma, papillary fibroelastomas, rhabdomyomas, hemangiomas, teratomas, paragangliomas, cysts such as pericardial cysts or ovarian cysts, warts, endometriosis, and including any abnormal or undesired growth. Other conditions that can be treated using embodiments of the invention include treatment of cardiac arterial fibrillation and fat removal. In one embodiment, the target region or tissue is a solid tumor.

According to embodiments, methods of treating a target region or tissue with electrical energy which distribute that energy cyclically over geometric space and time in the manner described herein can be used to non-thermally ablate cancer cells while minimizing thermal damage to the target region and surrounding tissue. According to embodiments, the ratio of thermally damaged tissue area and ablation area is less than any of 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, 0.5% or 0.1%. This area is typically localized to the immediate area surrounding the electrodes, and in cases where electrode cooling is used, to the immediate area surrounding the cooling zone.

Thermal damage can be measured, for example, as an amount of white tissue coagulation, or an area of white tissue coagulation. Thermal damage can be measured by the amount of denaturization (e.g., protein denaturization or loss of extracellular matrix integrity). Higher levels of thermal damage include protein coagulation, tissue desiccation, and tissue vaporization. Thermal damage can also be measured indirectly, such as with one or more thermal sensor, such as measuring temperature of tissue, electrodes, and/or a region of tissue-electrode interface. According to one embodiment, one or more fiber optic thermal sensor is used to measure temperature. Thermal damage can also be measured by other means, such as by way of biomarkers (e.g. expression of heat shock proteins or heat shock protein genes). The area in which the onset of thermal damage occurs can be defined by $\Omega=2.3$. Thermal damage is a metric of temperature and time and is typically quantitated using an Arrhenius equation or a dose calculation (CEM43). Typically, 43° C. is a commonly used value by those of skill in the art to illustrate the onset of thermal damage over 1 hour (albeit for skin burns).

The non-thermal ablation can occur by way of irreversible electroporation (IRE) and/or high frequency irreversible electroporation (HFIRE). While the following discussion is limited to IRE and HFIRE, it is contemplated that the principles of the invention can apply to other applications of delivering electrical energy to tissue, including electrical pulses capable of reversible electroporation, electrochemotherapy, electrogenetherapy, supraporation, or combinations thereof, such as by way of a DC current or AC current. Parameters for these applications are available in the literature.

Parameters which are effective for IRE and/or HFIRE can include the use of two or more electrodes or energized surfaces (e.g., two or more electrodes disposed in contact with one or the other tissue region, or two or more electrodes disposed in each or both), and from any number of electrodes or energized surfaces, such as 1, 2, 3, 4, 5, 6, 7, 8, 9, 10, 11, 12, 13, 14, 15, 16, 17, 18, 19, or 20 electrodes or energized surfaces and in any configuration relative to one another, such as being delivered by one or more pairs and/or delivered by one or more monopolar probe, one or more bipolar probe, or plate electrodes, such as three or more plate electrodes. The electrodes can also be positioned on flexible medical devices, such as catheters, endoscopes, bronchoscope tools, etc. The electrodes can be spaced apart in pairs such as electrodes spaced from 0 cm to 10 cm apart, such as from above 0 cm up to 10 cm apart, or from 0.2 cm to 9 cm, such as from 0.5 cm to 5 cm, or from 1 cm to 4 cm apart, or from 2 cm to 3 cm, or 1.5 cm, or any range in between any of these ranges or endpoints, including as endpoints any number encompassed thereby.

The electrodes can be needle electrodes, plate electrodes, blunt tip electrodes or combinations thereof. The electrodes can have a length (whether the length of the active tip of the electrode or the shaft of the probe) ranging from 1 cm to 30 cm, such as from 10 cm to 20 cm, or from 5 cm to 15 cm, and/or with a length of the active portion of the probe (e.g., energizable region) ranging from 0.5 cm to 10 cm, such as from 1 cm to 5 cm, or up to 3 cm or up to 4 cm, or any range in between any of these ranges or endpoints, including as endpoints any number encompassed thereby.

The delivering of pulses can be performed using a voltage for the plurality of electrical pulses of 0 V to 10,000 V, such as above 0 V or 1 V up to 10,000 V, and/or from 500 V up to 3,000 V, and/or from 1,000 V up to 2,000 V, such as up to 250 V, up to 300 V, up to 350 V, up to 600 V, up to 650 V, up to 800 V, up to 1,200 V, up to 1,500 V, up to 5,000 V, up to 7,500 V, or any range in between any of these ranges or endpoints, including as endpoints any number encompassed thereby.

The electrical pulses have a pulse length in the picosecond to second range, such as in the nanosecond to ms range, such as from 1 picosecond to 100 microseconds, or from 1 picosecond to 10 microseconds, or from 1 picosecond to 1 microsecond, or from at least 0.1 microsecond up to 1 second, or from 0.5 microseconds up to 10 microseconds, or up to 20 microseconds, or up to 50 microseconds, such as 15, 25, 30, 35, 40, 55, 60, 75, 80, 90, 110, or 200 microseconds, or any range in between any of these ranges or endpoints, including as endpoints any number encompassed thereby.

The plurality of electrical pulses can have a frequency in the range of 0 Hz to 100 MHz, such as from above 0 Hz or 1 Hz up to 100 MHz. IRE pulses can have frequencies in the Hz range, such as from 2 Hz to 100 Hz, or from 3 Hz to 80 Hz, or from 4 Hz to 75 Hz, or from 15 Hz to 80 Hz, or from 20 Hz up to 60 Hz, or from 25 Hz to 33 Hz, or from 30 Hz to 55 Hz, or from 35 Hz to 40 Hz, or from 28 Hz to 52 Hz, or any range in between any of these ranges or endpoints, including as endpoints any number encompassed thereby. HFIRE pulses can have frequencies in the kHz to tens or hundreds of kHz to several MHz range, such as from 1 kHz to 10 kHz, or from 2 kHz to 8 kHz, or from 3 kHz to 5 kHz, or from 4 kHz to 15 kHz, or from 6 kHz to 20 kHz, or from 12 kHz to 30 kHz, or from 25 kHz to 40 kHz, or from 5 kHz to 55 kHz, or from 50 kHz to 2 MHz, including any range in between, such as from 75 kHz to 150 kHz, or from 100 kHz to 175 kHz, or from 200 kHz to 250 kHz, or from 225 kHz to 500 kHz, or from 250 kHz to 750 kHz, or from 500 kHz to 1 MHz, or any range in between any of these ranges or endpoints, including as endpoints any number encompassed thereby. HFIRE is described in U.S. Pat. Nos. 10,292,755 and 10,448,989, which are incorporated herein in their entireties.

The plurality of electrical pulses can have a waveform that is square, triangular, trapezoidal, exponential decay, sawtooth, sinusoidal, bipolar and/or alternating polarity.

According to one embodiment, one or more of the following parameters are employed for the delivering of the electrical pulses:

a) a number of cycles from one to ten (e.g., where one cycle comprises activating all possible electrode pair combinations at least once, or activating a select group of the electrode pair combinations, or sequentially activating all or less than all of the possible pair combinations);

b) one or more delays of 0 to 10 seconds each (within a pulse train and/or between activation of pairs and/or between cycles);

c) a number of pulses per cycle and/or pulses per pair of 10 to 200;

d) a total number of pulses of 100 to 5000; and/or e) a total number of electrode pair combinations of 1 to 30.

Systems

Embodiments of the invention include systems capable of performing one or more methods described herein, or one or more portions thereof. The systems can have therapeutic or diagnostic utilities or applications, or combinations thereof, according to various implementations. Therapeutic applications include ablating, such as substantial non-thermal ablating, one or more tumor or portion thereof. Diagnostic applications include determining the presence of thermal damage, an area or volume of thermal damage, or a probability of thermal damage.

An embodiment of an ablation system includes at least a first and second electrode, a voltage generator programmed to generate a plurality of electrical pulses between the first and second electrodes in a manner which causes non-thermal ablation of cells of one or more tissue, a memory, and a processor. The ablation system can include multiple electrodes such as an array of electrodes implemented with a support capable of positioning the electrodes of the array at predetermined distances from each other. The ablation system can also include one or more thermal sensor, such as a fiber optic thermal sensor, disposed on, within, or adjacent to the electrodes. The ablation system can also include one or more optical imaging system capable of measuring thermal damage, such as white tissue coagulation.

An embodiment includes an electrical energy-based system which includes an array of three or more electrodes and an electrical pulse generator in operable communication with the electrodes. The electrical pulse generator includes programming capable of distributing a total number of electrical pulses or bursts to a target tissue in a manner which reduces thermal damage and/or reduces thermal effects and/or minimizes potential for Joule heating and/or reduces delivery of electric current per unit time. The system's programming is capable of activating a plurality of pairs of electrodes in a manner which distributes an electric field at different spatial coordinates at different times. The programming is capable of applying a pulse train of a predetermined number of pulses or bursts to one pair of electrodes at a time during the activating. The programming is capable of distributing the total number of pulses over multiple pairs, wherein each pair is individually activated by a pulse train, and pairs are activated over multiple cycles such as according to Equation 1. The programming is capable of introducing one or more delays between one or more of the pulses, such as within one or more pulse train applied to each pair, and/or between the activation of one or more electrode pair, and/or between one or more of the cycles. In embodiments, the programming can be pre-programmed and/or a user/practitioner can input certain parameters, such as the number of pulses/bursts and/or number of cycles.

Figure 1:
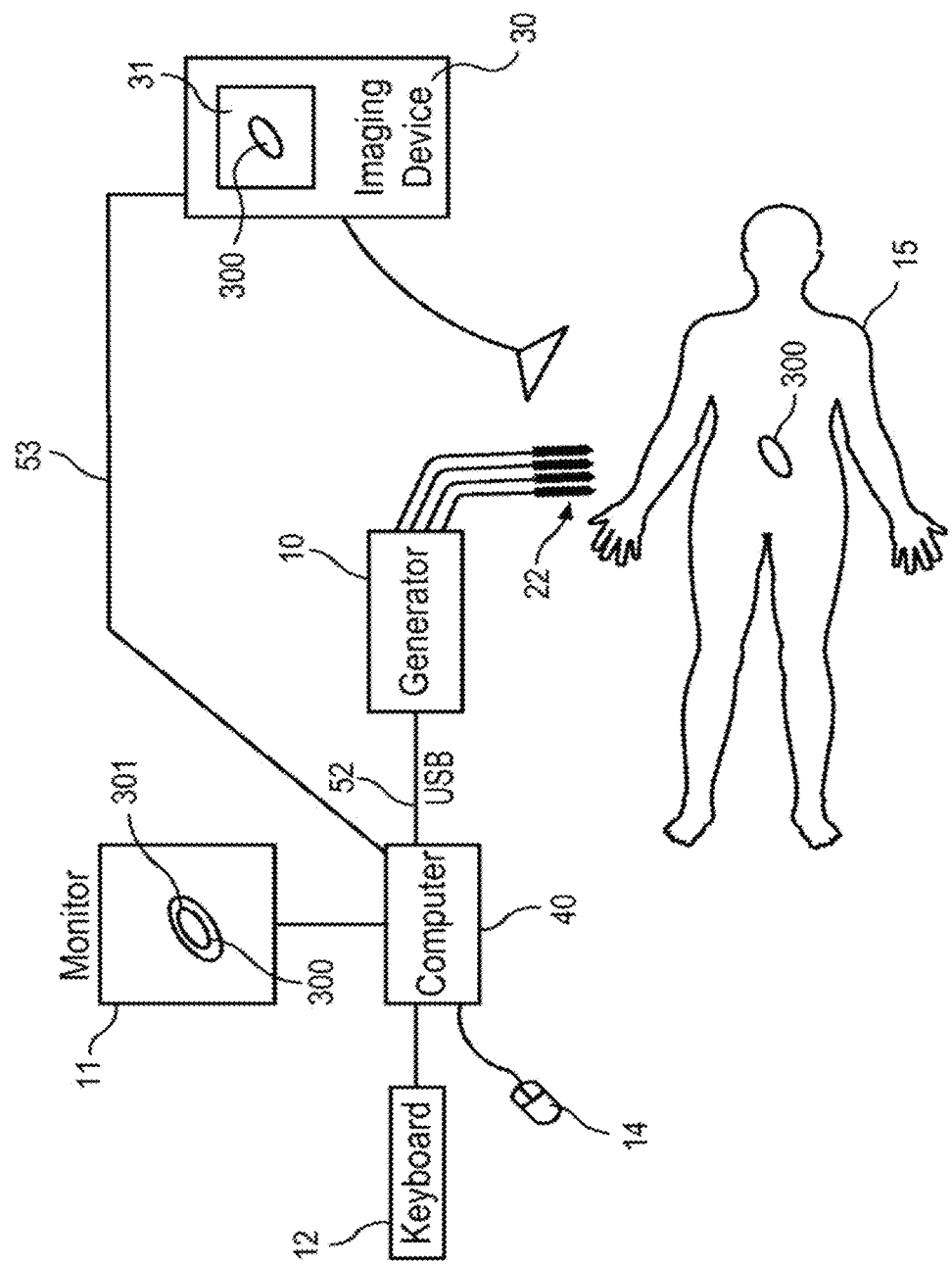
FIG. 1 is a block diagram of an electroporation device according to one aspect of the present invention.

A system embodiment which is capable of executing any method described herein or portion thereof is illustrated in FIG. 1. One or more electrodes/probes 22 deliver therapeutic energy and are powered by a voltage pulse generator 10 that generates high voltage pulses as therapeutic energy such as pulses capable of ablating (e.g. irreversibly electroporating) the tissue cells. The voltage pulse generator 10 can include one or more and any number of receptacles for receiving up to a desired number of individual probes 22 which are adapted to be plugged into the respective receptacle.

Each probe 22 can include one or more monopolar electrode, one or more bipolar electrode having at least two electrodes (electrode conducting regions) separated by an insulating sleeve, multipolar electrodes having greater than two electrode surfaces separated by one or more insulating sleeves which can be energized simultaneously or at different times, plate electrodes with multiple surface electrodes, and/or a grounding pad. In one embodiment, if the probe includes a monopolar electrode, the amount of exposure of the active portion of the electrode can be adjusted by retracting or advancing an insulating sleeve relative to the electrode. See, for example, U.S. Pat. No. 7,344,533, which is incorporated by reference herein in its entirety. In other embodiments, such as when grounding pads are used, the energy can be distributed/alternated between them. For example, any number of grounding pads can be used to mitigate heat accumulating on any one particular grounding pad. In the embodiment shown, the probes 22 are monopolar electrodes. The generator 10 is connected to a treatment control computer 40 having input devices such as keyboard 12 and a pointing device 14, and an output device such as a display device 11 for viewing an image of a target treatment area such as a lesion 300 surrounded by a safety margin 301. The communications connections can be wired or wireless. The therapeutic energy delivery device 20 is used to treat a lesion 300 inside a patient 15. An imaging device 30 includes a monitor 31 for viewing the lesion 300 inside the patient 15 in real time. Examples of imaging devices 30 include ultrasonic, CT, MRI, PET, and fluoroscopic devices as are known in the art. The imaging device 30 can also be a camera capable of capturing digital images, microscopic images, and the like.

For purposes of this application, the terms "code", "software", "program", "programming", "application", "software code", "software module", "module", "program module", and "software program" are used interchangeably to mean software instructions that are executable by a processor. The computer-executable instructions may be organized into routines, subroutines, procedures, objects, methods, functions, or any other organization of computer-executable instructions that is known or becomes known to a skilled artisan in light of this disclosure, where the computer-executable instructions are configured to direct a computer or other data processing device to perform one or more of the specified methods, processes and operations described herein. The computer-executable instructions may be written in any suitable programming language, non-limiting examples of which include C, C++, C#, Objective C, Swift, Ruby/Ruby on Rails, Visual Basic, Java, Python, Perl, PHP, MATLAB and JavaScript.

The "user" of the system can be a physician, a practitioner, or other medical professional. The treatment control module 54 (FIG. 2) executed by a processor outputs various data including text and graphical data to the monitor 11 associated with the generator 10.

Figure 2:
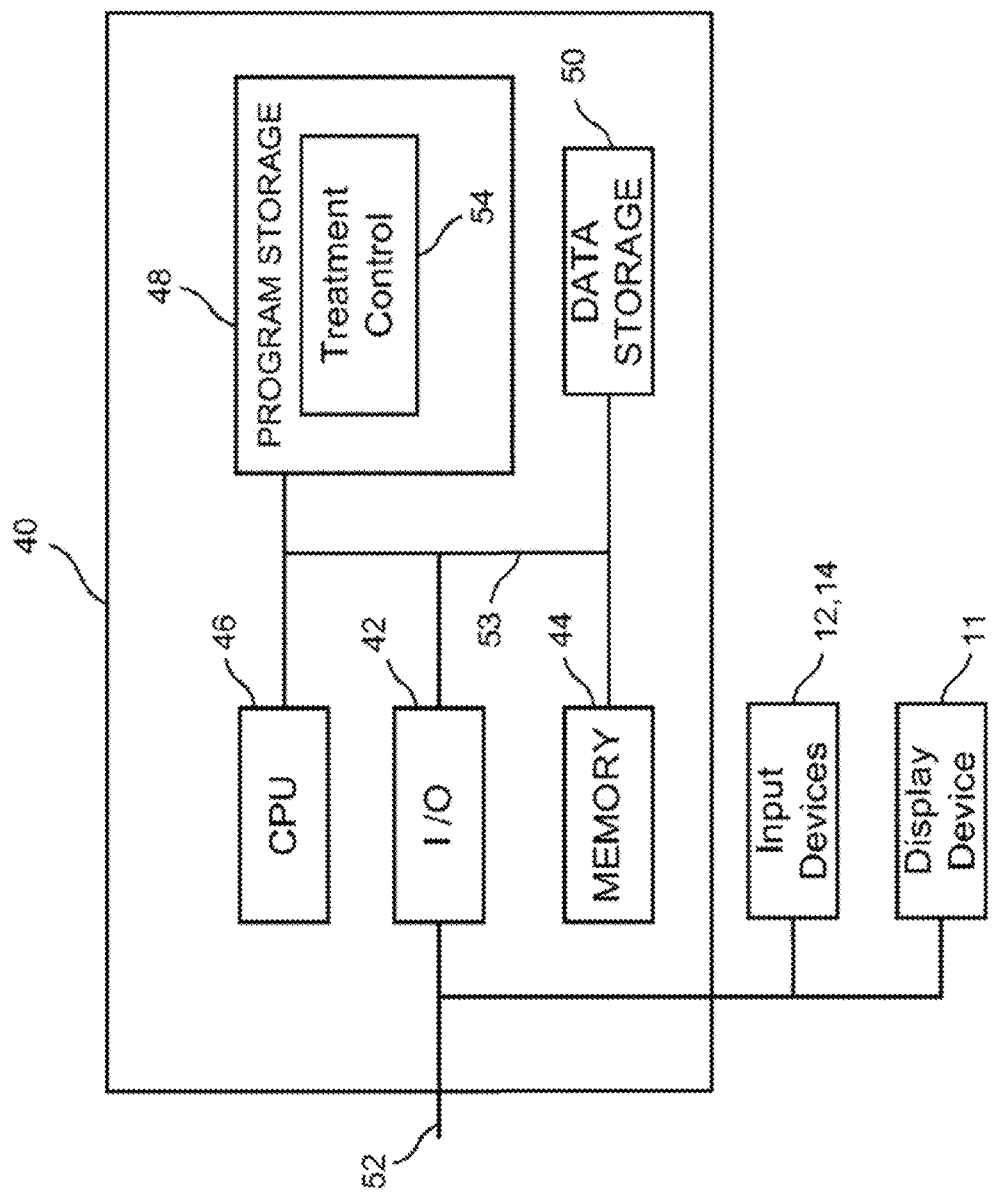
FIG. 2 is a block diagram of a treatment control computer of FIG. 1.

Referring now to FIG. 2, the treatment control computer 40 of the present invention is connected to the communication link 52 through an I/O interface 42 such as a USB (universal serial bus) interface, which receives information from and sends information over the communication link 52 to the voltage generator 10. The computer 40 includes memory storage 44 such as RAM, processor (CPU) 46, program storage 48 such as ROM or EEPROM, and data storage 50, such as hard disk, all commonly connected to each other through a bus 53. As used herein, "memory storage", "program storage", and "data storage" are interchangeable with "non-transitory computer readable storage medium". Program storage 48 stores, among others, computer software (treatment control module 54) or programming which assists a user/physician to plan for, execute, and review the results of a medical treatment procedure, and execute any of the methods described herein. The treatment control module 54, executed by the processor 46, assists a user to plan for a medical treatment procedure by enabling a user to more accurately position each of the probes 22 of the therapeutic energy delivery device 20 in relation to the lesion 300 in a way that will generate the most effective treatment zone. The treatment control module 54 can display the anticipated treatment zone based on the position of the probes and the treatment parameters.

Using any of the methods described herein, the treatment control module 54 can determine/administer a protocol which distributes a total number of pulses (chosen and inputted by a user, or calculated by the treatment planning module) of administered electrical energy to different pairs of the electrodes over a plurality of cycles in a manner which minimizes Joule heating and resulting thermal damage. The treatment control module 54 can also introduce delays in the pulsing protocol to minimize Joule heating, such as a delay within one or more pulse train applied to an electrode pair, and/or a delay between activation of one or more electrode pairs, and/or a delay between one or more cycles. Further, using any of the methods described herein, the treatment control module can alternatively allow a user to manually input a protocol, or any number of one or more parameters, which distributes a total number of pulses of administered electrical energy to different pairs of the electrodes over a plurality of cycles, and/or includes one or more delays between pulse administration. Based on the parameters entered by the user, the treatment control module can then calculate an area of anticipated thermal damage, an anticipated area of non-thermal ablation, and display a visualization of these areas to the user, as well as display an estimate of the ratio of anticipated thermal damage to non-thermal ablation, such as on the monitor or display device 11. The displays can be made available in real-time, for example, to make real-time temperature changes available on screen. Additionally, the treatment control module can modify protocols (whether determined manually by the user or determined by the treatment control module) based on heat received from the thermal sensors, or other feedback, such as imaging of thermal damage. The treatment control module can also display the progress of the treatment in real time and can display the results of the treatment procedure after it is completed. This information can be used to determine whether the treatment was successful and whether it is necessary to re-treat the patient.

The module 54 is also adapted to monitor and display the progress of the electroporation procedure and to determine a successful end point based on the electrical properties of the tissue prior to and during the treatment procedure as explained in more detail in U.S. Patent Application Publication No. 20190175248A1, which is incorporated by reference herein in its entirety. Being able to in real-time monitor and see the end point of the treatment procedure is a huge advantage over the current method in which the physician is performing the treatment essentially blindly without having any idea about whether the treatment is progressing or at what point the treatment procedure is finished.

The program storage 48 stores various electrical threshold values that are used to monitor the treatment procedure. When the programmed sequence of pulses has been delivered and the end point of the procedure has not been reached, the user interface portion of the control module 54 retrieves the recommended parameter changes from the database and presents them to the user through the display 11. The treatment control module 54 can also change the threshold values for determining the progress and the end point of the procedure based on initial treatment pulse parameters programmed by the user. A user can manually input the various thresholds for different tissue types or the system can have these thresholds stored electronically.

Alternatively, the treatment control module 54 can also automatically derive or adjust the threshold values for determining the progress and the end point of the procedure based on test signals (e.g., AC test signals) that are applied and determining electrical properties of the cells such as impedance values or current values. The control module 54 may then store the changed threshold values in the program storage 48 for later use as the new criteria for comparison.

Further, AC intra-treatment test signals may continue to be delivered in addition to the comparative DC intra-treatment test signals. By tracking the change in impedance for the AC-signal, the treatment control module 54 determines and factors out the effects on impedance occurring due to temperature rise. This enables more accurately tracking changes in the real-part of the impedance by reflecting changes encountered solely due to persistent electroporated cells. A more detailed discussion of the control module 54 is made in U.S. Patent Application Publication No. 20190175248A1, which is incorporated by reference herein in its entirety.

Any of the software program modules in the program storage 48 and data from the data storage 50 can be transferred to the memory 44 as needed and is executed by the CPU 46.

In one embodiment, the computer 40 is built into the voltage generator 10. In another embodiment, the computer 40 is a separate unit which is connected to the voltage generator through the communications link 52. The communication link 52 can be, for example, a USB link.

In one embodiment, the imaging device 30 is a stand-alone device which is not connected to the computer 40. In the embodiment as shown in FIG. 1, the computer 40 is connected to the imaging device 30 through a communications link 53. As shown, the communication link 53 is a USB link. In this embodiment, the lesion image generated by the imaging device 30 can be directly displayed on the monitor 11 of the computer running the treatment control module 54. The image data from the imaging device 30 can also be used to capture information during and/or after treatment of the lesion 300, such as an area of ablation and/or an area of thermal damage.

It should be noted that the software can be used independently of the generator 10. For example, the user can plan the treatment in a different computer as will be explained below and then save the treatment parameters to an external memory device, such as a USB flash drive (not shown). The data from the memory device relating to the treatment parameters can then be downloaded into the computer 40 to be used with the generator 10 for treatment.

Figure 3:
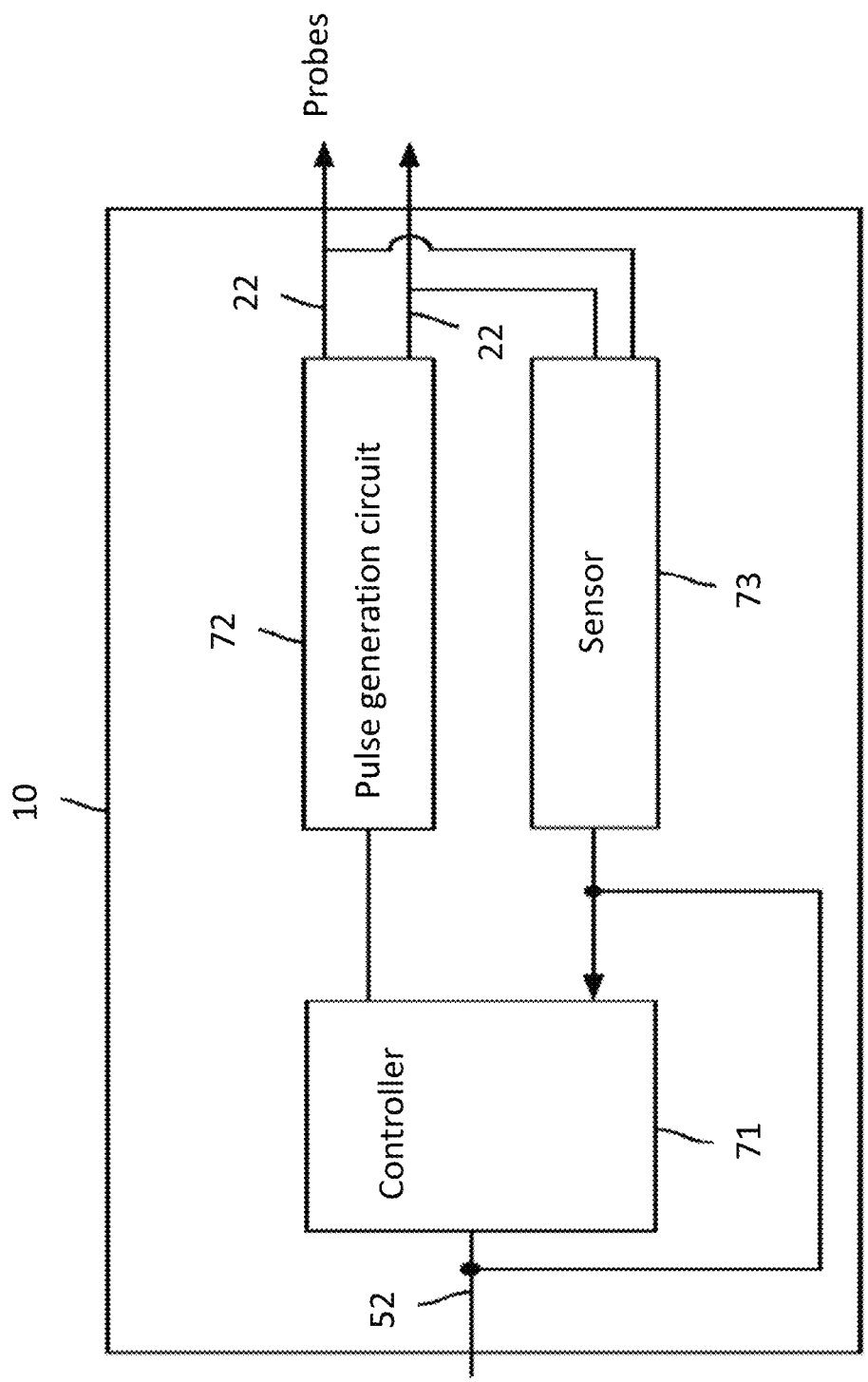
FIG. 3 is a block diagram of a pulse generator shown in FIG. 1.

FIG. 3 is a functional block diagram of a pulse generator 10 shown in FIG. 1. FIG. 2 illustrates one embodiment of a circuitry to monitor the progress of and determine an end point of the treatment procedure. A USB connection 52 carries instructions from the user computer 40 to a controller 71. The controller 71 can be a computer similar to the computer 40 as shown in FIG. 2. The controller 71 can include a processor, ASIC (application-specific integrated circuit), microcontroller or wired logic. The controller 71 then sends the instructions to a pulse generation circuit 72. The pulse generation circuit 72 generates the pulses and sends electrical energy to the probes. For clarity, only one pair of probes/electrodes is shown. However, the generator 10 can accommodate any number of probes/electrodes such as 1 probe, 2 probes, 3 probes, 4 probes, 5 probes, 6 probes, 7 probes, 8 probes, 9 probes, 10 probes, 11 probes, 12 probes, 13 probes, 14 probes, 15 probes, 16 probes, 17 probes, 18 probes, 19 probes, 20 probes, or more. In the embodiment shown, the pulses are applied one pair of electrodes at a time, and then switched to another pair. The pulse generation circuit 72 includes a switch, preferably an electronic switch that switches the probe pairs based on the instructions received from controller 71.

A sensor 73 can sense the current and voltage between each pair of the probes in real time and communicate such information to the controller 71, which in turn, communicates the information to the computer 40. Although the treatment control module 54 houses the software code for monitoring the treatment procedure, it may be beneficial for the controller 71 to store such module as the speed of monitoring can be important in some cases.

Figure 4:
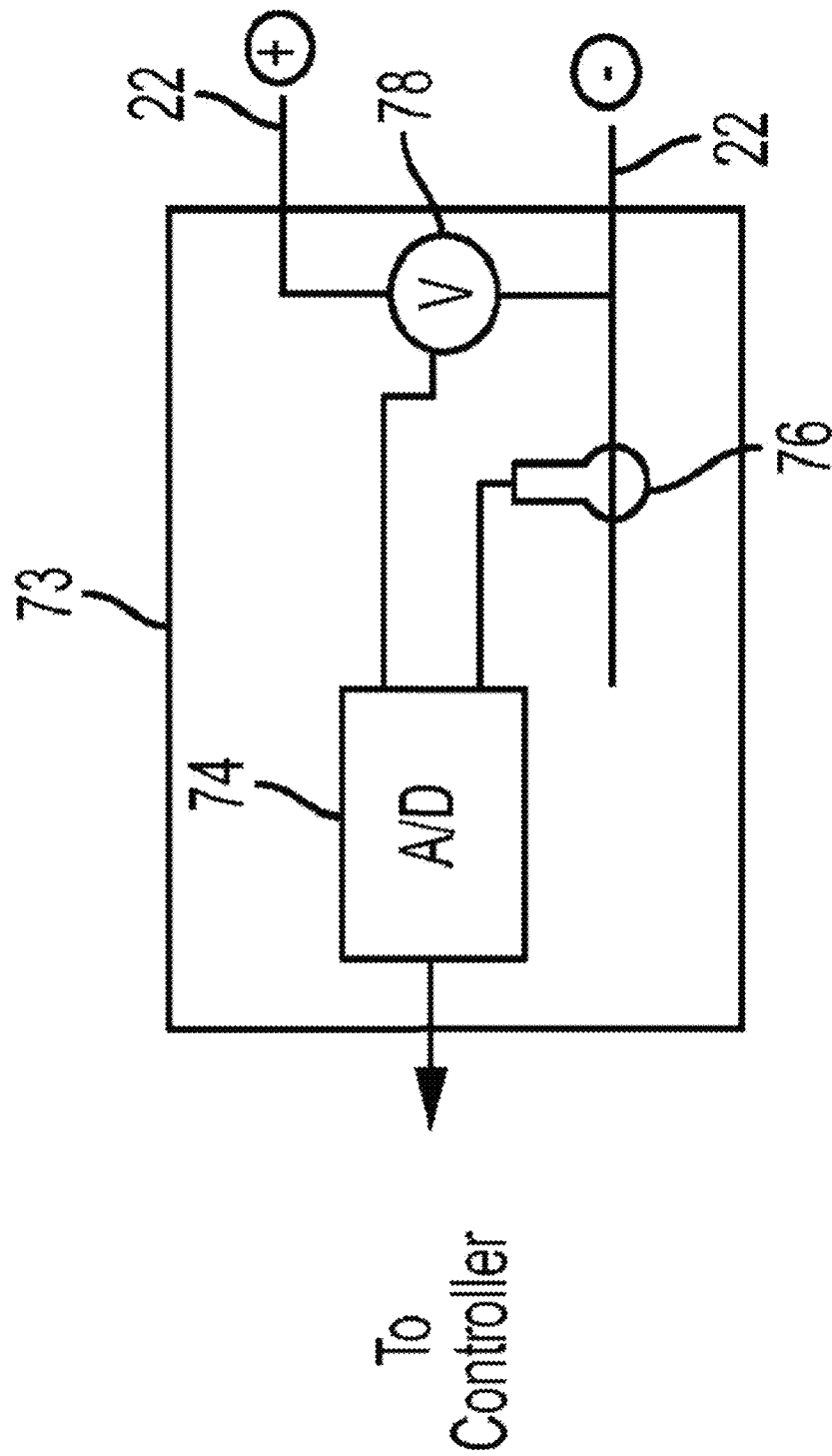
FIG. 4 is a block diagram of a sensor of FIG. 3.

FIG. 4 is a functional block diagram of a sensor 73 of FIG. 3. The sensor 73 includes a voltage, current, or impedance sensor 78 connected across a pair of electrodes 22 and a current sensor or output monitor 76 connected to a negative electrode (return conduit) in the pair of electrodes. Although FIGS. 3-4 show two electrodes from two wires 22, there may be multiple electrodes between the two wires 22. The sensed values are continuously received and digitized by an A/D converter 74 and transmitted to the controller 71. Preferably, the A/D converter 74 can sample the sensed values at a very fast rate and preferably at a rate of at least 100 MHz (100 million samples per second) for the control module 54 to be able to accurately assess the complex impedance of test signals which may be an AC signal at a relatively high frequency.

The current sensor 76 can be a Hall effect sensor/probe which is positioned around an electrode so as to measure the electric current without directly interfering with the pulse signal. Typically, the current sensor 76 is placed on the negative signal connection of the electrode pair. If the electrode pairs are switched, then only one current sensor connected at the input side of the switch is needed. Otherwise, if there are 3 pairs of electrodes, for example, and all are firing at the same time, there will be 3 current sensors so as to measure the electric current of each pair separately. In that case, the current from the three sensors will need to be added. Such embodiments are helpful in circumstances where the practitioner desires to stay below a certain current threshold. The inventive activation protocols can also be used to minimize the amount of current delivered to the target region during the treatment. For example, rotating or distributing the application of energy in the treatment zone can keep the amount of current delivered at a minimum. The amount of current being delivered can be monitored, such as using sensor(s), and the activation protocol adjusted accordingly to avoid current rising above a desired threshold. For example, a practitioner monitoring the current could adjust the protocol to skip a cycle or reduce the number of pulses/bursts being applied if the current readings from the sensor indicate the amount of current is getting too high.

The voltage sensor 78 can be a conventional voltage divider, comprised of two serially connected resistors, that measures a voltage drop across a known resistance value. The voltage sensor 78 uses resistors which are of much higher resistance than the tissue (k$\Omega$-M$\Omega$, versus tissue, which is hundreds of $\Omega$), and thus induces negligible effect on the strength of the pulses delivered to the tissue. A correction factor is calculated for the divider circuit based on the resistances of the two resistors in the voltage divider circuit and the resistance of the load (tissue resistance) to determine the true delivered voltage to the tissue based on the measured voltage drop across the resistor.

The software program modules in the program storage 48 and data from the data storage 50 can be configured so that one or more treatment parameter such as current can be inputted, stored, and/or displayed to the user/physician on the display device 11. The one or more treatment parameter can be stored in the data storage 50, and values such as the absolute values or average values of the one or more treatment parameter or relative values, such as the amount of change in the one or more treatment parameter over time, can be inputted, stored, and/or displayed by the user/physician. In one embodiment, the treatment parameter values are stored as thresholds.

The software program modules in the program storage 48 can include programming configured to determine an average value or a change in value of a non-thermal ablation treatment parameter measured in real time during treatment. The programming can input measured values of a treatment parameter during real time monitoring such as current, and calculate an average value over time, or a change in value, such as from a baseline. The baseline can be established at various time points before or during treatment.

Now having described the embodiments of the present disclosure, in general, the following Example describes some additional embodiments of the present disclosure. While embodiments of the present disclosure are described in connection with the following example and the corresponding text and figures, there is no intent to limit embodiments of the present disclosure to this description. On the contrary, the intent is to cover all alternatives, modifications, and equivalents included within the spirit and scope of the principles of the present disclosure.

Example

Abstract

Purpose: To evaluate the effects of various pulsing paradigms, on the irreversible electroporation (IRE) lesion, induced electric current, and temperature changes using a perfused porcine liver model.

Materials and Methods: A 4-monopolar electrode array delivered IRE therapy varying the pulse length and interpulse delay to six porcine mechanically perfused livers. Pulse paradigms included six forms of cycled pulsing schemes and the conventional pulsing scheme. Finite element models provided further insight into the effects of cycled pulsing on the temperature and thermal injury distribution.

Results: "Single pulse cycle with no interpulse delay" deposited maximum average energy (2.34±0.35 kJ) and produced the largest ratio of thermally damaged tissue area and IRE ablation area from all other pulse schemes (18.22%±8.11, p<0.0001 all pairwise comparisons). These compared favorably to the conventional algorithm (2.09±0.37 kJ, 3.49%±2.20, p<0.0001, all comparisons). Though no statistical significance was found between groups, the "5 pulse cycle, 0 s delay" pulse paradigm produced the largest average IRE ablation cross sectional area (11.81±1.97 cm2), while conventional paradigm yielded an average of 8.90±0.91 cm2. Finite element modeling indicated "10 pulse cycle, 10 s delay" generates the least thermal tissue damage and "1 pulse cycle, 0 s delay" pulse cycle sequence the most (0.47 vs. 3.76 cm2), over a lengthier treatment time (16.5 vs. 6.67 minutes).

Conclusions: Subdividing IRE pulses and adding delays throughout the treatment can reduce white tissue coagulation and electric current, while maintaining IRE treatment sizes. For example, see "10 pc/5 s delay" and "10 pc/10 s delay" protocols with either conventional or enhanced EPAP, as shown in FIGS. 12A-C.

Introduction

Irreversible Electroporation (IRE) is an energy directed therapeutic used to treat patients with unresectable tumors. This focal ablation technique relies on the application of brief, high-amplitude, pulsed electric fields between two or more needle applicators/electrodes to increase the transmembrane potential of a cell above a critical threshold, destabilize the lipid bilayer of the cell membrane, increase the cell-tissue permeability, and ultimately kill cells within the targeted region. The overall ablation volume is contingent on the underlying tissue properties and the various energy delivery parameters. Energy delivery can be partially defined as a function of the physical delivery system (the electrode geometry, the number of electrodes utilized, and electrode spacing), as well as the systematic electrical pulse parameters (voltage amplitude, pulse frequency, and pulse repetition). The proper tuning of these electrode properties and pulse parameters can enable a targeted, non-thermal treatment of local and inoperable tumors. Consequently, this minimally invasive technique can be used to target malignancies enveloping critical structures (blood vessels, major nerves, etc.) and is less influenced by the convective effects of local blood perfusion (heat sink effect) in comparison to thermal ablative technologies (radiofrequency ablation, and microwave ablation, etc.) (see B. E. Bulvik, M. Ahmed, A. V Andriyanov, and S. N. Goldberg, "Irreversible Electroporation versus Radiofrequency Ablation: A Comparison of Local and Systemic," vol. 280, no. 2, 2016).

Treatment of large tumors benefit from higher voltages which in turn cause moderate temperature and current variations; the latter has been linked to overall treatment outcomes (see E. Ben-David et al., "Irreversible Electroporation: Treatment Effect Is Susceptible," *Radiology*, vol. 269, no. 3, 2013; B. E. Bulvik, M. Ahmed, A. V Andriyanov, and S. N. Goldberg, "Irreversible Electroporation versus Radiofrequency Ablation: A Comparison of Local and Systemic," vol. 280, no. 2, 2016. Studies have shown that while a higher delivered electrical energy can be associated with larger treatment zones, it also causes an increase in white tissue coagulation due to Joule heating effects. Some thermal mitigation strategies have been explored, including methods to absorb and remove heat via internal perfusion and the use of phase change materials within the electrode/applicator core. However, these methods may increase operational complexity and/or require thicker electrodes. In many instances, clinicians performing IRE treatments will also rely on increasing the number of monopolar IRE applicators to three or more to encompass a large or irregularly shaped tumor. On these occasions, conventional IRE generators would deliver the entirety of the set number of pulses for a given electrode pair before proceeding to the next electrode pair, until all of the desired electrode pair combinations have been activated making this procedure time consuming. Moreover, while the addition of electrodes may be useful in generating a larger ablation, the existing method of pulse delivery has not been engineered to moderate thermal tissue damage.

The inventors have investigated the effects of various cycled pulsing paradigms in comparison to conventional pulsing schemes via a multi-electrode IRE therapy (4-electrode configuration) on the IRE treatment zone size, deployed electrical current, temperature changes, and treatment time. The inventors have discovered that subdividing the number of pulses delivered per electrode pair and adding delays throughout the treatment are techniques that can be used to reduce tissue temperatures, electric current, and the overall thermal damage while maintaining IRE treatment zone sizes. For example, as shown in FIG. 10I, the "10 pulse cycle, 10 s delay" pulse cycle sequence illustrated a 99.3% reduction of thermal damage area in comparison to the conventional pulse scheme, and each of the multi-cycle pulsing paradigms illustrated less area thermal damage on average than the single-cycle scheme ("1 pulse cycle, 0 s delay" and the conventional pulse scheme). Additionally, as shown in FIGS. 12A-B, the incorporation of cycled pulsing, with an enhanced EPAP could reduce the surface area and volumetric thermal damage as much as 13.6% in comparison to the conventional pulse paradigm, while maintaining the effective electric field thresholds within 2.1%. Further, an adjustment to the order in which each electrode pair is activated during treatment was also explored in an attempt to further minimize the potential for Joule heating.

Materials and Methods

Electroporation Pulse Delivery

All IRE treatments were performed in a perfused organ model (see S. Bhonsle et al., "Characterization of Irreversible Electroporation Ablation with a Validated Perfused Organ Model," *J. Vasc. Interv. Radiol.*, vol. 27, no. 12, pp. 1913-1922.e2, 2016; and T. J. OBrien et al., "Effects of internal electrode cooling on irreversible electroporation using a perfused organ model," *Int. J. Hyperth.*, vol. 35, no. 1, pp. 44-55, 2018). A total of six livers were used for this study with 6-8 treatments delivered per liver using a 4-electrode configuration electrode array. Five cycled pulsing variations were performed (Table 2) and evaluated in comparison to a conventional algorithm. As shown in FIGS. 5A-C, a 4-electrode array was used to deliver the various pulse protocols, including a conventional pulse protocol (FIG. 5A) using a conventional electrode pair activation pattern (EPAP), a cycled pulsing protocol (FIG. 5B) also using a conventional EPAP (and the same EPAP as in FIG. 5A), and a cycled pulsing protocol (FIG. 5C) using an enhanced EPAP. As shown in each of FIGS. 5A-C, the activated electrode is shown encircled in bold and the arrow denotes the flow of energy toward to other electrode in the pair being activated. The pairs of activated electrodes are shown encircled with an oval.

Conventional pulsing protocols typically deposit the total number of pulses/bursts desired across one electrode pair before moving to the next electrode pair, as illustrated within FIG. 5A where 100 pulses are deposited per electrode pair. This pulsing algorithm includes a 3.5 s delay per every 10 pulses to recharge the capacitor bank, which provides some thermal mitigation.

By comparison, the cycled pulsing schemes investigated differ by partitioning of the pulse-train into subsets of pulses (30, 60, 120, etc.) and cycling between active electrode pairs until the desired final number of pulses is achieved per electrode pair (FIG. 5B). Thus, the "5 pulse cycle, 0 s delay" scheme applies 20 pulses per electrode pair (6 electrode pairs), yielding a total of 120 pulses per "cycle". This procedure is repeated until a total of 600 pulses are applied (i.e. a total of 5 cycles). While there is no delay between activated electrode pair pulsing sequence associated with this "5 pulse cycle, 0 s delay" method, the addition of a delay between each cycle was also investigated. In embodiments, delays can take the form or any one or more of inter-pulse delays (one or more delay between pulses), inter-burst delays (one or more delay between bursts of pulses), and/or inter-cycle delays (one or more delay between cycles of pulses or bursts being applied). Lastly, as thermal damage is typically associated with temperature and on time, the order in which electrode pairs activate was examined to minimize consecutive electrode activation and thus allow the tissue more time to rest between activations and reduce the amount of unwanted thermal damage to the tissue. FIG. 5C shows one such enhanced electrode pair activation pattern.

More particularly, in embodiments such as the cycled pulsing protocol of FIG. 5B, a conventional electrode pair activation pattern (EPAP) is used. Typically, in such a protocol the electrode pairs with the largest distance between them (e.g., the diagonal electrodes) are activated first. Then since the remaining electrode pair combinations each have the same distance of separation between the electrodes in each pair (e.g., in a 4-electrode configuration), any of the remaining electrode pairs are activated sequentially/consecutively until all pairs have been activated. With such a protocol, a single electrode can be activated three times in a row.

Cycled pulsing embodiments that use an enhanced electrode pair activation protocol (EPAP) as in FIG. 5C, typically can start out similarly to that of the beginning of the protocol in FIG. 5B, where (1) the electrodes with the largest separation distance (e.g., the diagonal electrodes) are activated first, (2) and any of the remaining electrode pairs can be activated next, but differing from the FIG. 5B protocol in that (3) each of the remaining electrode pairs is activated in an order such that the electrodes of the electrode pair were not activated in the last activation. For example, activating a pair of electrodes opposite the last pair of electrodes activated avoids sequential/consecutive activation of an electrode. This "enhanced" EPAP results in allowing the tissue more time to rest between electrode pair activations. As shown in FIG. 12B, typically the amount of tissue damage for the enhanced EPAP protocols was less than the amount associated with the conventional EPAP protocols.

TABLE 2

Summary of the treatment variations of cycled pulse sequencing. Six different pulsing paradigms were compared. Conventional pulsing sequences typically incorporate a 3.5 second delay per every 10 pulses/bursts (due to capacitor charging), while all other pulsing paradigms implement their delays between cycles. Pulse delivery was iterated between four monopolar electrodes equally spaced apart by 2 cm, with an electrode exposure of 1.5 cm. The IRE generator was set to deliver 600 pulses at a rate of 90 pulses per minute and a constant voltage of 2700 V.

| Parameter Set | No. Cycles | Delay [s] | No. Pulses per Cycle | No. Total Pulses | Electrode Separation [cm] | Electrode Exposure [cm] | Pulse Amplitude [V] | Pulse Width [µs] |
|---|---|---|---|---|---|---|---|---|
| Conventional Paradigm | 1 | 3.5 per 10 pulses | 100 | 600 | 2 | 1.5 | 2700 | 100 |
| 1 pulse cycle, 0 s delay | 1 | 0 | 100 | 600 | 2 | 1.5 | 2700 | 100 |
| 5 pulse cycle, 0 s delay | 5 | 0 | 20 | 600 | 2 | 1.5 | 2700 | 100 |
| 10 pulse cycle, 0 s delay | 10 | 0 | 10 | 600 | 2 | 1.5 | 2700 | 100 |
| 10 pulse cycle, 5 s delay | 10 | 5 | 10 | 600 | 2 | 1.5 | 2700 | 100 |
| 10 pulse cycle, 10 s delay | 10 | 10 | 10 | 600 | 2 | 1.5 | 2700 | 100 |

Perfused Whole Organ Tissue Testing

Organ Preparation

All experimental IRE procedures are performed on a previously validated perfused organ model (see S. Bhonsle et al., "Characterization of Irreversible Electroporation Ablation with a Validated Perfused Organ Model," *J. Vasc. Interv. Radiol.*, vol. 27, no. 12, pp. 1913-1922.e2, 2016). Porcine livers were excised at a local abattoir and immediately fit with Luer-Lock connectors at the major ports of the specimen for a constant pressure flush (~90 mmHg) with three liters of modified phosphate buffer solution (conductivity of ~0.8 S/m) to mitigate thrombosis and improve overall tissue perfusion. The tissue was then transported via static cold storage (SCS) until anastomosed to the organ preservation system (~120 minutes on SCS). The perfusate temperature on the preservation system was set and maintained at 30° C. After IRE treatments were delivered, organs were maintained on the system for an additional 2 hours at hypothermic conditions, 4° C., and prior to sectioning/staining. A total of six livers were used, with 6-8 treatments performed per liver (total N=42). All animals were euthanized and handled in strict accordance with good animal practice as defined by the relevant national and local animal welfare bodies, and approved by Virginia Tech.

To ensure that all electrodes were equidistant for each treatment performed during these experiments, a custom built "support block" was designed and laser-cut from acrylic material (CAD diagram shown in FIG. 6A). FIG. 6D illustrates the monopolar support block for the 4-monopolar electrode configuration, FIGS. 6B and 6C show fiber optic sensor placement relative to the electrode array, and FIG. 6E shows a detailed schematic of the machine perfused liver model.

Morphologic Analysis

Figure 7A:
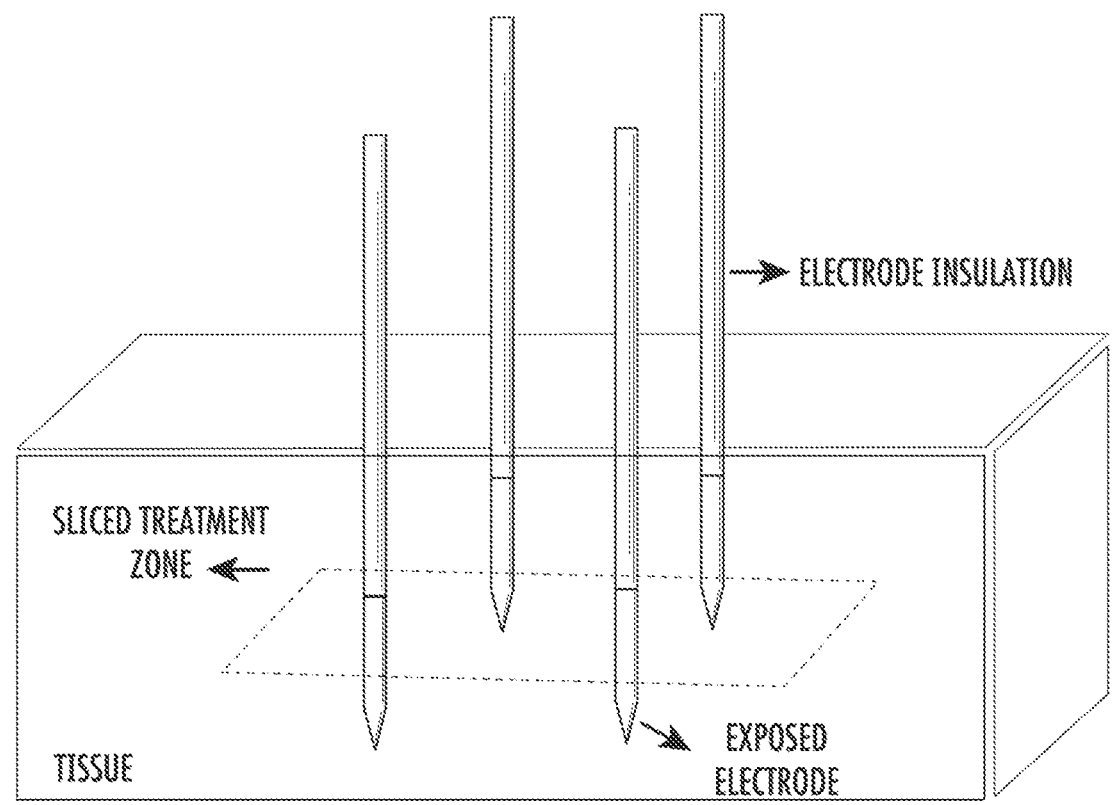
FIG. 7A is a schematic diagram showing the placement of four monopolar electrodes. The sliced plane is taken at the midpoint of the IRE ablation depth. One half is used to measure the cross-sectional area.
Figure 7B:
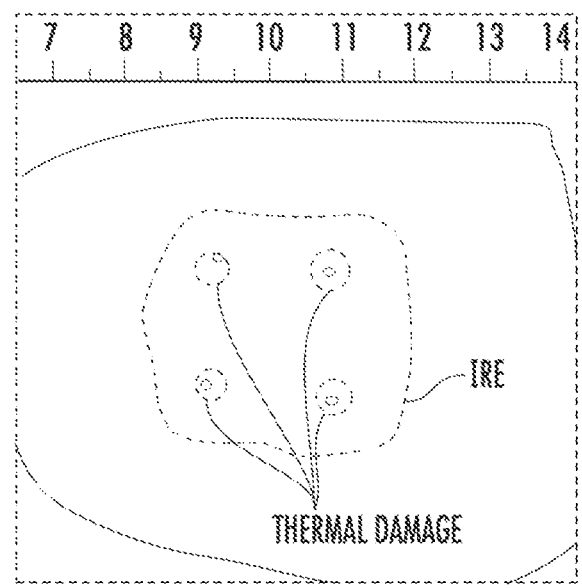
FIG. 7B shows the IRE ablation zone and thermally damaged regions are highlighted.

Sectioning was performed 2 hours after the last ablation performed to allow for IRE changes to manifest (see E. W. Lee, C. Chen, V. E. Prieto, S. M. Dry, C. T. Loh, and S. T. Kee, "Advanced Hepatic Ablation Technique for Creating Complete Cell Death: Irreversible Electroporation," *Radiology*, vol. 255, no. 2, pp. 426-433, 2010). The total perfusion time was no more than 6 hrs. The tissue was sectioned and sliced through the mid-plane of the treatment regions for gross evaluation. These sections were stained with triphenyl tetrazolium chloride (TTC) (MP Biomedicals, LLC Santa Ana, California) in phosphate buffered saline (15 g/L) for 5-10 minutes without light exposure. Following staining, the treatment zones were photographed and measured along the long and short axis to determine the overall area of the treatment region. Samples were fixed in formalin overnight and measured once more 12 hours later. Prior studies have shown no statistical difference in ablation size when comparing the long and short axis measurements pre- and post-formalin (see M. Bonakdar, E. L. Latouche, R. L. Mahajan, and R. V. Davalos, "The feasibility of a smart surgical probe for verification of IRE treatments using electrical impedance spectroscopy," *IEEE Trans. Biomed. Eng.*, vol. 62, no. 11, pp. 2674-2684, 2015; and E. L. Latouche, M. B. Sano, M. F. Lorenzo, R. V. Davalos, and R. C. G. Martin, "Irreversible electroporation for the ablation of pancreatic malignancies: A patient-specific methodology," *J. Surg. Oncol.*, vol. 115, no. 6, pp. 711-717, 2017). Thus, the post formalin measurements were used to represent ablation size throughout the Example. ImageJ software (NIH, Bethesda, MD) was used to analyze and measure the thermally damaged regions and IRE ablated regions of each tissue sample. Briefly, threshold techniques were utilized to identify the thermally damaged tissue (discolored tissue regions) and IRE ablation (pale discolored tissue regions). Then, the average thermally damaged area and average IRE ablation area were expressed as percentage ratio of thermal damage to IRE ablation. FIGS. 7A-B illustrate the sectioning and ablation measurement process. It should be noted the calculated IRE ablation area also includes the thermally damaged area (area of white tissue coagulation); this combination was purposely included to calculate the percentage of thermal damage in proportion to the entire ablation, both nonthermal ablation and thermally damaged area.

Thermal Measurements

Fiber optic thermal sensors (STB, Luxtron m3300, LumaSense, Santa Clara, CA, USA) were adhered to the surface, and positioned at the midpoint of each exposed electrode. The tissue temperature was measured during treatment at a rate of 0.5 samples per second. Temperature data was plotted over time to illustrate the thermal differences between each pulsing paradigm investigated. Further, the collected thermal data was utilized to validate the numerical models. FIGS. 6B and 6C specify the location of each fiber optic temperature sensor in relation to the electrodes.

Current Measurements

The system generated .xml data files containing the treatment protocol and procedure, voltage, current, and resistance information. All data were imported and read using an in-house MATLAB program for analysis of the measured current. Similar data (voltage, current and resistance) were generated and saved for all cycled pulsing paradigms. The total energy delivered to the tissue was calculated via Equation 2:

$$\text{Energy [kJ]} = \frac{[V_{avg} * I_{avg}] * (\# \text{ Pulses}) * (100 \times 10^{-6})}{1000} \quad [2]$$

Where the average voltage, $V_{avg}$, and average current, $I_{avg}$, are defined as the area under the curve divided by the treatment length.

Numerical Modeling of Varying Cycled Pulsing Paradigms

Numerical modeling was performed in parallel with experimental procedures to explore the effects of various cycled pulsing paradigms for multi-electrode IRE treatments in ex vivo porcine liver tissue. Previously measured experimental voltage and current data were employed to visualize electroporation-induced changes in electrical conductivity, thereby solving for more representative electric field distributions and applied electric currents. The finite element model was developed using COMSOL Multiphysics v5.4a (COMSOL Inc., Stockholm, Sweden). The domains consisted of liver tissue modeled as a 12×12×8 cm ellipsoid and four monopolar electrodes modeled as cylinders with height, diameter, and spacing of 1.5 cm, 1 mm, and 2 cm, respectively. All numerical model material properties are displayed in Table 3.

TABLE 3

Material properties used within the numerical model.

| Material | Parameter | Value | Units | Ref. |
|---|---|---|---|---|
| Liver | ρ, Density | 1079 | [kg/m³] | P. Hasgall et al. |
| | $c_p$, Heat Capacity | 3540 | [J/kg/K] | P. Hasgall et al. |
| | k, Thermal Conductivity | 0.52 | [W/m/K] | P. Hasgall et at. |
| | α, Thermal Coefficient of Conductivity | 2 | [%/° C.] | P. Hasgall et at. |
| | $\omega_b$, Perfusion | 3.575 × 10⁻³ | [1/s] | P. Hasgall et al. |
| | σ, Electrical Conductivity | 0.67 | [S/m] | P. Hasgall et al. |
| | $E_o$, Reversible Field Threshold | 460 | [V/cm] | D. Haemmerich and B. J. Wood |
| | $E_1$, Irreversible Field Threshold | 700 | [V/cm] | D. Haemmerich and B. J. Wood |
| Electrode | ρ, Density | 7900 | [kg/m³] | P. Hasgall et at. |
| | $c_p$, Heat Capacity | 500 | [J/kg/K] | P. Hasgall et at. |
| | k, Thermal Conductivity | 15 | [W/m/K] | P. Hasgall et al. |
| | σ, Electrical Conductivity | 2.22 × 10⁶ | [S/m] | P. Hasgall et al. |

The final mesh consisted of 187,418 tetrahedral elements with a maximum of 2,264,706 degrees of freedom. The electric potential distribution was solved using the Laplace equation (Equation 3), and taking the gradient of the electric potential (Equation 4):

$$-\nabla \cdot (\sigma \nabla \phi) = 0 \quad [3]$$

$$\overline{E} = -\nabla \Phi \quad [4]$$

where σ represents the electrical conductivity, φ is the electric potential, and $\overline{E}$ is the electric field. Considering a four-electrode configuration, and assuming that all six electrode pair combinations were used within the treatment, a total of six current modules were required to solve for the effective electric field distribution, each of which had imposed boundary conditions of ϕ=V and ϕ=0. All external boundaries were set as electrically insulating with the boundary condition $$\frac{\partial \phi}{\partial n} = 0.$$

Prior studies have shown tissue electroporation results in an increase in bulk tissue electrical conductivity. This effect is captured in the model by using a sigmoidal curve:

$$\sigma(|\bar{E}|) = \sigma_0 + \frac{\sigma_f - \sigma_0}{1 + D \cdot e^{\frac{-(|E|-A)}{B}}} \quad [5]$$

where $\sigma_0$ is the initial non-electroporated conductivity, $\sigma_f$ is the peak electroporated conductivity, |E| is the magnitude of the electric field at any given position, and D, B, and A are fitting terms. In the context of the perfused organ model, the empirically determined values for $\sigma_0$, $\sigma_f$, D, B, and A are 0.12 S/m, 0.42 S/m, 10, 30 V/cm, and 580 V/cm, respectively. Due to the increase ionic mobility during therapy, the electrical conductivity of biological tissue increases with temperature, and is incorporated within the model via the electrical conductivity temperature coefficient, α:

$$\sigma(|\bar{E}|,T) = \sigma(|\bar{E}|) \cdot [1 + \alpha \cdot (T - T_0)] \quad [6]$$

For direct current (DC) and low-to-medium frequencies (30 kHz-1 GHz), α is a positive coefficient taking on values between 0-4%/° C. Here, the α coefficient was defined as 2%/° C.

Temperature profiles are simulated using Pennes' bioheat equation that models conductive heat transfer and includes effects of heat dissipation due to a distributed blood perfusion term. The bioheat equation was modified to incorporate IRE Joule heating effects through the addition of a Joule heating term. To reduce computational time, the energy delivered during one pulse (100 μs) was averaged over the pulsing period (1 s) by scaling this Joule heating term to the duty cycle of the pulse. Thus, discrete pulses can now be defined as a continuous heat source without complex modifications to the numerical time stepping.

Figure 8:
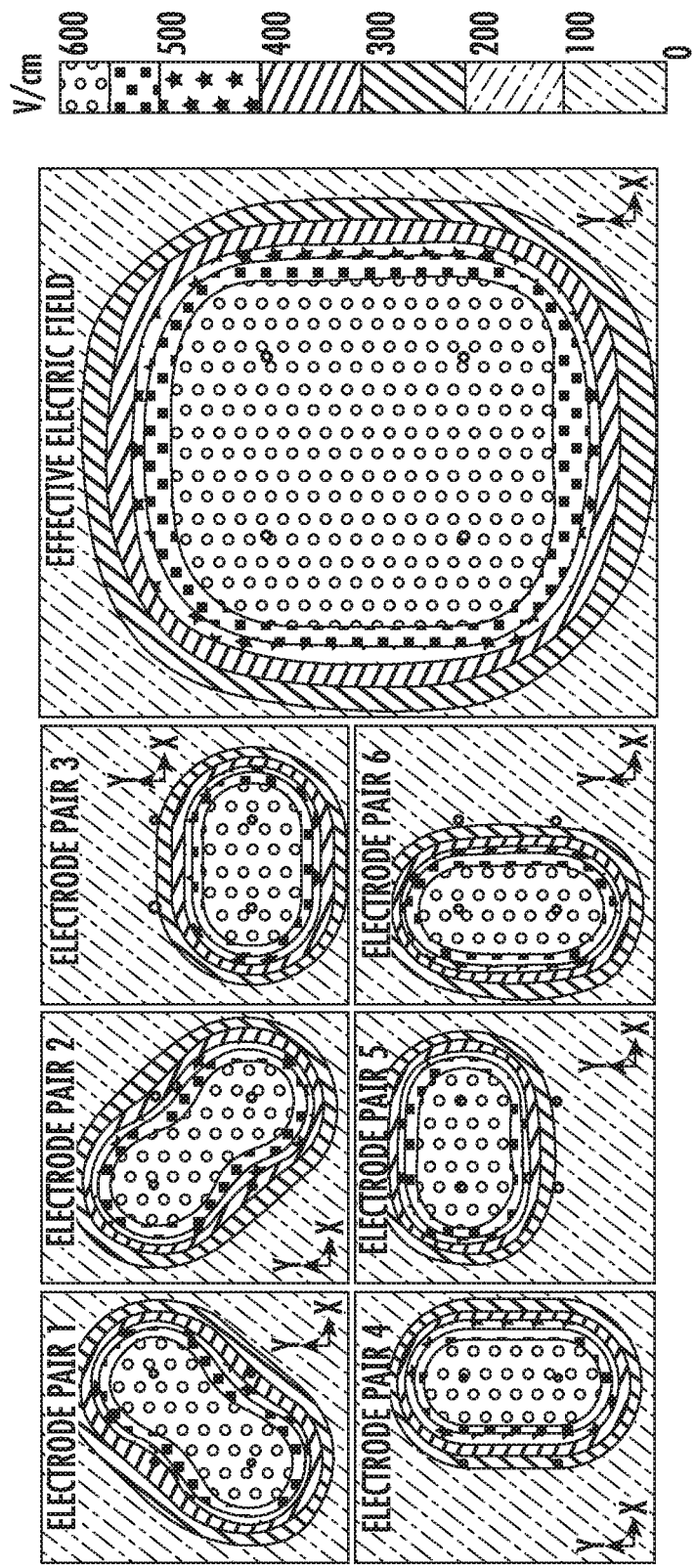
FIG. 8 is a series of illustrations showing visualization of the electric field distributions for each electrode pair. The combined maximum intensity of each individual field represents the effective electric field distribution from treatment with this four electrode array. This sequence of pulsing represents a conventional pulsing scheme.

Lastly, the cycled pulsing schemes are implemented by combining the duty cycle approach with time dependent "thermal envelopes". These thermal envelopes are implemented analytically where a defined coefficient χ is used to simulate the on (χ=1) and off (χ=0) period of the Joule Heating term. Since the Joule Heating term is a continuous source, these "thermal envelopes" enable the numerical model to mimic cyclic pulsing across various electrode pairs, with Joule Heating occurring only across the immediately energized electrode pair. This resulted in the following equation:

$$\rho c_p \frac{\partial T}{\partial t} = \nabla \cdot (k \nabla T) - \omega_b \rho_b c_b (T - T_b) + \frac{\sigma \cdot |\bar{E}|^2 \cdot p}{\tau} \cdot \chi \quad [7]$$

where ρ describes the density of tissue, $c_p$ is the specific heat of tissue, κ is the thermal conductivity, $\omega_b$ is the perfusion, $\rho_b$ describes the density of blood, $c_b$ is the specific heat of blood, $T_b$ is the arterial blood temperature, σ represents the electrical conductivity, p is the period per pulse, and τ represents the on-time per pulse. FIG. 8 illustrates the numerically calculated electric field distributions for each individual electrode pair and the cumulative or effective electric field using a conventional pulsing paradigm for a four electrode configuration. The area was calculated for tissue that exceeded electric field thresholds of 400, 600 800, and 1000 V/cm and both the conventional and enhanced EPAPs using a surface integration taken across the plane at the midpoint of the electrodes within the 3D model.

The accumulation of tissue thermal injury tissue due to pulsing was quantified using a thermal damage function:

$$\Omega(t) = \int_0^t \zeta \cdot e^{-\frac{E_a}{R \cdot T(t)}} dt \quad [8]$$

where ζ is the frequency factor (7.39×10³⁹ s⁻¹), $E_\alpha$ is the activation energy (2.577×10⁵ J/mol), R is the universal gas constant, T is the absolute temperature in Kelvin, and Ω, is the total injury due to thermal insult. A value of, Ω=2.3, was used to define the minimum conditions to obtain irreversible hepatic white tissue coagulation.

The total treatment time was calculated using the formula displayed in Equation 9:

$$\text{Total Treatment Time [min]} = \frac{\left[\left(\frac{P_\#}{C_\# \cdot f}\right) + (D)\right](\varepsilon_p)(C_\#)}{60} \quad [9]$$

Where $P_\#$ is defined as the number of pulses per electrode pair, D represents the delay between cycles, $\varepsilon_p$ is the total number of electrode pair combinations employed in the therapy, $C_\#$ is the number of cycles, and f is the pulse delivery rate (90 pulses per minute).

To determine and closeness of fit and validate the numerical model, the numerically calculated initial and final electrical current for each pulsing scheme was compared to the experimentally measured initial and final current. Further, the temperature at each electrode was calculated and compared to the experimentally measured temperatures at each electrode.

Numerical Model Validation

Figure 9:
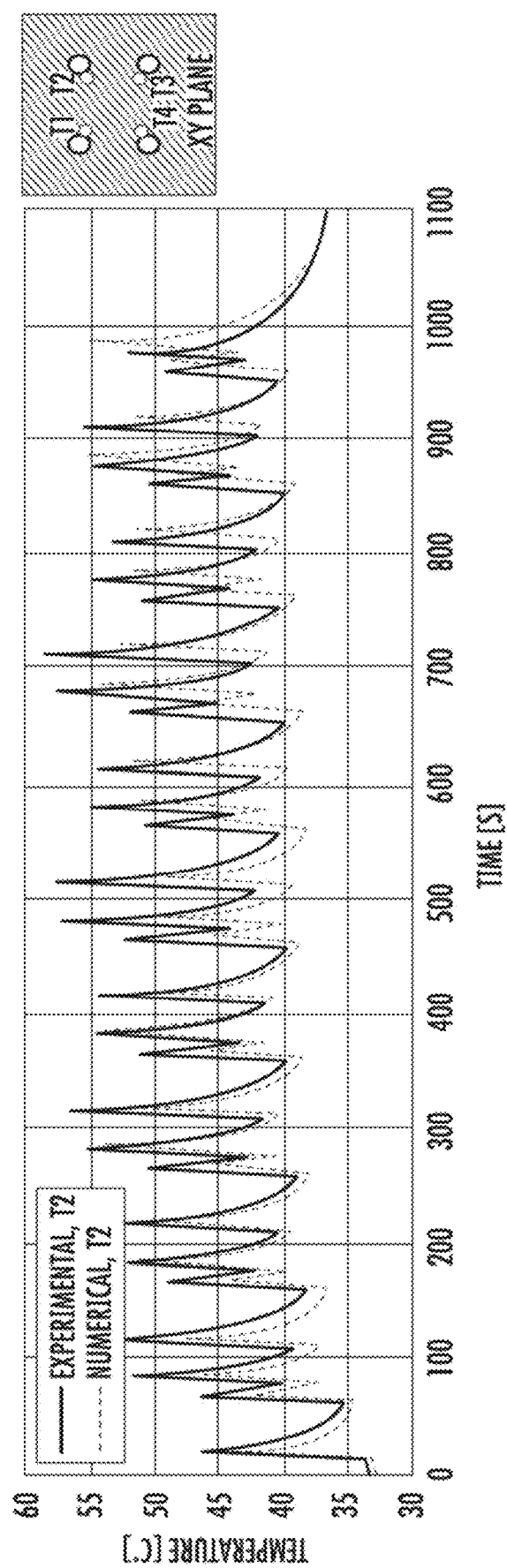
FIG. 9 is a graph which illustrates the measured and numerically calculated thermal response for a "10 pulse cycle, 10 s delay" pulsing sequence at electrode 2 (T2). A schematic illustrating fiber optic thermal probe location relative to electrodes is shown in the top right corner of the figure. The average RMSE for each electrode was 6.02° C. for this pulsing paradigm.

The numerical model current was determined by integrating the normal current density over the sink electrode. Percentage error calculations were performed to compare the numerically calculated currents and average experimentally measured currents at the start and end of treatments. Further, temperature measured at each electrode was compared to the numerical model via root mean square error (RMSE) calculation, also shown in Table 4. FIG. 9 illustrates the closeness in fit from a thermal perspective.

TABLE 4

Comparison between the numerical model and actual experimental results for the initial and final current of each pulsing scheme:

| Pulsing Scheme | Percent Error Initial Current [%] | Percent Error Final Current [%] | RMSE of Temperature [° C.] |
|---|---|---|---|
| Conventional Paradigm-Exp. Conventional Paradigm-Model | 5.04 | 0.19 | 8.61 |

TABLE 4-continued

Comparison between the numerical model and actual experimental results for the initial and final current of each pulsing scheme:

| Pulsing Scheme | Percent Error Initial Current [%] | Percent Error Final Current [%] | RMSE of Temperature [° C.] |
|---|---|---|---|
| 1 pulse cycles, 0 s delay-Exp. | 1.24 | 2.47 | 6.22 |
| 1 pulse cycles, 0 s delay-Model | | | |
| 5 pulse cycles, 0 s delay-Exp. | 1.10 | 10.31 | 8.83 |
| 5 pulse cycles, 0 s delay-Model | | | |
| 10 pulse cycles, 0 s delay-Exp. | 7.23 | 9.74 | 9.16 |
| 10 pulse cycles, 0 s delay-Model | | | |
| 10 pulse cycles, 5 s delay-Exp. | 5.74 | 4.60 | 9.66 |
| 10 pulse cycles, 5 s delay-Model | | | |
| 10 pulse cycles, 10 s delay-Exp. | 6.93 | 4.37 | 6.02 |
| 10 pulse cycles, 10 s delay-Model | | | |

Statistical Analysis

A total of six livers were used, with 6-8 treatments performed per liver (total N=42). Data are presented as mean values±standard deviation of the mean. A one-way analysis of variance (ANOVA) was used to determine whether different pulsing paradigms yielded an effect for the parameter of interest. For parameters in which the ANOVA showed an effect, a secondary Tukey's test was performed to determine which pulsing paradigm(s) were significantly different from others. All statistical analysis was performed within JMP® Pro version 14.0.0 (SAS Institute Inc., Cary, N.C.).

Results

Perfused Whole Organ Tissue Testing

Figure 10G:
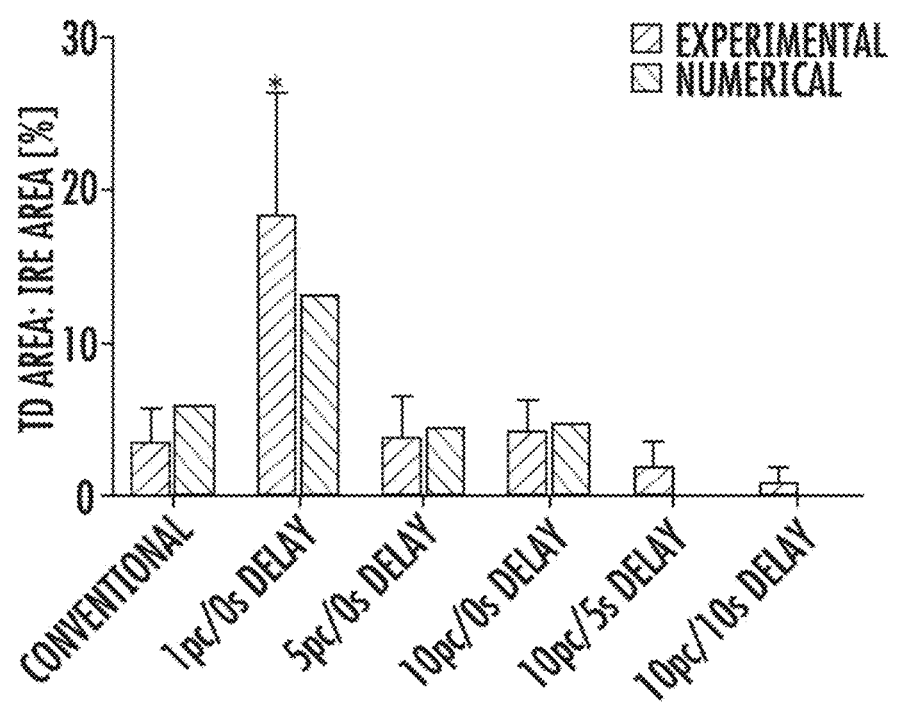
FIGS. 10G-I are graphs showing a comparison between the experimental and numerical results for the percentage ratio of thermal damage as shown by the white tissue coagulation area (i.e., tissue whitening) to IRE treatment zone area (FIG. 10G) ($p<0.0001$, all pairwise comparisons), the average cross-sectional ablation area for each pulse scheme (FIG. 10H), and the average area of white tissue coagulation (FIG. 10I) ($\Omega=2.3$, $p<0.0001$, all pairwise comparisons).
Figure 10H:
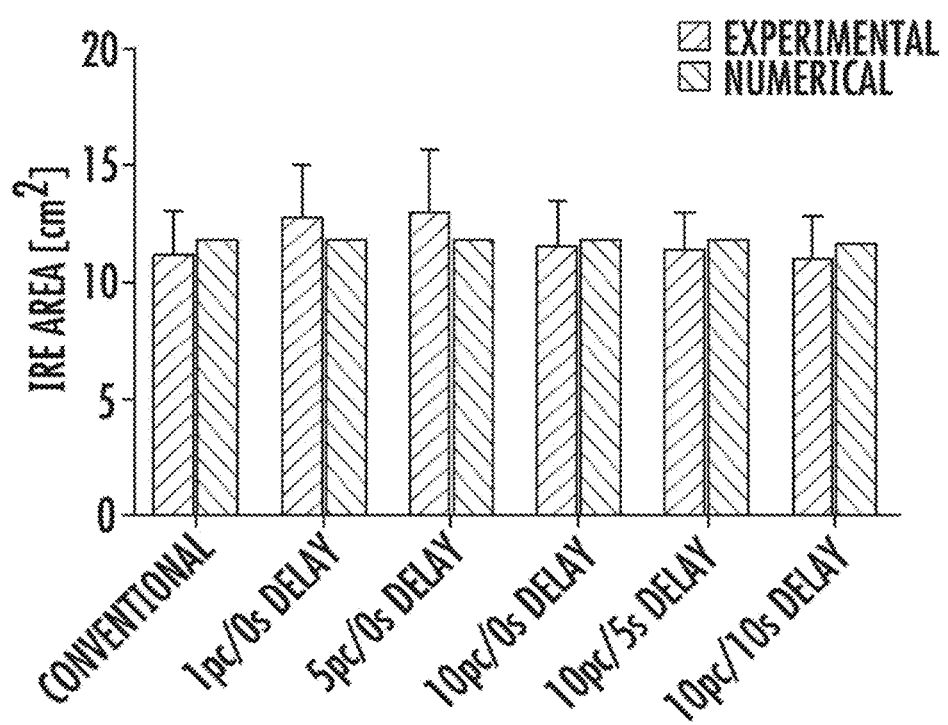
Figure 10I:
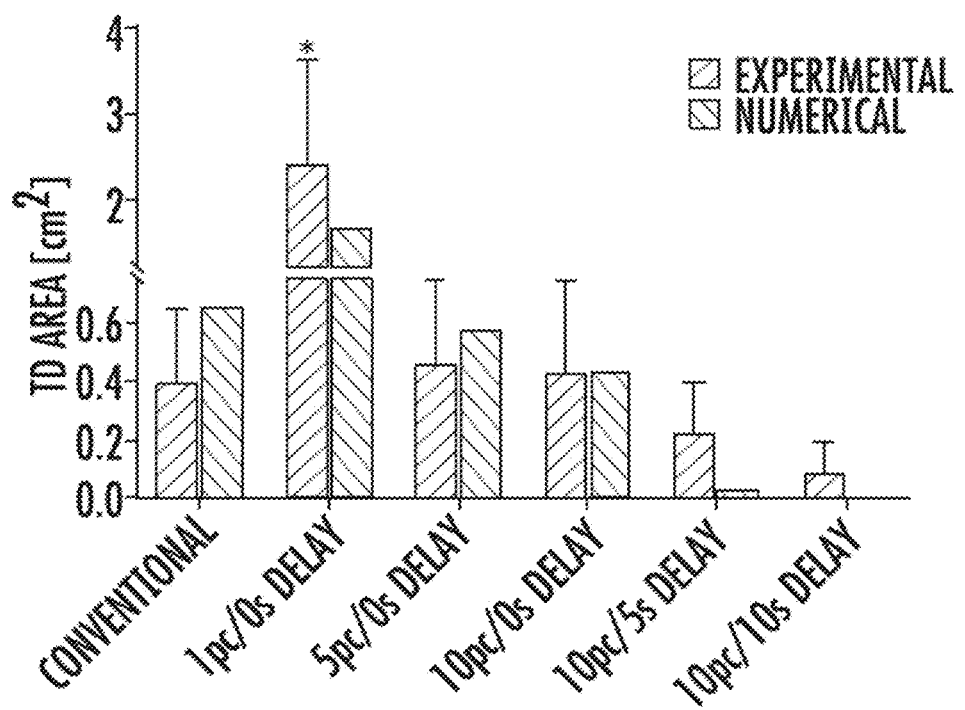

FIGS. 10A-F display representative images of the cross-sectional tissue samples for each pulsing paradigm tested, along with the corresponding ratio percentage of thermal damage to IRE ablation. Each pulsing paradigm in this example involved conventional EPAP. FIG. 10G shows the percentage ratio of white tissue coagulation area to IRE treatment zone area for each pulsing scheme. These measurements illustrated that 20.59±6.48% of the ablation presented white tissue coagulation for the "1 pulse cycle, 0 s delay" pulse scheme, whereas all other groups demonstrated less than 5% white tissue coagulation associated with the ablation (p<0.0001, all pairwise comparisons). Similarly, FIGS. 10H and 10I express average IRE treatment zone area and white tissue coagulation area, respectively. As shown in FIG. 10H, the IRE treatment zone across the different protocols remained relatively about the same: Conventional (see also FIG. 10A), 1 pulse cycle with 0 s delay (see also FIG. 10B), 5 pulse cycle with 0 s delay (see also FIG. 10C), 10 pulse cycle with 0 s delay (see also FIG. 10D), 10 pulse cycle with 5 s delay (see also FIG. 10E), and 10 pulse cycle with 10 s delay (see also FIG. 10F). No statistical significance was found between IRE treatment zone area for any pulse schemes evaluated. As shown in FIG. 10I, the amount of thermal damage as measured by white tissue coagulation was different across the different protocols in that less white tissue coagulation was seen as the number of cycles increased and/or as the delay increased, with the 10 pulse cycle with 10 s delay showing the least amount of tissue damage. However, the "1 pulse cycle, 0 s delay" pulse scheme produced 2.53±0.48 cm$^2$ of white tissue coagulation while all other groups demonstrated less than 0.5 cm$^2$ white tissue coagulation associated with the IRE treatment zone (p<0.0001, all comparisons).

Figures 11A, 11B:
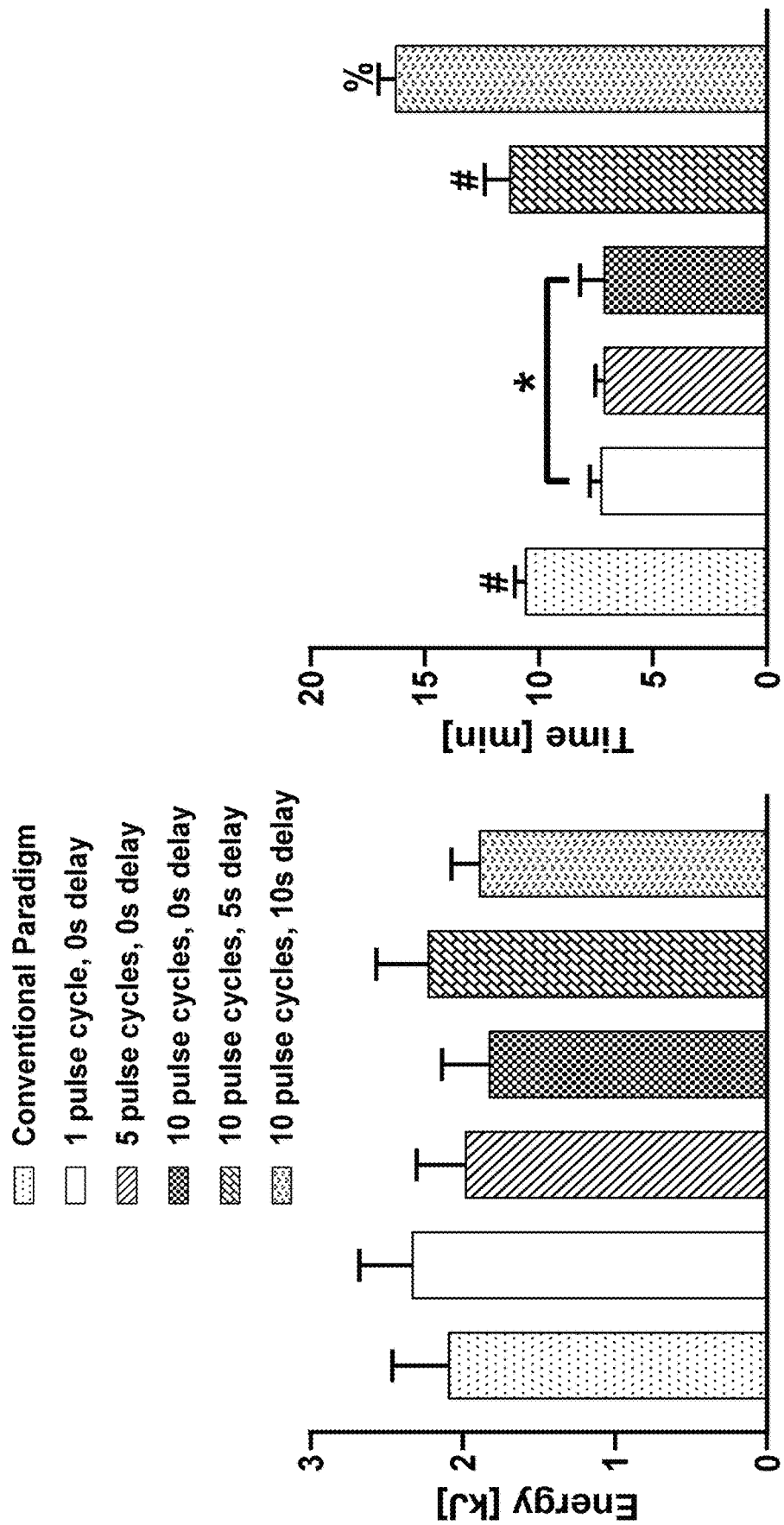
FIG. 11A is a graph showing the calculated average energy delivered to the tissue for the amount of time shown in FIG. 11B (the energy deposited was about the same across the groups).
FIG. 11B is a graph showing the measured treatment time for each pulse paradigm, where *, #, and % groups are significantly different from one another ($p<0.0001$, all pairwise comparisons).

FIG. 11A illustrates the energy delivered for each pulse paradigm tested. No statistical significance was found between experimental groups in energy deposition, thus the energy deposited was about the same across the groups. The "1 pulse cycle, 0 s delay" group induced an average energy of 2.33±0.35 kJ, while the conventional pulse scheme yielded a 2.09±0.37 kJ on average. The "5 pulse cycle, 0 s delay", "10 pulse cycle, 0 s delay", and the "10 pulse cycle, 10 s delay" averages of 1.98±0.32 kJ, 1.88±0.34 kJ and 1.89±0.23 kJ, of energy respectively. The "10 pulse cycle, 5 s delay" pulse scheme generated an average energy of 2.14±0.38 kJ.

FIG. 11B expresses the measured treatment duration. Here, all pulse cycle groups with a zero second delay were statistically similar in treatment time and further displayed shorter treatment times on average (approximately 7 minutes for all 0 s delay pulse schemes; p<0.0001 all pairwise comparisons, group *) than other pulse schemes. The conventional paradigm and "10 pulse cycle, 5 s delay" group were found to be statistically similar compared to other groups (10.61±0.46 min, and 11.29±1.11 min; p<0.0001 all pairwise comparisons, group #). Lastly, the treatment time for the "10 pulse cycle, 10 s delay" group was the longest on average and statistically greater than all other groups (16.29±0.76 min, p<0.0001 all pairwise comparisons, group %).

Numerical Model Results

Here we assumed that the minimum electric field required to induce cell death with HFIRE (the lethal threshold) could be determined by comparing the measured ablation area with those predicted from the numerical model (see C. B. Arena, C. S. Szot, P. A. Garcia, M. N. Rylander, and R. V. Davalos, "A three-dimensional in vitro tumor platform for modeling therapeutic irreversible electroporation," Biophys. J., vol. 103, no. 9, pp. 2033-2042, 2012; J. W. Ivey, E. L. Latouche, M. B. Sano, J. H. Rossmeisl, R. V. Davalos, and S. S. Verbridge, "Targeted cellular ablation based on the morphology of malignant cells," Sci. Rep., vol. 5, pp. 1-17, 2015; and E. M. Wasson, J. W. Ivey, S. S. Verbridge, and R. V. Davalos, "The feasibility of enhancing susceptibility of glioblastoma cells to IRE using a calcium adjuvant," vol. 45, no. 11, pp. 2535-2547, 2018). The electric field that yielded the closest matching volumetric dimensions would be designated as the lethal threshold. FIG. 10H illustrates the area of tissue within the electric field threshold of 601 V/cm for each pulse paradigm. This threshold was most similar to the experimentally measured IRE areas for each pulse paradigm (~12 cm$^2$). There was no more than 3% difference, between any of the pulsing schemes 400, 600, 800, or 1000 V/cm. A volume integration for tissue greater than 601 V/cm was also performed, which revealed approximately 25 cm$^3$ of tissue with an electric field threshold of 601 V/cm.

FIG. 10I illustrates the thermally damaged tissue area for each pulse scheme. The "1 pulse cycle, 0 s delay" pulse group portrayed 1.68 cm$^2$ of tissue experiencing white tissue coagulation (Ω=2.3), well within one standard deviation of the experimental data (difference of 0.72 cm$^2$). The conventional pulsing protocol yielded at 0.65 cm$^2$ of tissue experiencing white tissue coagulation. The "10 pulse cycle, 10 s delay" pulse cycle sequence illustrated the least, with an area of 0.005 cm$^2$, or a 99.3% reduction of thermal damage area in comparison to the conventional pulse scheme. As a result, the practitioner is able to locate electrode(s) closer to critical non-target structures and thus in a more desired location for treatment and/or expand the treatment area because of the reduction of any thermal effect as compared to the conventional pulse scheme. Each multi-cycle pulsing paradigms illustrated less area thermal damage on average than the single-cycle scheme ("1 pulse cycle, 0 s delay" and the conventional pulse scheme).

The percentage ratio of thermal injury area to IRE ablation area was also evaluated numerically. These numerical results were within one standard deviation of the experimentally measured results and indicated that as much as 13.14% of the "1$^{st}$ pulse cycle, 0 s delay" ablation area would present white tissue coagulation. FIG. 10G illustrates these findings in detail.

Further, a direct comparison between the conventional and enhanced EPAPs was performed to identify any significant differences in IRE or white tissue coagulation areas. The results indicate essentially no changes to the IRE area (FIG. 12A) and a slight reduction in thermal damage area (FIG. 12B) for all pulse paradigms. Overall, the incorporation of cycled pulsing, with an enhanced EPAP could reduce the surface area and volumetric thermal damage as much as 13.6% in comparison to the conventional pulse paradigm, while maintaining the effective electric field thresholds within 2.1%. The percentage ratio of thermal damage area to IRE treatment zone area is shown in FIG. 12C, which shows a similar overall reduction in thermal damage by using cycled pulsing with enhanced EPAP.

Figure 13A:
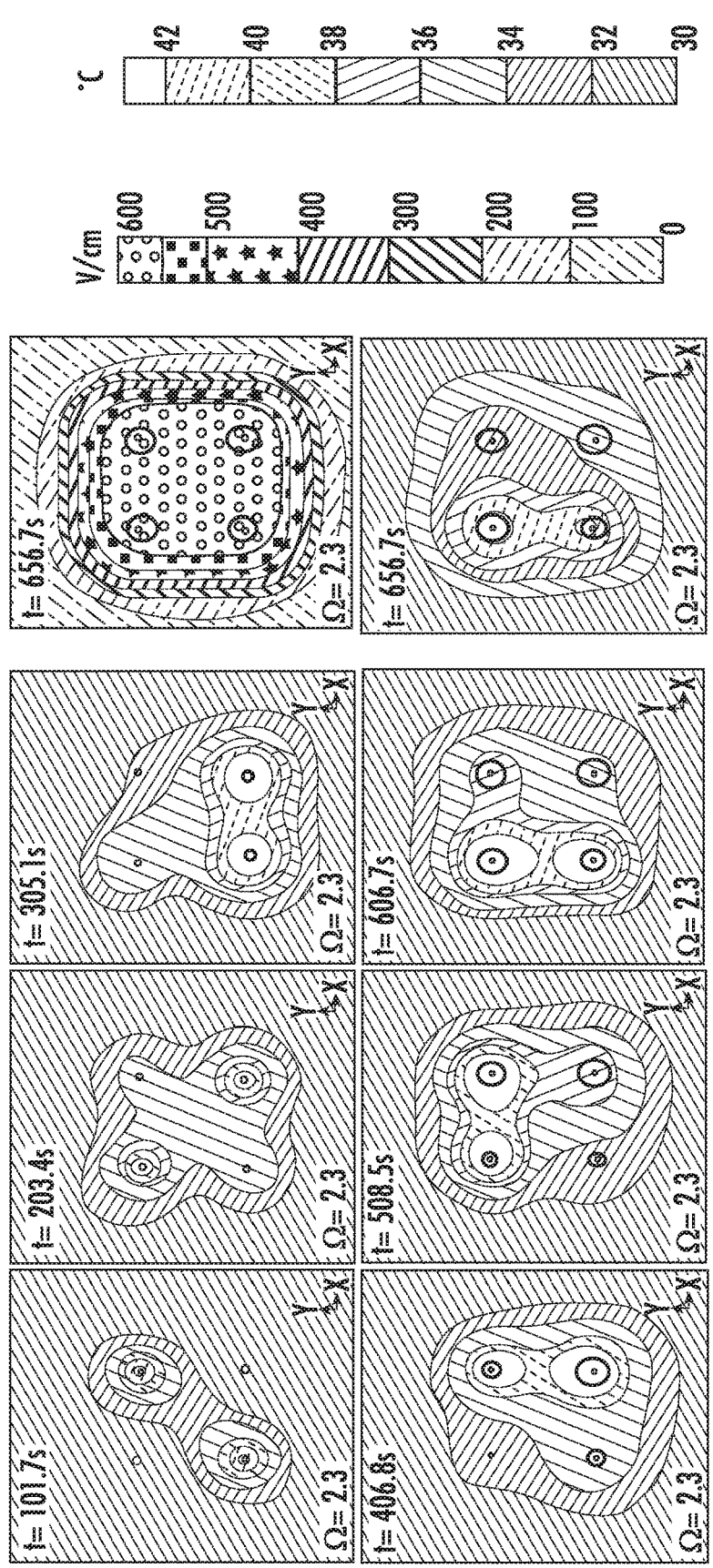
FIGS. 13A-13C are series of illustrations showing the numerically derived thermal distribution at the completion of each initial electrode pair activation, as well as the final electric field and thermal distribution 50 seconds post therapy for a conventional paradigm and conventional EPAP (FIG. 13A), a cycled pulsing paradigm (10 pulse cycles, 5 s delay) with a conventional EPAP (FIG. 13B), a cycled pulsing paradigm (10 pulse cycles, 5 s delay) with an enhanced EPAP (FIG. 13C). The time at each electrode pair activation is displayed in the top left corner. The area in which the onset of thermal damage occurs ($\Omega$=2.3) is encircled in bold. Initial temperature within the numerical model was set to $T_o$=30° C. to match the experimental settings.
Figure 13B:
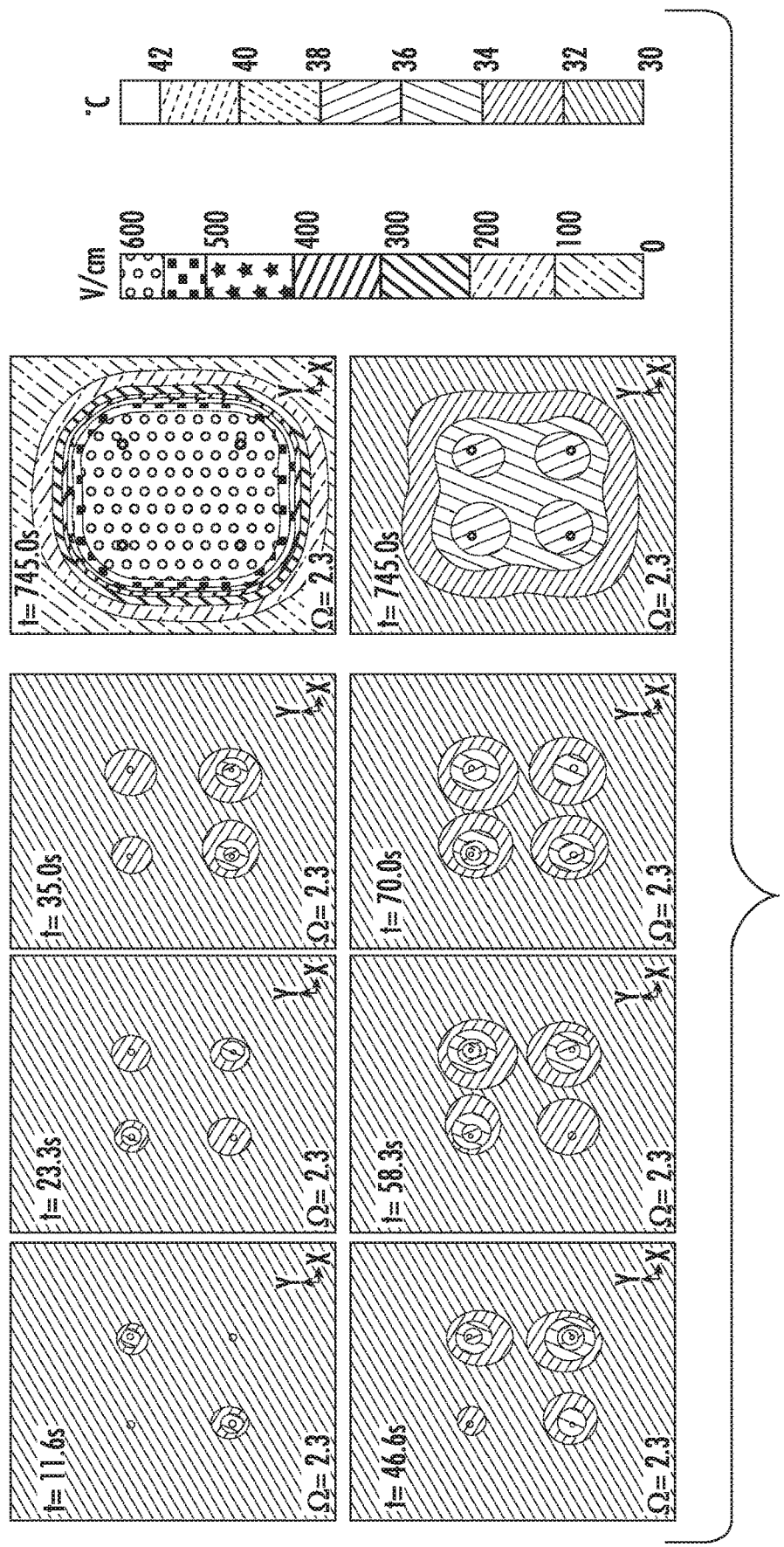
Figure 13C:
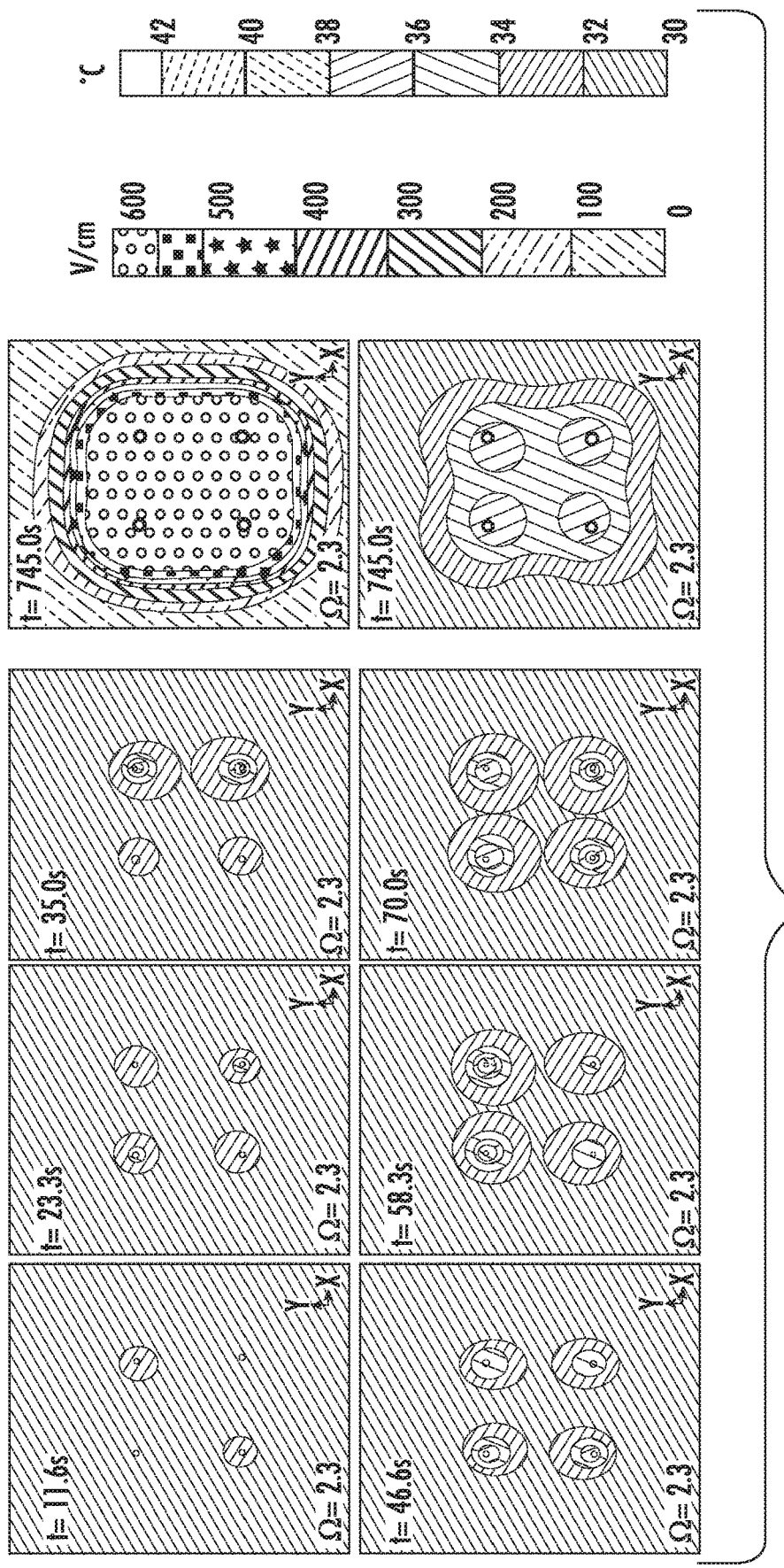

FIGS. 13A-C shows the numerical results for the comparison of (a) the conventional sequence using a conventional EPAP sequence too (FIG. 13A), (b) a 10 pulse cycle, 5 s delay cycled pulse paradigm (FIG. 13B) using a conventional EPAP sequence (i.e., the same conventional EPAP sequence as in FIG. 13A), and (c) the same cycled pulse paradigm model as in FIG. 13B using an enhanced EPAP sequence (FIG. 13C) (enhanced EPAP sequence meaning here that the same pulse protocol of FIG. 13B is applied, but that no single electrode is activated immediately consecutively more than twice). As shown, the amount of thermal damage with the conventional protocol (FIG. 13A) was larger (see the larger areas circled around the electrodes) than that of the other two protocols (FIGS. 13B and 13C). Analysis was performed across the plane, at the midpoint of the electrodes within the 3D model. A series of time-lapse images illustrates the thermal distribution at the first cycle of each electrode pair. The farthest right panels illustrate the thermal distribution and effective electric field at the completion of each treatment. Further, the boundary at which white tissue coagulation ($\Omega$=2.3) occurs is overlaid and outlined in bold. The thermal distribution throughout and completion of treatment illustrates an asymmetric thermal distribution for the conventional pulse paradigm, while both cycled pulsing schemes illustrated uniform temperature distributions and smaller thermal damage volumes. The protocol of FIG. 13A for the conventional treatment can be correlated with the "conventional" treatment results (first set of results) shown in FIGS. 10G-I, 11A-B and 12A-C. The protocols of FIGS. 13B-C for the 10 pulse cycle with 5 s delay can be correlated with the "10 pc/5 s delay" results (second set of results from left) of FIGS. 10G-I, 11A-B and 12A-C.

Discussion

The inventors studied the effects of varying pulsing paradigms on induced current, resultant temperature, and treatment zone size were investigated for multi-electrode (4-electrode configuration) IRE treatments. The desirable effects of IRE treatments are not dependent on thermal events, but thermal damage can still occur due to Joule heating. The restructuring of the pulse delivery mechanism with the intent to redistribute the delivered energy uniformly across all electrodes and reduce the successive on (energized) time that any active electrode may experience throughout treatment could improve IRE treatment by limiting thermal tissue damage, preventing generator crashes, and enhancing energy delivery to the tissue.

Finite Element Analysis provided insight into the effects of cycled pulsing on the temperature distribution, and thermal injury distribution. More specifically, it was found that cycled pulsing patterns mitigate the overall temperature rise and thermal damage in comparison to single cycle pulsing schemes. Further, the work reported here illuminated the potential importance of electrode-pair activation-order within the pulsing scheme, as any reduction in potential thermal damage is critical for clinicians operating in sensitive regions.

The experimental results utilizing a perfused organ model as a test bed demonstrated that the use of cycled pulse paradigms can reduce the effects of Joule heating while effectively maintaining and, in some cases, improving the IRE treatment zone dimensions in comparison to treatments administered with a conventional pulse scheme. We have verified the effects of using pulse cycle patterns on electrical current, tissue temperature, treatment zone size, and total treatment time for several pulsing schemes. The results indicated that the "5 pulse cycle, 0 s delay" pulsing scheme provided the largest ablation areas while maintaining a relatively low electrical current output and thermal damage index on average. By comparison, the conventional pulsing scheme yielded the second smallest ablation area, a longer treatment time, and a slightly larger electrical current output on average. Regardless, all of the multi-cycle pulse paradigms evaluated yielded a lower current output and larger ablation area than both single-cycle pulse schemes. Further, experimental testing established that inter-cycle delays become a critical factor in determining statistical significance between pulse schemes.

It should be noted that the numerical models described throughout this work define tissue temperature at 30° C. to match the perfused organ model settings, rather than a more representative tissue temperature during surgery (~35° C.). Models were developed to evaluate the thermal damage volumes at these elevated temperatures. These models revealed larger thermal injury volumes (<2.2 cm$^3$ difference), however, the differences in thermally damaged area for cycled pulse schemes in comparison to the conventional pulse paradigm remained similar.

Here, the inventors tested the effects of using several pulse-timing paradigms on electrical current, tissue temperature, and tissue treatment size. This work successfully shows that cycled pulsing schemes reduce the electrical current, increase the treatment zone size, and ultimately maintain a low tissue temperature in comparison to conventional pulsing schemes in an ex vivo perfused porcine liver model. As demonstrated, cycled pulsing patterns can be an effective tool for enhancing the efficacy of IRE application in clinical practice and would be expected to lead to better overall outcomes for patients.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method of treating tissue, the method comprising:
using a number of electrodes, delivering a total number of electrical pulses to a target region by:
   activating a number of pairs of the electrodes in a number of cycles;
   wherein the activating is performed a number of times that equals the total number of electrical pulses, divided by the number of pairs of electrodes, divided by the number of cycles;
   wherein the activating is performed such that within at least one cycle:
      first and second electrode pairs are activated in sequence; and
      third and fourth electrode pairs are activated in sequence;
      wherein the first electrode pair comprises different electrodes than the second electrode pair and the third electrode pair comprises different electrodes than the fourth electrode pair;
   whereby electrical energy is strategically distributed to sub-regions within the outline of the target region to treat tissue while mitigating one or more of thermal effects, thermal damage, potential for Joule heating, or delivery of electric current to tissue of the target region; and
   wherein at least one of the electrodes is a surface electrode and at least one of the electrodes is a needle electrode.

2. The method of claim 1, wherein each pair of electrodes delivers a pulse train with no delay between pulses in the pulse train.

3. The method of claim 1, further comprising adding one or more delay between electrical pulses and/or bursts in a manner to further mitigate one or more of the thermal effects, thermal damage, potential for Joule heating, or delivery of electric current to tissue of the target region.

4. The method of claim 1, wherein the thermal effects or thermal damage are evidenced by an amount of white tissue coagulation.

5. The method of claim 1, wherein a ratio of thermally damaged tissue area to ablation area is less than 5%.

6. The method of claim 1, wherein the activating is performed such that no single electrode is activated more than two consecutive times within a cycle.

7. The method of claim 1, wherein the same and/or different sub-regions of the target region are treated consecutively.

8. The method of claim 1, wherein the activating comprises applying a first pulse train to one pair of electrodes, applying a second pulse train to a subsequent pair of electrodes, optionally applying additional pulse trains to one or more additional pairs of electrodes, then repeating such activating over the number of cycles until the total number of determined electrical pulses is reached.

9. The method of claim 1, wherein the delivering of the electrical pulses causes electroporation based therapy, electroporation, irreversible electroporation, reversible electroporation, electrochemotherapy, electrogenetherapy, supraporation, and/or high frequency irreversible electroporation, or combinations thereof.

10. The method of claim 9, wherein the delivering causes IRE and/or HFIRE.

11. The method of claim 1, wherein one or more of the following parameters are employed for the delivering of the electrical pulses:
   a) the number of cycles is from one to ten;
   b) one or more delays of 0 to 10 seconds each (within a pulse train and/or between activation of pairs and/or between cycles);
   c) a number of pulses per cycle and/or pulses per pair of 10 to 200;
   d) a total number of pulses of 100 to 5000; and/or
   e) a total number of pairs of electrodes of from 1 to 30.

12. The method of claim 1, wherein the delivering is performed:
   using a voltage ranging from 0 V to 10,000 V; and/or
   with pulse lengths in the ns to second range; and/or
   with a frequency in the range of 0 Hz to 100 MHz; and/or
   with a waveform that is square, triangular, trapezoidal, exponential decay, sawtooth, sinusoidal, and/or alternating polarity; and/or
   with a total number of pulses ranging from 1-5,000 pulses; and/or
   with a total number of pulses per pulse train ranging from 1-5,000 pulses.

13. The method of claim 1, wherein the first electrode pair comprises two electrodes spaced further apart than two electrodes of the third and/or fourth electrode pairs.

14. A method of treating a tissue with electrical energy while mitigating thermal damage to the tissue, the method comprising:
   distributing a total number of electrical pulses to the tissue by way of a plurality of electrode pairs over a plurality of cycles,
   such that each electrode pair is activated to receive one or more pulse train during each cycle of the plurality of cycles, and
   such that within at least one cycle:
      first and second electrode pairs are activated in sequence; and
      third and fourth electrode pairs are activated in sequence;
   wherein the first electrode pair comprises different electrodes than the second electrode pair and the third electrode pair comprises different electrodes than the fourth electrode pair; and
   wherein at least one of the electrodes of one or more of the electrode pairs comprises one or more surface electrodes and at least one of the electrodes of one or more of the electrode pairs comprises one or more needle electrodes.

15. The method of claim 14, wherein each pair of electrodes delivers a pulse train with no delay between pulses in the pulse train.

16. The method of claim 14, further comprising introducing a delay between one or more of the electrical pulses and/or one or more pulse train.

* * * * *